(12) United States Patent
Desai et al.

(10) Patent No.: US 9,597,409 B2
(45) Date of Patent: *Mar. 21, 2017

(54) METHODS OF TREATING CANCER

(71) Applicant: Abraxis BioScience, LLC, Los Angeles, CA (US)

(72) Inventors: Neil P. Desai, Los Angeles, CA (US); Patrick Soon-Shiong, Los Angeles, CA (US)

(73) Assignee: ABRAXIS BIOSCIENCE, LLC, Los Angeles, CA (US)

( * ) Notice: Subject to any disclaimer, the term of this patent is extended or adjusted under 35 U.S.C. 154(b) by 342 days.

This patent is subject to a terminal disclaimer.

(21) Appl. No.: 13/782,990

(22) Filed: Mar. 1, 2013

(65) Prior Publication Data
US 2014/0072643 A1 Mar. 13, 2014

Related U.S. Application Data

(63) Continuation of application No. 13/073,824, filed on Mar. 28, 2011.

(60) Provisional application No. 61/318,774, filed on Mar. 29, 2010, provisional application No. 61/433,132, filed on Jan. 14, 2011.

(51) Int. Cl.
| *A61K 31/337* | (2006.01) |
| *A61K 9/14* | (2006.01) |
| *A61K 47/48* | (2006.01) |
| *A61K 31/555* | (2006.01) |
| *A61N 5/10* | (2006.01) |
| *A61K 45/06* | (2006.01) |
| *A61K 33/24* | (2006.01) |

(52) U.S. Cl.
CPC ........ *A61K 47/48284* (2013.01); *A61K 9/146* (2013.01); *A61K 31/337* (2013.01); *A61K 31/555* (2013.01); *A61K 33/24* (2013.01); *A61K 45/06* (2013.01); *A61N 5/10* (2013.01); *A61K 9/14* (2013.01)

(58) Field of Classification Search
CPC .......... A61K 47/48; A61K 9/14; A61K 9/141; A61K 31/337
See application file for complete search history.

(56) References Cited

U.S. PATENT DOCUMENTS

| 5,362,478 A | 11/1994 | Desai et al. |
| 5,439,686 A | 8/1995 | Desai et al. |
| 5,470,571 A | 11/1995 | Herlyn et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,510,118 A | 4/1996 | Bosch et al. |
| 5,512,268 A | 4/1996 | Grinstaff et al. |
| 5,534,270 A | 7/1996 | De Castro |
| 5,558,864 A | 9/1996 | Bendig et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,651,986 A | 7/1997 | Brem et al. |
| 5,662,883 A | 9/1997 | Bagchi et al. |
| 5,665,382 A | 9/1997 | Grinstaff et al. |
| 5,665,383 A | 9/1997 | Grinstaff et al. |
| 5,690,928 A | 11/1997 | Heimbrook et al. |
| 5,733,925 A | 3/1998 | Kunz et al. |
| 5,744,460 A | 4/1998 | Müller et al. |
| 5,859,018 A | 1/1999 | Brown et al. |
| 5,873,904 A | 2/1999 | Ragheb et al. |
| 5,886,026 A | 3/1999 | Hunter et al. |
| 5,916,596 A | 6/1999 | Desai et al. |
| 5,977,163 A | 11/1999 | Li et al. |
| 5,981,568 A | 11/1999 | Kunz et al. |
| 5,994,341 A | 11/1999 | Hunter et al. |
| 5,997,904 A | 12/1999 | Magdassi et al. |
| 6,096,070 A | 8/2000 | Ragheb et al. |
| 6,096,331 A | 8/2000 | Desai et al. |
| 6,143,276 A | 11/2000 | Unger |
| 6,239,124 B1 | 5/2001 | Zenke et al. |
| 6,268,390 B1 | 7/2001 | Kunz |
| 6,306,421 B1 | 10/2001 | Kunz et al. |
| 6,506,405 B1 | 1/2003 | Desai et al. |
| 6,515,009 B1 | 2/2003 | Kunz et al. |
| 6,528,067 B1 | 3/2003 | Magdassi et al. |
| 6,537,579 B1 | 3/2003 | Desai et al. |
| 6,544,544 B2 | 4/2003 | Hunter et al. |

(Continued)

FOREIGN PATENT DOCUMENTS

| EP | 0 584 001 A1 | 2/1994 |
| EP | 1 650 220 B1 | 4/2006 |

(Continued)

OTHER PUBLICATIONS

US 8,968,752, 03/2015, Desai et al. (withdrawn)

(Continued)

*Primary Examiner* — Samira Jean-Louis

(74) *Attorney, Agent, or Firm* — Morrison & Foerster LLP

(57) ABSTRACT

The present invention provides methods and compositions for treating non-small-cell lung cancer (NSCLC) by administering a) a composition comprising nanoparticles that comprise paclitaxel and an albumin and b) a platinum-based agent (e.g., carboplatin). The present application also provides methods of treating prostate cancer by administering to the individual a) an effective amount of a composition comprising nanoparticles comprising docetaxel and an albumin; and b) an effective amount of a steroid.

27 Claims, No Drawings

(56) References Cited

U.S. PATENT DOCUMENTS

| | | |
|---|---|---|
| 6,548,531 B2 | 4/2003 | Breimer et al. |
| 6,565,842 B1 | 5/2003 | Desai et al. |
| 6,566,405 B2 | 5/2003 | Weidner et al. |
| 6,569,441 B2 | 5/2003 | Kunz et al. |
| 6,652,884 B2 | 11/2003 | Falciani |
| 6,682,758 B1 | 1/2004 | Tabibi et al. |
| 6,689,803 B2 | 2/2004 | Hunter |
| 6,727,256 B1 | 4/2004 | Carter et al. |
| 6,730,699 B2 | 5/2004 | Li et al. |
| 6,749,868 B1 | 6/2004 | Desai et al. |
| 6,752,803 B2 | 6/2004 | Goldman et al. |
| 6,753,006 B1 | 6/2004 | Desai et al. |
| 6,872,715 B2 | 3/2005 | Santi et al. |
| 6,884,817 B2 | 4/2005 | Li et al. |
| 6,884,879 B1 | 4/2005 | Baca et al. |
| 6,929,818 B2 | 8/2005 | Luthra et al. |
| 7,038,071 B2 | 5/2006 | Lal |
| 7,101,568 B2 | 9/2006 | Dang et al. |
| 7,129,368 B2 | 10/2006 | Lal et al. |
| 7,141,576 B2 | 11/2006 | Lackey et al. |
| 7,232,919 B2 | 6/2007 | Lal |
| 7,332,568 B2 | 2/2008 | Trieu et al. |
| 7,405,208 B2 | 7/2008 | Santi et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,415,304 B2 | 4/2013 | Trieu et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 9,393,318 B2 | 7/2016 | Desai et al. |
| 2002/0031505 A1 | 3/2002 | Bissery |
| 2002/0169140 A1 | 11/2002 | Prendergast |
| 2003/0133955 A1 | 7/2003 | Desai et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2003/0216369 A1 | 11/2003 | Rosen et al. |
| 2003/0220354 A1 | 11/2003 | McClure et al. |
| 2004/0033271 A1 | 2/2004 | Lederman |
| 2004/0047835 A1 | 3/2004 | Bianco |
| 2004/0053946 A1 | 3/2004 | Lackey et al. |
| 2004/0126400 A1 | 7/2004 | Iversen et al. |
| 2004/0143004 A1 | 7/2004 | Fargnoli et al. |
| 2004/0167079 A1 | 8/2004 | Tidmarsh |
| 2004/0248781 A1 | 12/2004 | Kerbel |
| 2005/0000900 A1 | 1/2005 | Huang et al. |
| 2005/0002983 A1 | 1/2005 | Johnson, Jr. |
| 2005/0004002 A1 | 1/2005 | Desai et al. |
| 2005/0026893 A1 | 2/2005 | Johnson, Jr. |
| 2005/0032699 A1 | 2/2005 | Holash et al. |
| 2005/0058684 A1 | 3/2005 | Shanley et al. |
| 2005/0095267 A1 | 5/2005 | Campbell et al. |
| 2005/0186208 A1 | 8/2005 | Fyfe et al. |
| 2005/0203174 A1 | 9/2005 | Santi et al. |
| 2006/0003931 A1 | 1/2006 | Eigenbrot, Jr. et al. |
| 2006/0013819 A1 | 1/2006 | Kelsey |
| 2006/0062821 A1 | 3/2006 | Simhambhatla et al. |
| 2006/0135486 A1 | 6/2006 | Owa et al. |
| 2006/0165744 A1 | 7/2006 | Jamil et al. |
| 2006/0188566 A1 | 8/2006 | Liversidge et al. |
| 2006/0199248 A1 | 9/2006 | Trieu et al. |
| 2007/0093547 A1 | 4/2007 | Desai et al. |
| 2007/0116774 A1 | 5/2007 | Desai et al. |
| 2007/0117133 A1 | 5/2007 | Trieu et al. |
| 2007/0129448 A1 | 6/2007 | Desai et al. |
| 2007/0166388 A1 | 7/2007 | Desai et al. |
| 2007/0196361 A1 | 8/2007 | Soon-Shiong et al. |
| 2007/0207196 A1 | 9/2007 | Zhang |
| 2008/0045559 A1 | 2/2008 | Zhang et al. |
| 2008/0063699 A1 | 3/2008 | Teifel et al. |
| 2008/0085902 A1 | 4/2008 | Bold et al. |
| 2008/0146598 A1 | 6/2008 | Bianco |
| 2008/0255035 A1 | 10/2008 | Trieu et al. |
| 2008/0280987 A1 | 11/2008 | Desai et al. |
| 2009/0018078 A1 | 1/2009 | Labhasetwar |
| 2009/0047337 A1 | 2/2009 | Mescheder et al. |
| 2009/0263483 A1 | 10/2009 | Desai et al. |
| 2009/0304805 A1 | 12/2009 | Desai et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0183728 A1 | 7/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2011/0165256 A1 | 7/2011 | Desai et al. |
| 2011/0196026 A1 | 8/2011 | De et al. |
| 2012/0004177 A1 | 1/2012 | Desai et al. |
| 2012/0039805 A1 | 2/2012 | Lisanti et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0177743 A1 | 7/2012 | Desai et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |

(56) References Cited

U.S. PATENT DOCUMENTS

| | | |
|---|---|---|
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0008330 A1 | 1/2016 | Desai |
| 2016/0015681 A1 | 1/2016 | Desai |
| 2016/0015817 A1 | 1/2016 | Benettaib et al. |

FOREIGN PATENT DOCUMENTS

| | | |
|---|---|---|
| EP | 1 862 179 A1 | 12/2007 |
| JP | 2006-524632 A | 11/2006 |
| JP | 2010-509331 A | 3/2010 |
| WO | WO-91/15193 A1 | 10/1991 |
| WO | WO-94/18954 A1 | 9/1994 |
| WO | WO-95/03036 A1 | 2/1995 |
| WO | WO-98/14174 A1 | 4/1998 |
| WO | WO-98/14175 A1 | 4/1998 |
| WO | WO-99/00113 A1 | 1/1999 |
| WO | WO-00/06152 A1 | 2/2000 |
| WO | WO-00/64437 A1 | 11/2000 |
| WO | WO-00/71079 A2 | 11/2000 |
| WO | WO-00/71079 A3 | 11/2000 |
| WO | WO-00/71163 A1 | 11/2000 |
| WO | WO-01/34174 A2 | 5/2001 |
| WO | WO-01/34174 A3 | 5/2001 |
| WO | WO-01/76567 A1 | 10/2001 |
| WO | WO-01/89522 A1 | 11/2001 |
| WO | WO-02/24179 A2 | 3/2002 |
| WO | WO-02/24179 A3 | 3/2002 |
| WO | WO-02/056912 A2 | 7/2002 |
| WO | WO-02/056912 A3 | 7/2002 |
| WO | WO-02/076459 A1 | 10/2002 |
| WO | WO-02/087545 A1 | 11/2002 |
| WO | WO-03/008665 A1 | 1/2003 |
| WO | WO-03/096944 A1 | 11/2003 |
| WO | WO-2004/017964 A1 | 3/2004 |
| WO | WO-2004/052401 A2 | 6/2004 |
| WO | WO-2004/052401 A3 | 6/2004 |
| WO | WO-2005/000266 A2 | 1/2005 |
| WO | WO-2005/000266 A3 | 1/2005 |
| WO | WO-2005/000900 A1 | 1/2005 |
| WO | WO-2005/039533 A1 | 5/2005 |
| WO | WO-2005/117952 A2 | 12/2005 |
| WO | WO-2005/117952 A3 | 12/2005 |
| WO | WO-2005/117978 A2 | 12/2005 |
| WO | WO-2005/117978 A3 | 12/2005 |
| WO | WO-2005/117986 A2 | 12/2005 |
| WO | WO-2005/117986 A3 | 12/2005 |
| WO | WO-2006/089290 A1 | 8/2006 |
| WO | WO-2006/090928 A1 | 8/2006 |
| WO | WO-2006/117220 A2 | 11/2006 |
| WO | WO-2006/117220 A3 | 11/2006 |
| WO | WO-2006/124684 A2 | 11/2006 |
| WO | WO-2006/124684 A3 | 11/2006 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2007/059116 A2 | 5/2007 |
| WO | WO-2007/107305 A2 | 9/2007 |
| WO | WO-2007/107305 A3 | 9/2007 |
| WO | WO-2008/027055 A1 | 3/2008 |
| WO | WO-2008/057562 A1 | 5/2008 |
| WO | WO-2008/060651 A2 | 5/2008 |
| WO | WO-2008/060651 A3 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |
| WO | WO-2008/157353 A1 | 12/2008 |
| WO | WO-2009/126175 A1 | 10/2009 |
| WO | WO-2009/126401 A1 | 10/2009 |
| WO | WO-2009/126938 A1 | 10/2009 |
| WO | WO-2010/068925 A1 | 6/2010 |
| WO | WO-2010/105172 A1 | 9/2010 |
| WO | WO-2008/128169 A1 | 10/2010 |
| WO | WO-2010/118365 A1 | 10/2010 |
| WO | WO-2010/121000 A1 | 10/2010 |
| WO | WO-2011/025838 A1 | 3/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149451 A1 | 11/2012 |
| WO | WO-2013/090634 A1 | 6/2013 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |

OTHER PUBLICATIONS

Abou-Alfa, G. K. et al. (Sep. 20, 2006). "Randomized Phase III Study of Exatecan and Gemcitabine Compared with Gemcitabine Alone in Untreated Advanced Pancreatic Cancer," *J. Clin. Oncol.* 24(27):4441-4447.

Abraxis Bioscience, Inc. (Feb. 4, 2009). "ABRAXANE Now Available in Germany and the United Kingdom with Additional EU Countries to follow," Article located at URL http://web.archive.org/web/20090206124408/http://www.nanowerk.com/news/newsid=9156.php, last retrieved on Jul. 20, 2011, one page.

Abraxis Bioscience, Inc. (Mar. 17, 2010). "ABRAXANE Meets Primary Endpoint in Phase 3 Trial for Advanced Non-Small Cell Lung Cancer," Press Release located at http://www.biospace.com/news_print.aspx?NewsEntityId=174173, last visited May 3, 2010, 3 pages total.

ADIS Data Information BV. (Aug. 28, 2004). "Paclitaxel [Taxol] and Liposomal Doxorubicin [Caelyx] Cotherapy Appears to be an Effective First-line Treatment in Patients with Metastatic Breast Cancer," *Inpharma* (1452):8.

Albain, K. S. et al. (Sep. 1991). "Survival Determinants in Extensive-Stage Non-Small-Cell Lung Cancer: The Southwest Oncology Group Experience," *J. Clin. Oncol.* 9(9):1618-1626.

Alberola, V. et al. (Sep. 1, 2003). "Cisplatin Plus Gemcitabine versus a Cisplatin-Based Triplet Versus Nonplatinum Sequential Doublets in Advanced Non-Small-Cell Lung Cancer: A Spanish Lung Cancer Group Phase III Randomized Trial," *J. Clin. Oncol.* 21(17):3207-3213.

Alberts, S. R. et al. (Oct. 2005, e-pub: Aug. 5, 2005). "PS-341 and Gemcitabine in Patients with Metastatic Pancreatic Adenocarcinoma: a North Central Cancer Treatment Group (NCCTG) Randomized Phase II Study," *Annals of Oncology* 16(10):1654-1661.

Allerton, J. P. et al. (Jun. 20, 2006). "A Phase II Evaluation of the Combination of Paclitaxel Protein-bound and Carboplatin in the First-line Treatment of Advanced Non-small Cell Lung Cancer (NSCLC)," Abstract, 2006 ASCO Annual Meeting Proceedings, Part 1, *J. Clin. Oncol.* 24(18 Suppl.): Abstract No. 7127, located at http://www.asco.org/portal/site/ASCOv2/template.RAW/menuitem . . . , last visited on Jul. 19, 2009, one page.

American Cancer Society, (2009). "Cancer Facts and Figures," located at http://www.cancer.org/downloads/STT/500809web.pdf, pp. 1-72.

Anonymous (Oct. 7, 1995). "Chemotherapy in Non-Small Cell Lung Cancer: A Meta-Analysis Using Updated Data on Individual

(56) References Cited

OTHER PUBLICATIONS

Patients From 52 Randomised Clinical Trials. Non-Small Cell Lung Cancer Collaborative Group," *Br. Med. J.* 311(7010):899-909.

Apte, M.V. et al. (Oct. 2004). "Desmoplastic Reaction in Pancreatic Cancer: Role of Pancreatic Stellate Cells," *Pancreas*, 29(3):179-187.

Ashkenas, J. (Mar./Apr. 2003). "The Metronome Ticks on," *Preclinica*, located at <http://www.preclinica.com/default.asp?page=articles&issue=0303>, last visited on Apr. 29, 2007, pp. 1-2.

Belani, C. P. et al. (Aug. 1, 2003). "Multicenter, Randomized Trial for Stage IIIB or IV Non-Small-Cell Lung Cancer Using Weekly Paclitaxel and Carboplatin Followed by Maintenance Weekly Paclitaxel or Observation," *J. Clin. Oncol.* 21(15):2933-2939.

Belani, C. (Nov. 5-9, 2006). "Developments in the Treatment of Non-Small Cell Lung Cancer with Abraxane®," CancerConnect News, located at http://news.cancerconnect.com/developments-in-the-treatment-of-non-small-cell-lung-cancer-with-abraxane/, last visited Sep. 5, 2014, three pages.

Belani, C. P. et al. (Jan. 20, 2008). "Randomized, Phase III Study of Weekly Paclitaxel in Combination With Carboplatin Versus Standard Every-3-Weeks Administration of Carboplatin and Paclitaxel for Patients With Previously Untreated Advanced Non-Small-Cell Lung Cancer," *J. Clin. Oncol.* 26(3):468-473.

Berlin, J. D. et al. (Aug. 1, 2002). "Phase III Study of Gemcitabine in Combination With Fluorouracil Versus Gemcitabine Alone in Patients With Advanced Pancreatic Carcinoma: Eastern Cooperative Oncology Group Trial E2297," *J. Clin. Oncol.* 20(15):3270-3275.

Bernstein, B.J. (Nov. 2000). "Docetaxel as an Alternative to Paclitaxel After Acute Hypersensitivity Reactions," *Ann Pharmacother* 34(11):1332-1335. (Abstract Only.).

Bertolini, F. et al. (Aug. 1, 2003). "Maximum Tolerable Dose and Low-Dose Metronomic Chemotherapy Have Opposite Effects on the Mobilization and Viability of Circulating Endothelial Progenitor Cells," *Cancer Res.* 63(15):4342-4346.

Bertino E.M. et al (Oct. 30, 2014). « 193-Phase II Trial of *Nab*-paclitaxel plus Carboplatin for Advanced NSCLC in Patients at Risk of Bleeding from VEGF Directed Therapies, » presented at PV-Poster Viewing Session and Reception, as posted on http://www.abstractsonline.com, last visited on Feb. 12, 2015, two pages.

Bocci, G. et al. (Dec. 1, 2002). "Protracted Low-Dose Effects on Human Endothelial Cell Proliferation and Survival in Vitro Reveal a Selective Antiangiogenic Window for Various Chemotherapeutic Drugs," *Cancer Res.* 62:6938-6943.

Bocci, G. et al. (Oct. 28, 2003). "Thrombospondin 1, a Mediator of the Antiangiogenic Effects of Low-dose Metronomic Chemotherapy," *Proc. Nat. Acad. Sci. USA* 100(22):12917-12922.

Bonomi, P. D. et al. (Nov. 1989). "Combination Chemotherapy Versus Single Agents Followed by Combination Chemotherapy in Stage IV Non-Small-Cell Lung Cancer: A Study of the Eastern Cooperative Oncology Group," *J. Clin. Oncol.* 7(11):1602-1613.

Bourgeois, H. et al. (Jun. 2006). "Phase I-II Study of Pegylated Liposomal Doxorubicin Combined With Weekly Paclitaxel as First-Line Treatment in Patients with Metastatic Breast Cancer," *Am. J. Clin. Oncol.* 29(3):267-275.

Bramhall, S. R. et al. (Jul. 15, 2002). "A Double-Blind Placebo-Controlled, Randomised Study Comparing Gemcitabine and Marimastat With Gemcitabine and Placebo as First Line Therapy in Patients With Advanced Pancreatic Cancer," *British J. Cancer* 87(2):161-167.

Bristol-Myers Squibb Company (Rev Jul. 2007). "TAXOL® (Paclitaxel) Injection, (Patient Information Included)," located at http://packageinserts.bms.com/pi/pi_taxol.pdf, last visited May 6, 2010, 55 pages.

Bunn, P. A. Jr. (Aug. 1989). "The Expanding Role of Cisplatin in the Treatment of Non-Small-Cell Lung Cancer," *Semin. Oncol.* 16(4)(Suppl. 6):10-21.

Carmeliet, P. et al. (Sep. 14, 2000). "Angiogenesis in Cancer and Other Diseases," *Nature* 407(6801):249-257.

Carter, D. C. et al. (1994). "Structure of Serum Albumin," in *Advances in Protein Chemistry*, Schumaker, V.N., ed., Academic Press, Inc., San Diego, CA, 45:153-203.

Cascinu, S. et al. (Feb. 2003). "Weekly Gemcitabine and Cisplatin Chemotherapy: A Well-Tolerated but Ineffective Chemotherapeutic Regimen in Advanced Pancreatic Cancer Patients. A report from the Italian Group for the Study of Digestive Tract Cancer (GISCAD)," *Ann. Oncol.* 14(2):205-208.

Cerny, T. et al. (Aug. 1994). "Docetaxel (Taxotere™) is Active in Non-Small-Cell Lung Cancer: A Phase II Trial of the EORTC Early Clinical Trials (ECTG)," *Br. J. Cancer* 70(2):384-387.

Cho, D.S. et al. (2008). "Impact of Caveolin-1 Expression on the Prognosis of Transitional Cell Carcinoma of the Upper Urinary Tract," *J. Korean Med. Sci.*, 23:296-301.

Chu, G.C. et al. (2007). "Stromal Biology of Pancreatic Cancer", *Journal of Cellular Biochemistry*, 101-887-907.

Chustecka, Z. et al. (Sep. 16, 2008). "New Drug Shows Promise in Pancreatic Cancer in Phase 2 Trial," *Medscape Medical News*, located at htpp://www.medscape.com/viewarticle/580571, last visited Nov. 19, 2009, 2 pages.

Colucci, G. et al. (Feb. 15, 2002). "Gemcitabine Alone or with Cisplatin for the Treatment of Patients with Locally Advanced and/or Metastatic Pancreatic Carcinoma: A Prospective, Randomized Phase III Study of the Gruppo Oncologia dell'Italia Meridionale," *Cancer* 94(4) :902-910.

Crinò, L. et al. (Nov. 1999). "Gemcitabine and Cisplatin versus Mitomycin, Ifosfamide, and Cisplatin in Advanced Non-Small-Cell Lung Cancer: A Randomized Phase III Study of the Italian Lung Cancer Project," *J. Clin. Oncol.* 17(11):3522-3530.

Curry, S. et al. (Sep. 1998). "Crystal Structure of Human Serum Albumin Complexed with Fatty Acid Reveals an Asymmetric Distribution of Binding Sites," *Nat. Struct. Biol.* 5(9):827-835.

Damascelli, B. et al. (Nov. 15, 2001). "Intraarterial Chemotherapy with Polyoxyethylated Castor Oil Free Paclitaxel, Incorporated in Albumin Nanoparticles (ABI-007)," *Cancer* 92(10):2592-2602.

Damascelli, B. et al. (Jul. 2003). "A Novel Intraarterial Chemotherapy Using Paclitaxel in Albumin Nanoparticles to Treat Advanced Squamous Cell Carcinoma of the Tongue: Preliminary Findings," *AJR* 181:253-260.

Dennis, A. et al. (2007). "hERG Channel Trafficking: Novel Targets in Drug-Induced Long QT Syndrome," *Biochem. Soc. Trans.* 35(5):1060-1063.

Depierre, A. et al. (Mar. 1988). "Phase II Stud of Navelbine (NVB) in Non Small Cell Lung Cancer (NSCLC)," *Proc. Am. Soc. Clin. Oncol*, 24th Annual Meeting of the American Society of Clinical Oncology (ASCO), May 22-24, 1988, Proceedings of ASCO, New Orleans, Louisiana, vol. 7, p. 201, Abstract No. 778.

Desai, N. et al. (Jul. 2003). "Oral Bioavailability of Paclitaxel in a Novel, Cremophor El-free, Protein-based Nanoparticle Preparation," *Proc. Amer. Assn. for Cancer Res.* 44(2):732, Abstract presented at the 94th Annual Meeting of ASCR, Jul. 11-14, 2003, Washington, Washington, D.C., vol. 44, 2nd edition, Abstract No. 3673, 3 pages.

Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared With Cremophor-Based Paclitaxel," *Clin. Cancer Res.* 12(4):1317-1324.

Desai, N. et al. (Nov. 2006). "Enhanced Antitumor Activity and Safety of Albumin-Bound Nab-Docetaxel Versus Polysorbate 80-Based Docetaxel," Poster No. 152, *EJC Supplements* 4(12):49, 18th Symposium on Molecular Targets and Cancer Therapeutics, Prague, Czech Republic, Nov. 7-10, 2006, 1 page.

Desai, N. et al. (Jun. 2009). "SPARC Expression Correlates With Tumor Response to Albumin-Bound Paclitaxel in Head and Neck Cancer Patients," *Translational Oncology* 2(2):59-64.

De Vos, A. I. et al. (Nov. 1997). "Differential Modulation of Cisplatin Accumulation in Leukocytes and Tumor Cell Lines by the Paclitaxel Vehicle Cremophor EL," *Ann. Onc.* 8(11):1145-1150.

Du Bois, A. et al. (1997). "Phase I/II Study of the Combination of Carboplatin and Paclitaxel as First-line Chemotherapy in Patients with Advanced Epithelial Ovarian Cancer," *Ann. Oncol.* 8:355-361.

(56) References Cited

OTHER PUBLICATIONS

Di Costanzo, F. et al. (2009). "Targeted Delivery of Albumin Bound Paclitaxel in the Treatment of Advanced Breast Cancer," *OncoTargets and Therapy* 2:179-188.

Dubey, S. et al. (Feb. 2004). "Chemotherapy for Advanced Non-Small Cell Lung Cancer," *Hematol. Oncol. Clin. N. Am.* 18(1):101-114.

Edge, S. B. (eds) et al. (2010). "Lung (Carcinoid Tumors are Included. Sarcomas and Other Rare Tumors are not included)," in Chapter 25 in *AJCC Cancer Staging Manual*, Seventh Edition, American Joint Committee on Cancer, Springer, Chicago, IL, pp. 253-270.

Ellerby, H. M. et al. (Sep. 1999). "Anti-Cancer Activity of Targeted Pro-Apoptotic Peptides," *Nat. Med.* 5(9):1032-1038.

Fehske, K. J. et al. (Jan. 1, 1981). "The Location of Drug Binding Sites in Human Serum Albumin," *Biochemical Pharmacology* 30(7):687-692.

Ficker, E. et al. (Jun. 27, 2003, e-pub. May 29, 2003). "Role of the Cytosolic Chaperones Hsp70 and Hsp90 in Maturation of the Cardiac Potassium Channel hERG," *Circ. Res.* 92:e87-e100.

Ficker, E. et al. (2005). "hERG Channel Trafficking," in *The hERG Cardiac Potassium Channel: Structure, Function and Long QT Syndrome*, Wiley, Chichester, (Novartis Foundation Symposium 266), pp. 57-74, 95-99.

Final Office Action mailed on May 20, 2014, for U.S. Appl. No. 13/073,824, filed Mar. 28, 2011, 11 pages.

Finlayson, J. S. (1980). "Albumin Products," *Seminars in Thrombosis and Hemostasis*, Mammen, E. F. (ed.), Stratton Intercontinental Medical Book Corporation, New York, NY, vol. VI, No. 2, pp. 85-120.

Fleming, G. F. et al. (Jun. 1, 2004). "Phase III Trial of Doxorubicin Plus Cisplatin With or without Paclitaxel Plus Filgrastim in Advanced Endometrial Carcinoma: a Gynecologic Oncology Group Study," *J. Clin. Oncol.* 22(11):2159-2166.

Fossella, F. V. et al. (Mar. 1995). "Phase II Study of Docetaxel for Advanced or Metastatic Platinum-Refractory Non-Small-Cell Lung Cancer," *J. Clin. Oncol.* 13(3):645-651.

Fossella, F. et al. (Aug. 15, 2003). "Randomized, Multinational, Phase III Study of Docetaxel Plus Platinum Combinations Versus Vinorelbine Plus Cisplatin for Advanced Non-Small-Cell Lung Cancer: the TAX 326 Study Group," *J. Clin. Oncol.* 21(16):3016-3024.

Fujimoto-Ouchi, K. et al. (Apr. 2001). "Schedule of Dependency of Antitumor Activity in Combination Therapy with Capecitabine/5'Deoxy-5-Fluorouridine and Docetaxel in Breast Cancer Models," *Clin. Cancer Res.* 7:1079-1086.

Fulfaro F. et al. (Jul. 15, 2004). "Weekly Paclitaxel (T) and Pegylated Liposomal Doxorubicin (PLD) as First Line Treatment in Metastatic Breast Cancer (MBC) Patients," *J. Clin. Oncol.* 22(145):535, Abstract No. 704.

Gatzemeier, U. et al. (Jun. 1995). "Phase II Study With Paclitaxel for the Treatment of Advanced Inoperable Non-Small Cell *Lung Cancer,"* 12(Suppl. 2):S101-S106.

Gatzemeier, U. et al. (Oct. 1, 2000). "Phase III Comparative Study of High-Dose Cisplatin Versus a Combination of Paclitaxel and Cisplatin in Patients With Advanced Non-Small-Cell Lung Cancer," *J. Clin. Oncol.* 18(19):3390-3399.

Gelderblom, H. et al. (2001). "Cremophor EL: The Drawbacks and Advantages of Vehicle Selection for Drug Formulation," *Eur. J. Cancer* 37:1590-1598.

Gelderblom, H. et al. (Apr. 2002). "Influence of Cremophor EL on the Bioavailability of Intraperitoneal Paclitaxel," *Clin. Cancer Res.* 8(4):1237-1241.

Gemzar® (Gemcitabine HCl) for Injection Product Label, (revised May 7, 2007). Description, Eli Lilly and Company, IN 46285, 10 pages.

Gradishar, W. J. et al. (Nov. 1, 2005). "Phase III Trial of Nanoparticle Albumin-Bound Paclitaxel Compared with Polyethylated Castor Oil-Based Paclitaxel in Women With Breast Cancer," *J. Clin. Oncol.* 23(31):7794-7803.

Green, M. R. et al. (Aug. 2006, epub: Jun. 1, 2006). "Abraxane®, a Novel Cremophor®- Free, Albumin-Bound Particle Form of Paclitaxel for the Treatment of Advanced Non-Small-Cell Lung Cancer," *Ann. Oncol.* 17(8):1263-1268.

Grilli, R. et al. (Oct. 1993). "Chemotherapy for Advanced Non-Small-Cell Lung Cancer: How Much Benefit is Enough?" *J. Clin. Oncol.* 11(10):1866-1872.

Hainsworth, J. D. et al. (Jul. 1995). "Paclitaxel by 1-Hour Infusion: An Active Drug in Metastatic Non-Small Cell Lung Cancer," *J. Clin. Oncol.* 13(7):1609-1614.

Halvorsen, T.B. et al. (1989). "Association Between Invasiveness, Inflammatory Reaction, Desmoplasia and Survival in Colorectal Cancer," *J. Clin. Pathol.*, 42:162-166.

Harries, M. et al. (Nov. 1, 2005). "Nanoparticle Albumin-Bound Paclitaxel for Metastatic Breast Cancer," *J. Clin. Oncol.* 23(31):7768-7771.

Hauser, C. J. et al. (Jun. 1980). "Oxygen Transport Responses to Colloids and Crystalloids in Critically Ill Surgical Patients," *Surgery, Gynecology and Obstetrics* 150(6):811-816.

Hawkins, M. J. et al. (Jun. 20, 2006). "Dose Escalation Study of *Nab*-Paclitaxel Followed by Carboplatin as First Line Therapy in Advanced Non-Small Cell Lung Cancer (NSCLC)," Abstract from the *2006 ASCO Annual Meeting Proceedings*, Part 1, *J. Clin. Oncol.* 24(18 Suppl.): Abstract No. 7132 located at http://www.asco.org/portal/site/ASCO/template.RAW/menuitem . . . >, last visited on Oct. 1, 2008, 2 pages.

Hawkins, M. J. et a. (Jun. 20, 2007). "Study of Three Weekly *Nab*-Paclitaxel Regimens in Combination With Carboplatin as First-Line Therapy in Advanced Non-Small Cell Lung Cancer (NSCLC)," Abstract from the 2007 ASCO Annual Meeting Proceedings, Part 1, Supplement to *J. Clin. Oncol.* 25(18 Suppl.): Abstract No. 7659 now relocated at http://www.asco.org/ascov2/Meetings/Abstracts?&vmview=abst_detail_view&confID=47 &abstractID=34198, p. 424s, 2 pages.

Hawkins, M. J. et al. (Sep. 2007). "High-Dose 130-Nanometer Albumin-Bound Paclitaxel in Combination with Carboplatin as First-Line Therapy in Advanced Non-Small Cell Lung Cancer," Poster No. 6563, *Eur. J. Cancer Supplements* 5(4):376-377.

He, X. M. et al. (Jul. 16, 1992). "Atomic Structure and Chemistry of Human Serum Albumin," *Nature* 358(6383):209-215.

Heinemann, V. et al. (Aug. 20, 2006). "Randomized Phase III Trial of Gemcitabine Plus Cisplatin Compared with Gemcitabine Alone in Advanced Pancreatic Cancer," *J. Clin. Oncol.* 24(24):3946-3952.

Herbst, R. S. et al. (Mar. 1, 2004). "Gefitinib in Combination With Paclitaxel and Carboplatin in Advanced Non-Small-Cell Lung Cancer: A Phase III Trial—INTACT 2," *J. Clin. Oncol.* 22(5):785-794.

Herrmann, R. et al. (Jun. 1, 2007). "Gemcitabine Plus Capecitabine Compared with Gemcitabine Alone in Advanced Pancreatic Cancer: A Randomized, Multicenter, Phase III Trial of the Swiss Group for Clinical Cancer Research and the Central European Cooperative Oncology Group," *J. Clin. Oncol.* 25(16):2212-2217.

Hudis, C. et al. (Jan. 1999). "Sequential Dose-Dense Doxorubicin, Paclitaxel, and Cyclophosphamide for Resectable High-Risk Breast Cancer: Feasibility and Efficacy," *J. Clin. Oncol.* 17(1):93-100.

Hudis, C. (Aug. 20, 2005). "Testing Chemotherapy for Breast Cancer: Timing is Everything," *J. Clin. Oncol.* 23(24):5434-5436.

Ibrahim, N. K. et al. (May 2002). "Phase I and Pharmacokinetic Study of ABI-007, a Cremophor-Free, Protein-Stabilized, Nanoparticle Formulation of Paclitaxel," *Clin. Cancer Res.* 8:1038-1044.

Ibrahim, N. K. et al. (Sep. 1, 2005). "Multicenter Phase II Trial of ABI-007, an Albumin-Bound Paclitaxel, in Women With Metastatic Breast Cancer," *J. Clin. Oncol.* 23(25):6019-6026.

Ito, T. et al. (2009). "Low podoplanin expression of tumor cells predicts poor prognosis in pathological stage IB squamous cell carcinoma of the lung, tissue microarray analysis of 136 patients using 24 antibodies", *Lung Cancer*, 63:418-424.

Jafar, N. et al. (Apr. 19, 2010). "Caveolin-1 Inhibits Survivin and Increases Sensitivity to Paclitaxel in Breast Cancer Cells," Abstract from the *AACR 101st Annual Meeting 2010*, Meeting held on Monday, Apr. 19, 2010, in Washington D.C., Poster Section 23, Poster Board No. 4, Abstract 2547, one page.

(56) References Cited

OTHER PUBLICATIONS

Jimenez, J. J. et al. (Jan. 15, 1992). "Protection from 1-β-D-Arabinofuranosylcytosine-Induced Alopecia by Epidermal Growth Factor and Fibroblast Growth Factor in the Rat Model," *Cancer Res.* 52(2):413-415.

Johnson, D. H. et al. (Jul. 1996). "Paclitaxel Plus Carboplatin in Advanced Non-Small-Cell Lung Cancer: A Phase II Trial," *J. Clin. Oncol.* 14(7):2054-2060.

Jones, C. M. et al. (Oct. 18, 2007). "Targeted Therapies for NSCLC," from *US Pharm.* 32(10):5-13, full article located at http://www.uspharmacist.com/content/t/oncology/c/10219/, last visited on Nov. 11, 2010, 9 pages.

Jones, V. et al. (2000). "Phase II Study of Weekly Paclitaxel (Taxol) and Liposomal Doxorubicin (Doxil) in Patients with Locally Advanced and Metastatic Breast Cancer," Abstract from the *36th ASCO Annual Meeting Proceedings*, held in New Orleans, Louisiana, on May 20-23, 2000, *Proc. Amer. Soc. Clin. Oncol.* 19:116a, Abstract No. 451.

Keedy, V. L. et al. (May 20, 2010). "A Phase I Study of Nab-Paclitaxel (Nab-P) With Carboplatin (C) and Thoracic Radiation (TR) in Patients With Locally Advanced NSCLC," Abstract from the *2010 ASCO Annual Meeting Proceedings*, held in Chicago, IL, on Jun. 4-8, 2010, published in the *Supplement to J. Clin. Oncol.* vol. 28, No. 15S, Part I of II, and also located at http://www.asco.org/ascov2/Meetings/Abstracts?&vmview=abst_detail_view&confID=74&abstractID=48407, Abstract No. e17504, 5 pages.

Kelly, W. K. et al. (Apr. 1993). "Prostate-Specific Antigen as a Measure of Disease Outcome in Metastatic Hormone-Refractory Prostate Cancer," *J. Clin. Oncol.* 11(4):607-615.

Kelly, K. et al. (Jul. 1, 2001). "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial," *J. Clin. Oncol.* 19(13):3210-3218.

Kim, B. Y. S. et al. (Dec. 16, 2010). "Nanomedicine," *N. Eng. J. Med.* 363(25):2434-2443.

Kim, S.-O. et al. (2005). "Superior Antitumor Efficacy of Genexol®-PM, a Biodegradable Polymeric Micelle-Based Formulation of Paclitaxel (Genexol®) Compared with Gemzar® (Gemcitabine) and Taxol® in Human Pancreatic Cancer Cells in Vitro and in Vivo," Experimental and Molecular Therapeutics 10: Drug Targeting, *Proc. Amer. Assoc. Cancer Res.*, vol. 46, Abstract No. 1440, 2 pages, located at http://www.aacrmeetingabstracts.org/cgi/content/abstract/2005/1/337-b, last visited on Feb. 22, 2010.

Kim, Y.-N. et al. (2002). "Caveolin-1 Phosphorylation in Human Squamous and Epidermoid Carcinoma Cells: Dependence on ErbB1 Expression and Src Activation," *Exp.Cell Res.* 280:134-147.

Klement, G. et al. (Jan. 2002). "Differences in Therapeutic Indexes of Combination Metronomic Chemotherapy and an Anti-VEGFR-2 Antibody in Multidrug-Resistant Human Breast Cancer Xenografts," *Clin. Cancer. Res.* 8(1):221-232.

Ko, A. et al. (2005, e-pub: Jul. 5, 2005). "Serum CA19-9 Response as a Surrogate for Clinical Outcome in Patients Receiving Fixed-Dose Rate Gemcitabine for Advanced Pancreatic Cancer," *British Journal of Cancer* 93:195-199.

Kolodgie, F. D. et al. (Sep. 3, 2002, epub: Aug. 19, 2002). "Sustained Reduction of in-Stent Neointimal Growth With the Use of a Novel Systemic Nanoparticle Paclitaxel," *Circulation* 106(10):1195-1198.

Kondrateva, A. P. (2001). The Combination of Radiation and Drug Therapies for the Organ Safe Treating of Malignant Tumors, *Modern Oncology* 3(3), located at http://www.consilium-medicum.com/magazines/cm/pediatrics/article/8403, in Russian, with English translation (author translated as A. P. Kondratieff) (from translategoogle.com), 6 pages total.

Korn E.L. et al. (2011). "Overall Survival as the Outcome for Randomized Clinical Trials With Effective Subsequent Therapies", *J. Clin. Oncol.*, 29:2439-2442.

Kosmidis, P. et al. (Sep. 1, 2002). "Paclitaxel Plus Carboplatin Versus Gemcitabine Plus Paclitaxel in Advanced Non-Small-Cell Lung Cancer: A Phase III Randomized Trial," *J. Clin. Oncol.* 20(17):3578-3585.

Koukourakis, M. I. et al. (Sep. 1, 2003, epub: Sep. 18, 2003). "Enhanced Expression of SPARC/Osteonectin in the Tumor-Associated Stroma of Non-Small Cell Lung Cancer Is Correlated With Markers of Hypoxia/Acidity and With Poor Prognosis of Patients," *Cancer Res.* 63(17):5376-5380.

Langer, C. J. et al. (Aug. 1995). "Paclitaxel by 24- or 1-Hour Infusion in Combination with Carboplatin in Advanced Non-Small Cell Lung Cancer: The Fox Chase Cancer Center Experience," *Semin. Oncol.* 22(4-Suppl. 9):18-29.

Langer, C. J. et al. (Dec. 1996). "Combination Paclitaxel (1-Hour) and Carboplatin (AUC 7.5) in Advanced Non-Small Cell Lung Cancer: A Phase II Study by the Fox Chase Cancer Center Network," *Semin. Oncol.* 23(6-Suppl. 16):35-41.

Langer, C. J. et al. (Jun. 2008). "Phase III Trial Comparing Paclitaxel Poliglumex (CT-2103, PPX) in Combination with Carboplatin Versus Standard Paclitaxel and Carboplatin in the Treatment of PS 2 Patients with Chemotherapy-Naïve Advanced Non-Small Cell Lung Cancer," *J. Thorac. Oncol.* 3(6):623-630.

Le Chevalier, T. et al. (Feb. 1994). "Randomized Study of Vinorelbine and Cisplatin Versus Vindesine and Cisplatin versus Vinorelbine Alone in Advanced Non-Small-Cell Lung Cancer: Results of a European Multicenter Trial Including 612 Patients," *J. Clin. Oncol.* 12(2):360-367.

Leong, S.-S. et al. (Feb. 1, 2005, epub: Dec. 20, 2004). "Paclitaxel, Carboplatin, and Gemcitabine in Metastatic Nasopharyngeal Carcinoma: A Phase II Trial Using a Triplet Combination," *Cancer* 103(3):569-575.

Levine, M. N. et al. (Published Ahead of Print on Apr. 30, 2012). "Method to Our Madness or Madness in Our Method? Pitfalls in Trial Methodology,"*J. Clin. Oncol.* vol. 30, 3 pages.

Li, C. et al. (Jun. 1, 1998). "Complete Regression of Well-Established Tumors Using a Novel water-Soluble Poly(L-Glutamic Acid)-Paclitaxel Conjugate," *Cancer Research* 58:2404-2409.

Li, C. et al. (Jul. 2000). "Tumor Irradiation Enhances the Tumor-Specific Distribution of Poly(L-Glutamic Acid)-Conjugated Paclitaxel and Its Antitumor Efficacy," *Clin. Cancer Res.* 6(7):2829-2834.

Li, C. et al. (May 22, 2008). "Polymer-Drug Conjugates: Recent Development in Clinical Oncology," *Adv. Drug Deliv. Rev.* 60(8):886-898, 24 pages.

Lilenbaum, R. C. et al. (2002). "Single-Agent (SA) Versus Combination Chemotherapy (CC) in Advanced Non-Small Cell Lung Cancer (NSCLC): A CALGB Randomized Trial of Efficacy, Quality of Life (QOL), and Cost-Effectiveness," *Proc. Am. Soc. Clin. Oncol.* Abstract presented at the *2002 ASCO Annual Meeting Proceeding*, relocated at http://jco.ascopubs.org/content/23/1/190.full, Jun. 2002, vol. 21, Abstract No. 2, 2 pages.

Loehr, M. et al. (2009). "Cationic Liposomal Paclitaxel in Combination with Gemcitabine in Patients with Advanced Pancreatic Cancer: A Phase II Trial," Abstract presented at the *2009 ASCO Annual Meeting Proceedings* (Post-Meeting Edition), published in *J. Clin. Oncol.* vol. 27, No. 15S, May 20 Supplement, Abstract No. 4526, located http://meeting.ascopubs.org/cgi/content/abstract/27/15S/4526, last visited on Feb. 22, 2010, 2 pges.

Lorenz, W. et al. (Mar. 1977). "Histamine Release in Dogs by Cremophor El® and Its Derivatives: Oxethylated Oleic Acid is the Most Effective Constituent," *Agents and Actions* 7(1):63-67.

Louvet, C. et al. (Mar. 15, 2002). "Gemcitabine combined With Oxaliplatin in Advanced Pancreatic Adenocarcinoma: Final Results of a GERCOR Multicenter Phase II Study," *J. Clin. Oncol.* 20(6):1512-1518.

Louvet, C. et al. (May 20, 2005). "Gemcitabine in Combination with Oxaliplatin Compared with Gemcitabine Alone in Locally Advanced or Metastatic Pancreatic Cancer: Results of a GERCOR and GISCAD Phase III Trial," *J. Clin. Oncol.* 23(15):3509-3516.

Lowry, F. (Nov. 2008). "Drug Combo Shrinks Pancreatic Tumors in Phase I Trial," *GI & Hepatology News*, p. 14.

(56) References Cited

OTHER PUBLICATIONS

Lynch, T. Jr. et al. (2005). "Optimizing Chemotherapy and Targeted Agent Combinations in NSCLC," *Lung Cancer* 50 (Suppl. 2):S25-S32.
Lynch, T. J. et al. (Feb. 20, 2010, epub: Jan. 25, 2010). "Cetuximab and First-Line Taxane/Carboplatin Chemotherapy in Advanced Non-Small-Cell Lung Cancer: Results of the Randomized Multicenter Phase III Trial BMS099," *J. Clin. Oncol.* 28(6):911-917.
Mahadevan, D. et al. (Apr. 2007, e-pub. Apr. 3, 2007). "Tumor-stroma interactions in pancreatic ductal adenocarcinoma," *Mol. Cancer Ther.*, 6(4):1186-1197.
Maitra, A. et al. (Dec. 10, 2009). "Abstract C246: nab®-Paclitaxel Targets Tumor Stroma and Results, Combined with Gemcitabine, in High Efficacy Against Pancreatic Cancer Models," *Molecular Cancer Therapeutics* 8 (Meeting Abstract Supplement), C246, Abstract presented at the *AACR-NCI-EORTC International Conference on Molecular Targets and Cancer Therapeutics*, held on Nov. 15-19, 2009, Boston, MA, abstract located at http://mct.aacrjournals.org/cgi/content/meeting_abstract/8/12_MeetingAbstracts/C246?sid=2cd1379d-eb9e-4215-94ed-b34b968c25ec, last visited on Feb. 22, 2010, 2 pages.
Mavroudis, D. et al. (2002). "Phase I Study of Paclitaxel (Taxol) and Pegylated Liposomal Doxorubicin (Caelyx) Administered Every 2 Weeks in Patients with Advanced Solid Tumors," *Oncology* 62:216-222.
McKeage, M.J. et al. (2010). "Comparative outcomes of squamous and non-squamous non-small cell lung cancer (NSCLC) patients in phase II studies of ASA404 (DMXAA)—retrospective analysis of pooled data", *J. Thorac. Dis.*, 2:199-204.
Micha, J. P. et al. (Feb. 2006, e-pub: Oct. 14, 2005). "Abraxane in the Treatment of Ovarian Cancer: the Absence of Hypersensitivity Reactions," *Gynecol. Oncol.* 100(2):437-438, 2 pages.
Modiano, M. et al. (1999). "Phase I Study of DOXIL® (Pegylated Liposomal Doxorubicin) Plus Escalating Doses of TAXOL® in the Treatment of Patients with Advanced Breast or Gynecologic Malignancies," *Proc. Amer. Soc. Clin. Oncol.*18:220a, Abstract No. 848, 3 pages.
Mondesire, W. H. et al. (Oct. 15, 2004, epub: Oct. 22, 2004). "Targeting Mammalian Target of Rapamycin Synergistically Enhances Chemotherapy-Induced Cytotoxicity in Breast Cancer Cells," *Clin. Cancer Res.* 10(20):7031-7042.
Moore, M. J. et al. (May 20, 2007). "Erlotinib Plus Gemcitabine Compared with Gemcitabine Alone in Patients with Advanced Pancreatic Cancer: A Phase III Trial of the National Cancer Institute of Canada Clinical Trials Group," *J. Clin.Oncol.* 25(15):1960-1966.
Moreno-Aspitia, A. et al. (2005). "Nanoparticle Albumin-bound Paclitaxel (ABI-007): A Newer Taxane Alternative in Breast Cancer," *Future Oncol.* 1(6):755-762.
Moreno-Aspitia, A. et al. (Oct. 2005). "North Central Cancer Treatment Group N0531: Phase II Trial of Weekly Albumin-Bound Paclitaxel (ABI-007, Abraxane® in Combination with Gemcitabine in Patients with Metastatic Breast Cancer," *Clinical Breast Cancer* 6(4):361-364.
Muraoka N. et al. (2008). "Apparent Diffusion Coefficient in Pancreatic Cancer: Characterization and Histopathological Correlations," *Journal of Magnetic Resonance Imaging* 27:1302-1308.
Nasu, Y. et al. (Sep. 1998). "Suppression of Caveolin Expression Induces Androgen Sensitivity in Metastatic Androgen-Insensitive Mouse Prostate Cancer Cells," *Nat. Med.* 4(9):1062-1064.
National Cancer Institute (Aug. 11, 2009). "A Phase I/II Study of Nab-Paclitaxel & Carboplatin with Concurrent Radiation Therapy for Unresectable Stage III Non-Small Cell Lung Cancer", Located at https://clinicaltrials.gov/archive/NCT00544648/2009_08_11, ClinicalTrials.gov Identifier: NCT00544648, last updated Aug. 11, 2009, last visited Jan. 22, 2015, 4 pages.
Neesse, A. et al. (Jun. 2011, e-pub. Oct. 21, 2010). "Stromal Biology and Therapy in Pancreatic Cancer," *Gut.* 60(6):861-866.
Ng, S. S. W. et al. (Feb. 1, 2004, e-pub: Feb. 10, 2004). "Taxane-Mediated Antiangiogenesis in Vitro: Influence of Formulation Vehicles and Binding Proteins," *Cancer Res.* 64:821-824.

Nieto, J. et al. (2008). "Metastatic Pancreatic Cancer 2008: Is the Glass Less Empty?" *The Oncologist* 13:562-576.
Non-Final Office Action mailed on Feb. 13, 2014, for U.S. Appl. No. 13/781,479, filed Feb. 28, 2013, 39 pages.
Novelos Therapeutics, Inc. (2010). "NOV-002, Cancer," located at http://www.novelos.com/html/our_products/BAM_002.htm, last visited on May 6, 2010, 4 pages.
Nugent W.C. et al. (1997). "Non-Small Cell Lung Cancer at the Extremes of Age: Impact on Diagnosis and Treatment", *Ann. Thorac. Surg.*, 63:193-7.
Nyman, D. W. et al. (Nov. 1, 2005). "Phase I and Pharmacokinetics Trial of ABI-007, a Novel Nanoparticle Formulation of Paclitaxel in Patients with Advanced Nonhematologic Malignancies," *J. Clin. Oncol.* 23(31):7785-7793.
Oettle, H. et al. (Oct. 2005, epub: Aug. 8, 2005). "A Phase III Trial of Pemetrexed Plus Gemcitabine Versus Gemcitabine in Patients With Unresectable or Metastatic Pancreatic Cancer," *Annals of Oncology*, 16(10):1639-1645.
Onn, A. et al. (2004). "Treatment of Non-Small-Cell Lung Cancer: A Perspective on the Recent Advances and the Experience with Gefitinib," *Br. J. Cancer* 91(Supp) 2):S11-S17.
O'Reilly, M. S. et al. (Oct. 21, 1994). "Angiostatin: A Novel Angiogenesis Inhibitor That Mediates the Suppression of Metastases by a Lewis Lung Carcinoma," *Cell* 79(2):315-328.
O'Reilly, M. S. et al. (Jan. 24, 1997). "Endostatin: An Endogenous Inhibitor of Angiogenesis and Tumor Growth," *Cell*88(2):277-285.
O'Shaughnessy, J. A. et al. (2004). "Weekly Nanoparticle Albumin Paclitaxel (Abraxane) Results in Long-Term Disease Control in Patients With Taxane-Refractory Metastatic Breast Cancer," *Breast Cancer Research and Treatment, 27th Annual Charles A. Coltman San Antonio Breast Cancer Symposium*, San Antonio, Texas, Dec. 8-11, 2004, 88(Suppl. 1):S65, Abstract No. 1070.
Paál, K. et al. (2001). "High Affinity Binding of Paclitaxel to Human Serum Albumin," *Eur. J. Biochem.* 268(7):2187-2191.
Paccagnella, A. et al. (Dec. 1996). "Paclitaxel and Carboplatin: A Phase I Study in Advanced Non-Small Cell Lung Cancer," *Semin. Oncol.* 23(6)(Suppl. 16):76-79.
Papyan, A. et al. (2004). "MBT-0206 Enhances the Anti-Tumor Treatment in a Highly Metastatic Human Pancreatic Cancer Mouse Model," *Proc. Amer. Assoc. Cancer Res.* vol. 45, Cellular, Molecular, and Tumor Biology 80: Angiogenesis Inhibitors III, Abstract No. 4104, located at http://aacrmeetingabstracts.org/cgi/content/abstract/2004/1/947-c, last visited Feb. 22, 2010, 2 pages.
Pectasides, D. et al. (2005). "Comparison of Docetaxel and Docetaxel-Irinotecan Combination as Second-Line Chemotherapy in Advanced Non-Small-Cell Lung Cancer: A Randomized Phase II Trial," Annals of Oncology 16:294-299.
Perabo, F. G. et al. (Nov.-Dec. 2003). "Preclinical Evaluation of Gemcitabine/Paclitaxel-Interactions in Human Bladder Cancer Lines," *Anticancer Res.* 23(6C):4805-4814, Abstract only located at http://www.ncbi.nlm.nih.gov/pubmed/14981929, last visited on Jan. 11, 2010, one page.
Pirker, R. et al. (May 2, 2009). "Cetuximab Plus Chemotherapy in Patients with Advanced Non-Small-Cell Lung Cancer (FLEX): An Open-Label Randomised Phase III Trial," *Lancet* 373:1525-1531.
Porter, P. L. et al. (Aug. 1995). "Distribution of SPARC in Normal and Neoplastic Human Tissue," *J. Histochem. and Cytochem.* 43(8):791-800.
Raspaglio, G. et al. (Jan. 1, 2005). "Thiocolchicine Dimers: A Novel Class of Topoisomerase-I Inhibitors," *Biochem. Pharmacol.* 69(1):113-121, Abstract only located at http://www.ncbi.nlm.nih.gov/pubmed/15588720, last visited on Jan. 11, 2010, one page.
Reynolds, C. et al. (Jun. 20, 2007). "An Open-Label, Phase II Trial of Nanoparticle Albumin Bound Paclitaxel (Nab-paclitaxel), Carboplatin, and Bevacizumab in First-Line Patients with Advanced Non-squamous Non-Small Cell Lung Cancer (NSCLC)," Abstract from the *2007 ASCO Annual Meeting Proceedings, Part 1, J. Clin. Oncol.* 25(18 Suppl.): Abstract No. 7610, located at http://www.asco.org/portal/site/ASCO/template.RAW/menuitem . . . , last visited on Oct. 1, 2008, two pages.
Reynolds, C. et al. (Dec. 2009). "Phase II Trial of Nanoparticle Albumin-Bound Paclitaxel, Carboplatin, and Bevacizumab in First-

(56) References Cited

OTHER PUBLICATIONS

Line Patients With Advanced Nonsquamous Non-Small Cell Lung Cancer," *J. Thoracic Oncol.* 4(12):1537-1543.
Rigas, J. R. (Jun. 2, 2004). "Taxane-Platinum Combinations in Advanced Non-Small Cell Lung Cancer: A Review," *The Oncologist* 9(Suppl. 2):16-23.
Rizvi, N. A. et al. (Jun. 20, 2006). "Phase I/II Study of ABI-007 as First Line Chemotherapy in Advanced Non-Small Cell Lung Cancer (NSCLC)," *J. Clin. Oncol. 2006 ASCO Annual Meeting Proceedings* Part I, vol. 24, No. 18S, (Jun. 20 Supplement), Abstract located at http://www.asco.org/ascov2/Meetings/Abstracts?&vmview=abst_detail_view&confID=40&abstractID=32992, last visited on Jul. 18, 2012, Abstract No. 7105, 3 pages.
Rizvi, N. A. et al. (Feb. 1, 2008). "Phase I/II Trial of Weekly Intravenous 130-nm Albumin-Bound Paclitaxel as Initial Chemotherapy in Patients with Stage IV Non-Small-Cell Lung Cancer," *J. Clin. Oncol.* 26(4):639-643.
Robert, N. et al. (Dec. 2005). "Pilot Study of Dose Dense Doxorubicin Plus Cyclophosphamide Followed by ABI-007 in Patients with Early Stage Breast Cancer," *Breast Cancer Research and Treatment, Special Issue from the 28th Annual San Antonio Breast Cancer Symposium*, San Antonio, TX, Dec. 8-11, 2005, Abstract—Poster Session II, p. S109, Abstract No. 2073, 3 pages.
Rocha-Lima, C. M. et al. (Sep. 15, 2004). "Irinotecan Plus Gemcitabine Results in no Survival Advantage Compared with Gemcitabine Monotherapy in Patients with Locally Advanced or Metastatic Pancreatic Cancer Despite Increased Tumor Response Rate," *J. Clin. Oncol.* 22(18):3776-3783.
Roche Laboratories, Inc. (Apr. 2006). "Xeloda® (Capecitabine) Tablets Product Insert," 43 pages.
Roe, S. M. et al. (Jan. 28, 1999, e-pub: Jan. 9, 1999). "Structural Basis for Inhibition of the Hsp90 Molecular Chaperone by the Antitumor Antibiotics Radicicol and Geldanamycin," *J. Med. Chem.* 42(2):260-266.
Romond, E. H. et al. (2005). "Combined Analysis of NSABP-B-31 and NCCTG-N9381: Disease-Free and Overall Survival Data," *Breast Cancer Update* 4(6):15-19.
Rosell, R. et al. (2002). "Phase III Randomised Trial Comparing Paclitaxel/Carboplatin with Paclitaxel/Cisplatin in Patients with Advanced Non-Small-Cell Lung Cancer: A Cooperative Multinational Trial," *Ann. Oncol.* 13:1539-1549.
Safran, H. et al. (Sep. 1, 2002). "Gemcitabine, Paclitaxel, and Radiation for Locally Advanced Pancreatic Cancer: A Phase I Trial," *Int. J. Radiation Oncol. Biol. Phys.* 54(1):137-141.
Sandler, A. B. et al. (Jan. 2000). "Phase III Trial of Gemcitabine Plus Cisplatin Versus Cisplatin Alone in Patients with Locally Advanced or Metastatic Non-Small-Cell Lung Cancer," *J. Clin. Oncol.* 18(1):122-130.
Sandler, A. et al. (Dec. 14, 2006). "Paclitaxel-Carboplatin Alone or With Bevacizumab for Non-Small-Cell Lung Cancer," *New Eng. J. Med.* 355(24):2542-2550.
Sausville, E. A. et al. (Oct. 2003). "Clinical Development of 17-Allylamino, 17-Demethoxygeldanamycin," *Curr. Cancer Drug Targets* 3(5):377-383, Abstract only located at http:www.ncbi.nlm.nih.gov/pubmed/14529389, last visited on Jan. 28, 2010, one page.
Sawada, N. et al. (Apr. 1998). "Induction of Thymidine Phosphorylase Activity and Enhancement of Capecitabine Efficacy by Taxol/Taxotere in Human Cancer Xenografts," *Clinical Cancer Res.* 4(4):1013-1019.
Scagliotti, G. V. et al. (Nov. 1, 2002). "Phase III Randomized Trial Comparing Three Platinum-Based Doublets in Advanced Non-Small-Cell Lung Cancer," *J. Clin. Oncol.* 20(21):4285-4291.
Scagliotti, G. V. et al. (Jul. 20, 2008, e-pub: May 27, 2008). "Phase III Study Comparing Cisplatin Plus Gemcitabine with Cisplatin Plus Pemetrexed in Chemotherapy-Naïve Patients with Advanced-Stage Non-Small-Cell Lung Cancer," *J. Clin. Oncol.* 26(21):3543-3551.
Schiller, J. H. et al., (Jan. 10, 2002). "Comparison of Four Chemotherapy Regimens for Advanced Non-Small-Cell Lung Cancer," *New England J. Med.* 346(2):92-98.

Schilsky, R. L. et al. (Jan. 15, 2002). "Dose-Escalating Study of Capecitabine Plus Gemcitabine Combination Therapy in Patients with Advanced Cancer," *J. Clin. Oncol.* 20(2):582-587.
Schnitzer, J. E. (Jan. 1992). "Gp60 is an Albumin-Binding Glycoprotein Expressed by Continuous Endothelium Involved in Albumin Transcytosis," *Am. J. Physiol.* 262(1, Pt. 2):H246-H254.
Schwonzen, M. et al. (Oct. 2000). "Liposomal Doxorubicin and Weekly Paclitaxel in the Treatment of Metastatic Breast Cancer," *Anti-Cancer Drugs* 11(9):681-685.
Seidman, A. D. et al. (1993). "Taxol Plus Recombinant Human Granulocyte-Colony Stimulating Factor as Initial and as Salvage Chemotherapy for Metastatic Breast Cancer: A Preliminary Report," *Monogr. Natl. Cancer Inst.* (15):171-175.
Shaked, Y. et al. (Jan. 2005). "Genetic Heterogeneity of the Vasculogenic Phenotype Parallels Angiogenesis: Implications for Cellular Surrogate Marker Analysis of Antiangiogenesis," *Cancer Cell* 7:101-111.
Shepherd, F. A. et al. (Dec. 1995). "Phase II Trials of Single-Agent Activity of Gemcitabine in Patients With Advanced Non-Small Cell Lung Cancer: An Overview," *Anti-Cancer Drugs* 6(Suppl. 6):19-25.
Shi, Q. et al. (Dec. 1997). "Antitumor Agents—CLXXV. Anti-Tubulin Action of (+)-Thiocolchicine Prepared by Partial Synthesis," *Bioorg. Med. Chem.* 5(12):2277-2282, Abstract only located at http://www.ncib.nlm.nih.gov/pubmed/9459025, last visited on Jan. 11, 2010, one page.
Sledge, G. W. et al. (Feb. 15, 2003). "Phase III Trial of Doxorubicin, Paclitaxel, and the Combination of Doxorubicin and Paclitaxel as Front-line Chemotherapy for Metastatic Breast Cancer: an Intergroup Trial (E1193)," *J. Clin. Oncol.* 21(4):588-592.
Smith, L.S. et al. (May 20, 2008, supplement). "SPARC and CA 19-9 as Biomarkers in Patients with Advanced Pancreatic Cancer Treated with Nab Paclitaxel Plus Gemcitabine," *J. Clinical Oncology* 2008 ASCO Annual Meeting Proceedings 26(15S):15592, two pages only.
Socinski, M. (Oct. 2006). "Update on Nanoparticle Albumin-Bound Paclitaxel," *Clinical Advances in Hematology & Oncology* 4(10):745-746.
Socinski, M. A. et al. (Aug. 1, 2009). "PD3.3.4—Retrospective Analysis of a Phase II Study of *nab*-Paclitaxel plus Carboplatin in Advanced NSCLC: Response Based on Histology," Abstract presented at the 13th World Conference on Lung Cancer, held in San Francisco, CA, on Jul. 31-Aug. 4, 2009, and located at www.2009worldlungcancer.org, under *NSCLC—Advanced Disease I, organized by the International Association for the Study of Lung Cancer*, 2 pages (Abstract).
Socinski, M. A. et al. (Aug. 1, 2009). "PD3.3.4—Retrospective Analysis of a Phase II Study of *nab*-Paclitaxel plus Carboplatin in Advanced NSCLC: Response Based on Histology," Poster—Discussion presented as an Abstract at the 13th World Conference on Lung Cancer, held in San Francisco, CA, on Jul. 31-Aug. 4, 2009, under *NSCLC—Advanced Disease I, organized by the International Association for the Study of Lung Cancer*, 9 pages (Poster).
Socinski, M. A. et al. (Jun. 2010). "A Dose Finding Study of Weekly and Every-3-Week *Nab*-Paclitaxel Followed by Carboplatin as First-Line Therapy in Patients With Advanced Non-Small Cell Lung Cancer," *J. Thoracic Oncol.* 5(6):852-861.
Socinski, M. A. et al. (May 20, 2010). "Results of Randomized, Phase III Trial of Nab-Paclitaxel (Nab-P) and Carboplatin (C) Compared With Cremophor-Based Paclitaxel (P) and Carboplatin as First-Line Therapy in Advanced Non-Small Cell Lung Cancer (NSCLC)," Abstract from the 2010 ASCO Annual Meeting, under Abstract No. LBA 7511, published in *Supplement to J. Cin. Oncol.* 28(18S): Abstract No. LBA 7511, p. 541s, abstract also available at http://www.asco.org/ascov2/Meetings/Abstracts?&vmview=abst_detail_view&confID=74&abstr actID=52889, last visited on Jul. 18, 2012, 4 pages.
Socinski, M. A. et al. (Published Ahead of Print on Apr. 30, 2012). "Weekly *nab* Paclitaxel in Combination With Carboplatin Versus Solvent-Based Paclitaxel Plus Carboplatin as First-Line Therapy in Patients With Advanced Non-Small-Lung Cancer: Final Results of a Final Phase III Trial," *J. Clin. Oncol.* 8 pages.

(56) References Cited

OTHER PUBLICATIONS

Socinski M.A. et al. (2013). "Safety and efficacy of weekly nab®-paclitaxel in combination with carboplatin as first-line therapy in elderly patients with advanced non-small-cell lung cancer", *Annals of Oncology*, 24:314-321.

Sørensen, J. B. et al. (Mar. 1987). "Vince Alkaloids in the Treatment of Non-Small Cell Lung Cancer," *Cancer Treatment Reviews* 14(1):29-51.

Sørensen, J. B. (Apr. 1995). "Gemcitabine in Non-Small Cell Lung Cancer," *Lung Cancer* 12(Suppl. 1):S173-S175.

Souquet, P. J. et al. (Jul. 3, 1993). "Polychemotherapy in Advanced Non Small Cell Lung Cancer: A Meta-Analysis," *Lancet* 342(8862):19-21.

Sparreboom, A. et al. (Apr. 1, 1999). "Cremophor EL-Mediated Alteration of Paclitaxel Distribution in Human Blood: Clinical Pharmacokinetic Implications," *Cancer Res.* 59(7):1454-1457.

Sparreboom, A. et al. (Jun. 1, 2005). "Comparative Preclinical and Clinical Pharmacokinetics of a Cremophor-Free, Nanoparticle Albumin-Bound Paclitaxel (ABI-007) and Paclitaxel Formulated in Cremophor (Taxol)," *Clin. Cancer Res.* 11(11):4136-4143.

Stinchcombe, T. E. et al. (2005). "Preliminary Results of Phase I Trial of Carboplatin (CP) in Combination with ABI-007 Administered Weekly or Every 3 Weeks in Patients (pts) With Solid Tumors," Abstract from the *28th Annual San Antonio Breast Cancer Symposium*, held in San Antonio, Texas, USA, on Dec. 8-11, 2005, and published in *Breast Cancer Research and Treatment*, 94(1):S71, Abstract No. 1092, one page.

Stinchcombe, T. E. et al. (Oct. 2007). "Phase I and Pharmacokinetic Trial of Carboplatin and Albumin-Bound Paclitaxel, ABI-007 (Abraxane®) on Three Treatment Schedules in Patients with Solid Tumors," *Cancer Chemotherap. Pharmacol.* 60(5):759-766.

Stinchcombe, T.E. (2007). "Nanoparticle Albumin-Bound Paclitaxel: A Novel Cremphor EL®—Free Formulation of Paclitaxel," *Nanomedicine* 2(4):415-423, two pages (Abstract only.).

Stroyakovsky, D. L. et al. (Aug. 1, 2009). "PD3.4.1—Weekly and Every-3-Week *Nab*-Paclitaxel Followed by Carboplatin as First-Line Therapy is Effective in Patients With Advanced Non-Small Cell Lung Cancer: Final Results of a Phase II Study," Abstract presented at the *13th World Conference on Lung Cancer*, held in San Francisco, CA, on Jul. 31-Aug. 4, 2009, under NSCLC—Advanced Disease I, conference organized by the International Association for the Study of Lung Cancer, abstract located at www.2009worldlungcancer.org, http://abstracts/webges.com/itinerary/itinerary.php?i=1&abstract=2157&keyword=paclitaxel, last visited on Nov. 11, 2010, 2 pages (Abstract).

Stroyakovsky, D. L. et al. (2009). "PD3.4.1—Weekly and Every-3-Week *nab*—Paclitaxel Followed by Carboplatin as First-Line Therapy is Effective in Patients With Advanced Non-Small Cell Lung Cancer: Final Results of a Phase II Study," Poster-Discussion presented at the *13th World Conference on Lung Cancer*, San Francisco, CA, Jul. 31-Aug. 4, 2009, under NSCLC—Advanced Disease I, conference organized by the International Association for the Study of Lung Cancer, 10 pages (Poster).

Sugio, S. et al. (1999). "Crystal Structure of Human Serum Albumin at 2.5 521 Resolution," *Protein Eng.* 12(6):439-446.

Suzuoki et al. (2002). "Impact of Caveolin-1 Expression on Prognosis of Pancreatic Ductal Adenocarcinoma," *British Journal of Cancer* 87(10):1140-1144.

Tahir, S. A. et al. (May 15, 2001). "Secreted Caveolin-1 Stimulates Cell Survival/Clonal Growth and Contributes to Metastasis in Androgen-Insensitive Prostate Cancer," *Cancer Res.* 61(10):3882-3885.

Tahir, S. A. et al. (Sep. 1, 2003, e-pub: Sep. 23, 2003). "Development of an Immunoassay for Serum Caveolin-1: A Novel Biomarker for Prostate Cancer," *Clin. Cancer Res.* 9(10 Pt. 1):3653-3659.

Tannock, I.F. et al. (Oct. 7, 2004). "Docetaxel Plus Prednisone or Mitoxantrone Plus Prednisone for Advanced Prostate Cancer," *New England Journal of Medicine* 351(15):1502-1512.

Tao, C. et al. (2005). "Preparation of Nanoparticle Albumin Bound 17AAG (nab-17AAG) Suitable for Intravenous Administration," *Proc. Amer. Assoc. Cancer Res.* vol. 46, Experimental and Molecular Therapeutics 10: Drug Targeting, Abstract No. 1435, located at http://www.aacrmeetingabstracts.org/cgi/content/abstract/2005/1/336-b, last visited on Jul. 18, 2012, two pages.

Tao, C. et al. (2006). "Preparation and Evaluation of Novel Derivatives of Geldanamycin," Abstract 1121, *Proc. Amer. Assoc. Cancer Res.* vol. 47, Chemistry 2: Drug Discovery 1: Screening, Synthesis, and Structure-Activity Relationships, Abstract No. 1121, located at http://www.aacrmeetingabstracts.org/cgi/content/abstract/2006/1/265, last visited on Jul. 22, 2009, two pages.

TARCEVA® (Erlotinib) Prescribing Product Label Information for Tablets, Oral Administration of TARCEVA® (revised as Apr. 2009). Initial U.S. Approval: 2004, Manufactured for: OSI Pharmaceuticals, Inc. Melville, NY 11747; Manufactured by Schwarz Pharma Manufacturing, Seymour, IN 47274; Distributed by Genentech USA, Inc. CA 94080-4990; Under Section 14 of "Clinical Studies", see specifically Sections Nos. 14.1 entitled "NSCLC—TARCEVA Administered Concurrently with Chemotherapy," and 14.2 entitled "Pancreatic Cancer—TARCEVA Administered Concurrently with Gemcitabine," 4 pages.

Taxol® (2003). Taxol Prescribing Information (Paclitaxel) Injection (Patient Information Included) Package Insert, pp. 1-53.

Ten Tije, A. J. et al. (2003). "Pharmacological Effects of Formulation Vehicles: Implications for Cancer Chemotherapy," *Clin. Pharmacokinet.* 42(7):665-685.

Therasse, P. et al. (Feb. 2, 2000). "New Guidelines to Evaluate the Response to Treatment in Solid Tumors. European Organization for Research and Treatment of Cancer, National Cancer Institute of the United States, National Cancer Institute of Canada," *J. Natl. Cancer Inst.* 92(3):205-216.

Trieu, V. et al. (Apr. 2008). "Cardiovascular and Respiratory Assessment Following IV Administration of Nanoparticle Albumin-Bound 17AAG (nab-17AAG) in Conscious Cynomolgus Monkeys" Abstract presented at the *99th AACR Annual Meeting*, in San Diego, CA, on Apr. 12-16, 2008, Abstract located at http://www.aacrmeetingabstracts.org/cgi/content/meeting_abstract/2008/1_Annual_Meeting/5746?maxtoshow=&hits=10&RESULTFORMAT=&author1=trieu&andorexactfulltext=and&searchid=1&FIRSTINDEX=10&sortspec=relevance&resourcetype=HWCIT, Abstract No. 5746, 2 pages.

Trieu, V. et al. (2008). "Pharmacokinetic and ADME Study of Nanoparticle Albumin-Bound 17AAG (nab-17AAG) in Mice," Pharmacology: Nanoparticles and New Drug Delivery Strategies: Poster, Abstract No. 5747, presented at *99th AACR Annual Meeting*, Apr. 12-16, 2008, San Diego, CA, located at http://www.aacrmeetingabstracts.org/cgi/content/meeting_abstract/2008/1_Annual_Meeting/5747, last visited on Jul. 22, 2009 two pages.

Tsai, J. Y. et al. (Aug. 2003). "Combined Modality Therapy for Pancreatic Cancer," *Seminars in Oncology* 30(4): Suppl. 9, pp. 71-79.

Tullis, J. L. (Jan. 24, 1977). "Albumin. 1. Background and Use," *JAMA* 237(4):355-360.

Tullis, J. L. (Jan. 31, 1977). "Albumin. 2. Guidelines for Clinical Use," *JAMA* 237(5):460-463.

U.S. Department of Health and Human Services et al. (2011). "Guidance for Industry Clinical Trial Endpoints for the Approval of Non-Small Cell Lung Cancer Drugs and Biologics," located at http://www.fda.gov/Drugs/GuidanceComplianceRegulatoryInformation/Guidances/default.htm, 15 pages.

U.S. National Library of Medicine. "MedlinePlus® Lung Cancer—Non-Small Cell," located at <http://www.nlm.nih.gov/medlineplus/ency/article/007194.htm,> last visited on Aug. 29, 2013, 5 pages.

Van Cutsem, E. et al. (Apr. 15, 2004). "Phase III Trial of Gemcitabine Plus Tipifarnib Compared With Gemcitabine Plus Placebo in Advanced Pancreatic Cancer," *J. Clin. Oncology* 22(8):1430-1438.

Vanderbilt-Ingram Cancer Centre (Aug. 11, 2009). "Paclitaxel Albumin-Stabilized Nanoparticle Formulation, Carboplatin, and Radiation Therapy in Treating Patients With Stage III Non-Small-Cell Lung Cancer That Cannot Be Removed by Surgery," Article

(56) References Cited

OTHER PUBLICATIONS located at http://clinicaltrials.gov/archive/NTC00544648/2009_ 08_11, ClinicalTrials.gov Identifier: NCT00544648, study first received on Oct. 13, 2007, last updated on May 3, 2011, with updates, last visited on Jul. 20, 2011, 16 pages.

Van Tellingen, O. et al. (Sep. 1999). "Cremophor EL Causes (Pseudo-) Non-Linear Pharmacokinetics of Paclitaxel in Patients," *Br. J. Cancer* 81(2):330-335.

Vogel, C. (Oct. 1, 2005). "Nab Paclitaxel," *Breast Cancer Update Nurses* 3(2): p. 12.

Von Hoff, D. D. et al. (2009). "SPARC Correlation with Response to Gemcitabine (G) Plus nab-Paclitaxel (nab-P) in Patients with Advanced Metastatic Pancreatic Cancer: A Phase I/II Study," Abstract presented at the *2009 ASCO Annual Meeting*, in Orlando, Florida, on May 29-Jun. 2, 2009, Abstract published in *J. Clin. Oncol.* 27:15s, 2009 (Suppl: Abstract 4525), Abstract relocated at http://www.asco.org/ASCOv2/Meetings/Abstracts? &vmview=abst_detail_view&confID=65&abstractID=35160, last visited on Feb. 23, 2010, 3 pages. (Abstract).

Von Hoff, D. D. et al. (2009). "SPARC Correlation with Response to Gemcitabine (G) Plus *nab*-Paclitaxel (*nab*-P) in Patients with Advanced Pancreatic Cancer," Poster-Discussion presented at the *2009 ASCO Annual Meeting*, in Orlando, Florida, on May 29-Jun. 2, 2009, 13 pages (Poster).

Vorum, H. (Nov. 1999). "Reversible Ligand Binding to Human Serum Albumin," *Dan. Med. Bull.* 46(5):379-399.

Weiss, R. B. et al. (Jul. 1990). "Hypersensitivity Reactions from Taxol," *J. Clin. Oncol.* 8(7):1263-1268.

Welch, S. A. et al. (Jun. 1, 2007) "Combination Chemotherapy in Advanced Pancreatic Cancer: Time to Raise The White Flag?" *J. Clin. Oncol.* 25(16):2159-2161.

Willett, C. G. et al. (Dec. 2003). "Update on Combined-Modality Treatment Options for Pancreatic Cancer," *Oncology* 17(12): Suppl. 13, pp. 29-36.

Winer, E. et al. (1998). "Failure of Higher Dose Paclitaxel to Improve Outcome in Patients With Metastatic Breast Cancer—Results From CALGB 9342," Abstract presented at the 1998 ASCO Annual Meeting, Abstract located at http://www.asco.org/ascov2/ Meetings/Abstracts?&vmview=abst_detail_view&confID=31 &abstractID=12751, last visited on Jul. 18, 2012, Abstract No. 388, 3 pages.

Witkiewicz, A.K. et al. (2008). "Co-expression of fatty acid synthase and caveolin-1 in pancreatic ductal adenocarcinoma: Implications for tumor progression and clinical outcome", *Cell Cycle*, 7(19):3021-3025.

Wozniak, A. J. et al. (Jul. 1998). "Randomized Trial Comparing Cisplatin with Cisplatin plus Vinorelbine in the Treatment of Advanced Non-Small-Cell Lung Cancer: A Southwest Oncology Group Study," *J. Clin. Oncol.* 16(7):2459-2465.

Yang, G. et al. (Aug. 1998). "Elevated Expression of Caveolin is Associated With Prostate and Breast Cancer," *Clin. Cancer Res.* 4(8):1873-1880.

Yoo, S.-H. et al. (2003). "Expression of Caveolin-1 is Associated with Poor Prognosis of Patients with Squamous Cell Carcinoma of the Lung," *Lung Cancer* 42:195-202.

Zalcberg, J. et al. (May 1998). "Phase II Study of Docetaxel and Cisplatin in Advanced Non-Small-Cell Lung Cancer," *J. Clin. Onc.* 16(5):1948-1953.

Zeinalova, K. P. et al. (2005). "Avastatin (Bevacizumab) in Treating Malignant Tumors: New Data," *Farmateka* 18(113):22-26, with English translation (14 pages).

International Search Report mailed on Jul. 7, 2006, for PCT Patent Application No. PCT/US2006/006167, filed on Feb. 21, 2006, published on Aug. 24, 2006, as WO 2006/089290, 4 pages.

Written Opinion mailed on Jul. 7, 2006 for PCT Patent Application No. PCT/US2006/006167, filed on Feb. 21, 2006, published on Aug. 24, 2006, as WO 2006/089290, 7 pages.

International Search Report mailed on Mar. 17, 2008, for PCT Patent Application No. PCT/US2007/023446, filed on Nov. 6, 2007, published on May 15, 2008, as WO 2008/057562, 3 pages.

Written Opinion mailed on Mar. 17, 2008, for PCT Patent Application No. PCT/US2007/023446, filed on Nov. 6, 2007, published on May 15, 2008, as WO 2008/057562, 6 pages.

European Search Report mailed on Jun. 29, 2011, for European Patent Application No. 10011106.1, filed on Feb. 21, 2006, 9 pages.

European Search Report mailed on Jul. 3, 2012, for European Patent Application No. 12154995.0, filed on Nov. 6, 2007, 6 pages.

International Search Report mailed on Jun. 6, 2011, for PCT Patent Application No. PCT/US2011/030209, filed on Mar. 28, 2011, published on Oct. 6, 2011, as WO 2011/123395, 6 pages.

Written Opinion mailed on Jun. 6, 2011, for PCT Patent Application No. PCT/US2011/030209, filed on Mar. 28, 2011, published on Oct. 6, 2011, as WO 2011/123395, 8 pages.

International Search Report mailed on May 30, 2011, for PCT Patent Application No. PCT/US2011/030206, filed on Mar. 28, 2011, published on Oct. 6, 2011, as WO 2011/123393, 5 pages.

Written Opinion mailed on May 30, 2011, for PCT Patent Application No. PCT/US2011/030206, filed on Mar. 28, 2011, published on Oct. 6, 2011, as WO 2011/123393, 6 pages.

U.S. Appl. No. 09/446,783, filed May 16, 2000, for Desai et al.
U.S. Appl. No. 09/937,840, filed Jan. 28, 2002, for Desai et al.
U.S. Appl. No. 12/479,710, filed Jun. 5, 2009 for Desai et al.
U.S. Appl. No. 14/362,382, filed Jun. 2, 2014, for Foss et al.
U.S. Appl. No. 14/626,678, filed Feb. 19, 2015, by Desai et al.
U.S. Appl. No. 14/631,671, filed Feb. 25, 2015, by Desai et al.
U.S. Appl. No. 14/660,872, filed Mar. 17, 2015, by Desai et al.
U.S. Appl. No. 14/714,131, filed May 15, 2015, by Seward et al.

Arkhipova, K.A. et al. (2009). "Caveolin-1 Expression in Soft Tissue Tumors," *Blokhina* 20(1):4-9, found on Jul. 29, 2015 on the Web-site http://www.ronc.ru/attachments/article/1735/ vestnikronic_1_2009.pdf . (English Abstract Only.).

Ashcroft, T. et al. (1988). "Simple Method of Estimating Severity of Pulmonary Fibrosis on a Numerical Scale," *J. Clin. Pathol.* 41:467-470.

Bergamaschi, A. et al. (2008, e-pub. Nov. 29, 2007). "Extracellular Matrix Signature Identifies Breast Cancer Subgroups With Different Clinical Outcome," *Journal of Pathology* 214:357-367.

Bertino, E.M. et al. (2015). "Stomal Caveolin-1 is Associated With Response and Survival in a Phase II Trial of *nab*-Paclitaxel With Carboplatin for Advanced NSCLC Patients," *Clinical Lung Cancer*, pp. 1-9.

Che, Y. et al. (2006). "The Differential Expression of SPARC in Esophageal Squamous Cell Carcinoma," *International Journal of Molecular Medicine* 17(6):1027-1033.

Farkas, L. et al. (May 2009). "VEGF Ameliorates Pulmonary Hypertension Through Inhibition of Endothelial Apoptosis in Experimental Lung Fibrosis in Rats," *The Journal of Clinical Investigation* 119(5):1298-1311.

Ferrini, F.S. et al . (2001). "Schirrous Invasive Ductal Carcinoma of the Breast Overexpress p53 Oncoprotein," *Sao Paulo Medical Journal* 119(1):4-6.

Goode, E.L et al. (2002). "Polymorphisms in DNA Repair Genes and Associations With Cancer Risk," *Cancer Epidemiol. Biomarkers Prev.* 11(12):1513-1530.

Khodyrev, D.S. et al. (2009). "Changes in Promoter Regions Methylation in Seven Human Chromosome 3 Genes in Epithelial Tumors," Moscow, p. 7 and 10 (Introduction Translated into English).

Lallemant, B. et al. (Oct. 18, 2009). "Clinical Relevance of Nine Transcriptional Molecular Markers of the Diagnosis of Head and Neck Squamous Cell Carcinoma in Tissue and Saliva Rinse," *BMC Cancer* 9(370):1-10.

Oldberg, Å. et al. (Aug. 28, 2007). "Collagen-Binding Proteoglycan Fibromodulin Can Determine Stroma Matrix Structure and Fluid Balance in Experimental Carcinoma," *Proc. Nat. Acad. Sci. USA* 104(35):13966-13971.

Orlov, S.V. (2000). "Non-Small Cell Lung Cancer Symptoms, Diagnostics, and Staging," *Medical Sciences* 3:8-16, (English Translation).

Rempel, S.A. (Feb. 1999). "SPARC: A Potential Diagnostic Marker of Invasive Meningiomas," *Clin. Cancer Res.* 5:237-242.

(56) References Cited

OTHER PUBLICATIONS

Shigematsu, H. et al. (2006). "Somatic Mutations of Epidermal Growth Factor Receptor Signaling Pathway in Lung Cancers," *International Journal of Cancer* 118(2):257-262.

Smolyakovia, R.M. et al. (2003). "Clinicodiagnostic Significance of the Tests of Structural and Functional Properties of Serum Albmin in Small-Cell Lung Cancer Patients," *Onkolog. J. Sibiri* 4(12):12-16, (English Abstract Only).

Song, C.W. et al. (2006). "Influence of Tumor pH on Therapeutic Response," Chapter 2 in *Cancer Drug Discovery and Development, Cancer Resistance*, Teicher, B. ed., Humana.Press, Inc., Totowa, NJ, pp. 21-45.

Tamboli, P. et al. (2006). "Pathological Evaluation of Lung Cancer," Chapter 4 in *Lung Cancer MD Anderson Cancer Care Series*, Fossella, A.F.V. et al. eds., pp. 36-37. (In Japanese with English Translation).

Woenchkhaus, M. et al. (May 2005). "Multitarget FISH and LOH analyses at chromosome 3p in non-small cell lung cancer and adjacent bronchial epithelium," *Am. J. Clin. Pathol.* 123(5):752-761.

Zhang, J. et al. (Jan. 2009). "Expression and Clinical Significance of SPARC in Clinical Stage II Tongue Squamous Cell Carcinoma," *Chinese Journal of Cancer* 28(1):68-71.

Non-Final Office Action mailed on Oct. 30, 2014, for U.S. Appl. No. 13/782,988, filed Mar. 1, 2013, 11 pages.

Non-Final Office Action mailed on Jan. 21, 2015, for U.S. Appl. No. 13/791,841, filed Mar. 8, 2013, 22 pages.

Non-Final Office Action mailed on Feb. 11, 2015, for U.S. Appl. No. 13/701,001, Internationally filed May 20, 2011, 15 pages.

Non-Final Office Action mailed on Feb. 12, 2015, for U.S. Appl. No. 13/782,992, filed Mar. 1, 2013, 16 pages.

Non-Final Office Action mailed on Apr. 9, 2015, for U.S. Appl. No. 13/073,861, filed Mar. 28, 2011, 20 pages.

Final Office Action mailed Jun. 3, 2015, for U.S. Appl. No. 13/782,988, filed Mar. 1, 2013, 14 pages.

Final Office Action mailed on Jul. 10, 2015, for U.S. Appl. No. 13/263,723, filed May 4, 2012, 42 pages.

U.S. Appl. No. 14/834,331, filed Aug. 24, 2015, by Desai et al.

U.S. Appl. No. 14/835,458, filed Aug. 25, 2015, by Desai et al.

Müller, B.G. et al. (1996). "Albumin Nanospheres as Carriers for Passive Drug Targeting: An Optimized Manufacturing Technique," *Pharmaceutical Research* 13(1):32-37.

METHODS OF TREATING CANCER

CROSS-REFERENCE TO RELATED APPLICATIONS

This application is a continuation of U.S. patent Ser. No. 13/073,824, filed Mar. 28, 2011; which claims priority benefit to U.S. Provisional Patent Application No. 61/318,774, filed Mar. 29, 2010 and 61/433,132, filed on Jan. 14, 2011, the content of each of which is incorporated herein in their entirety.

TECHNICAL FIELD

The present invention relates to methods and compositions for the treatment of non-small-cell lung cancer (NSCLC) by administering compositions comprising nanoparticles that comprise paclitaxel and an albumin and a platinum-based agent (e.g. carboplatin).

BACKGROUND

Lung cancer is the leading cause of cancer death in both men and women in the United States. In 1998, an estimated 171,500 new cases were diagnosed, and about 160,100 deaths resulted from this disease. More women die from lung cancer than breast, ovarian, and uterine cancer combined, and 4 times as many men die from lung cancer than from prostate cancer. Most patients who are diagnosed with NSCLC cannot be cured with surgery and will eventually die from their disease. See SEER Cancer Statistics Review 2001. The median survival of patients with untreated metastatic NSCLC is only four to five months with a survival rate at one year of only 10 percent. Rapp E. et al. *J Clin Oncol.* 1988; 6:633-41.

Chemotherapy only moderately improves the median survival time (MST) of patients with locally advanced or metastatic NSCLC when compared to best supportive care (BSC). The first generation of chemotherapy agents extended the survival of patients with stage IIIB and IV NSCLC by 10% to 15%, when compared to BSC. Several meta-analyses indicate that cisplatin-containing regimens confer an increase of 6 to 8 weeks in MST and of 15% to 25% in 1-year survival. See Non Small Cell Lung Cancer Collaborative Group. *Br Med J.* 1995; 311:899-909; Grilli R. et al. *J Clin Oncol.* 1993; 11:1866-1872; Souquet P. J. et al. *Lancet* 1993; 342:19-21. The most commonly used agents to treat NSCLC include carboplatin (response rate (RR): 20%-25%; see Bonomi P. D. et al. *J Clin Oncol.* 1989; 7:1602-13), Taxol® (RR: 20%-25%; see Gatzemeier U. et al. Lung Cancer. 1995; 12(Suppl 2):S101-5106; Hainsworth J. D. et al. J Clin Oncol, 1995. 13(7):1609-1614), docetaxel (RR: 23%-33%; see Fossella F. V. et al. *J Clin Oncol.* 1995; 13(3):645-651; Cerny T. et al. *Br J Cancer.* 1994; 70:384-387), gemcitabine (RR: 20%-25%; see Shepherd F. A. *Anticancer Drugs.* 1995; 6(Suppl 6):9-25; Sorensen J. B. *Lung Cancer.* 1995; 12 (Suppl 1):5173-5175), and vinorelbine (RR: 29.4%; see Depierre A. et al. *Proc ASCO,* 1988. 7:201). The MST for these drugs varies from 7.5 to 9.5 months.

Most treatment combinations to date center on the use of platinum-based regimens. Platinum-based agents are alkylating agents which bind covalently to DNA and cross-links DNA strands, resulting in inhibition of DNA synthesis and function as well as inhibition of transcription. Platinum-based chemotherapy combinations have demonstrated improvements over single-agent therapy in advanced NSCLC. See Dubey S, and Schiller J. H. *Hematol Oncol Clin N Am.* 2004; 18:101-114. For example, Taxol® (200-225 mg/m$^2$) in combination with carboplatin (AUC=6) administered q3w is a commonly used and well accepted treatment regimen for patients with NSCLC, producing objective response rates in Phase III studies of 17%, 25%, 29%, 32%, and 37%. See Schiller J. H. et al. *N Engl J Med.* 2002; 346:92-98; Kelly K. et al. *J Clin Oncol.* 2001; 19:3210-3218; Herbst R. S. et al. *J Clin Oncol.* 2004; 22:785-794; Scagliotti G. V. et al. *J Clin Oncol.* 2002; 20:4285-4291; Lilenbaum R. C. et al. Presented at: *American Society of Clinical Oncology (ASCO),* June 2002. Abstract 2. Toxicities associated with this regimen were similar in nature to those associated with Taxol® and carboplatin individually, and the combination demonstrated no new or unexpected toxicities. The efficacy parameters were similar between Taxol® 100 mg/m$^2$ weekly for 3 of 4 weeks with carboplatin AUC=6 and Taxol® 100 mg/m$^2$ and carboplatin AUC=6 on day 1 of each 3-week cycle. See Belani et al. *J Clin Oncol.* 2008; 26(3):468-473.

A recent Phase III study comparing carboplatin/Taxol® to other doublets (cisplatin/Taxol® vs. cisplatin/gemcitabine vs. cisplatin/docetaxel vs. carboplatin/Taxol®) demonstrated that all the combinations have similar efficacy. See Schiller J. H. et al. *N Engl J Med.* 2002; 346:92-98. However, because of its more favorable safety profile, the Eastern Collaborative Oncology Group (ECOG) selected carboplatin/Taxol® as its reference regimen for future studies. See Schiller J. H. et al. *N Engl J Med.* 2002; 346:92-98.

Taxol® (Bristol-Myers Squibb Co., Princeton, N.J.) contains the chemotherapeutic active agent paclitaxel. Paclitaxel binds to the β-subunit of tubulin, the building blocks of microtubules, causing hyper-stabilization of the microtubule structures. The resulting paclitaxel/microtubule structure is unable to disassemble, thereby arresting mitosis and inhibiting angiogenesis. Because paclitaxel is highly hydrophobic, commercially available formulations include synthetic solvents to enable parenteral administration: Taxol® contains a combination of Cremophor® EL (polyethylated castor oil) and ethanol as paclitaxel vehicle.

The solvent used in Taxol® raises major concerns due to its intrinsic negative properties. Emerging data indicate that Cremophor is a biologically and pharmacologically active compound that directly contributes to the severe toxicities observed in patients treated with Taxol®. Among the well-characterized, solvent-related toxicities are severe hypersensitivity reactions (which can be fatal even with steroid premedication); histamine release; and prolonged, sometimes irreversible peripheral neuropathy associated with demyelination and axonal degeneration. See Gelderblom H. et al. *Eur J Cancer.* 2001; 37:1590-8. Review; Lorenz W. et al. *Agents and Actions* 1977; 7:63-67; Weiss R. B. et al. *J Clin Oncol.* 1990; 8:1263-1268. Furthermore, these solubilizers adversely affect efficacy due to entrapment of active drug in micelles formed in the plasma compartment. See ten Tije A. J. et al. *Clin Pharmacokinet.* 2003; 42:665-85. Review. Such entrapment alters drug pharmacokinetics (PK), leading to highly increased systemic drug exposure, decreased drug clearance, nonlinear PK, and lack of dose-dependent antitumor activity. See ten Tije A. J. et al. *Clin Pharmacokinet.* 2003; 42:665-85. Review; Winer E. et al. *Proceedings of ASCO* 1998, Vol 17, Abstract 388; Sparreboom A. et al. *Cancer Res.* 1999; 59(7):1454-1457; van Tellingen O. et al. *Br J Cancer.* 1999; 81:330-5. Drug entrapment affects not only the taxanes but also co-administered drugs (e.g., anthracyclines, platinum compounds) and, thus, is an important consideration in the design of combination therapies. See ten Tije A. J. et al. *Clin Pharmacokinet.* 2003; 42:665-85. Review.

As emerging data has indicated that the solvent used in Taxol® may negatively impact the efficacy and toxicity profile of chemotherapy comprising Taxol®, new paclitaxel formulations have been developed. Nab-paclitaxel (ABI-007 or Abraxane®; Abraxis BioScience, Los Angeles, Calif.) is a novel, solvent-free, non-crystalline, amorphous, albumin-bound, paclitaxel particle with a mean size of approximately 130 nm suspended in normal saline See, for example, U.S. Pat. Nos. 5,916,596; 6,506,405; 6,749,868, 6,537,579, and U.S. Pat. No. 7,820,788 and also in U.S. Pat. Pub. No. 2007/0082838. Nab-paclitaxel is the first of a new class of anticancer agents that incorporate particle technology and exploit the unique properties of albumin, a natural carrier of lipophilic molecules in humans. Nab-paclitaxel utilizes the albumin receptor (gp60)/caveolin-1 (CAV1) pathway achieving high intratumoral paclitaxel accumulation. See Desai et al. *Clin Cancer Res.* 2006; 12(4):1317-1324. Nab-paclitaxel has advantages compared to Taxol® with regards to reduced toxicity, greater ease of administration, shorter drug infusion time, and avoidance of hypersensitivity reactions.

Nab-paclitaxel, when administered at a dose of 260 mg/m$^2$ every 3 weeks to 43 patients with NSCLC as first-line therapy, resulted in an objective response rate of 16% with an additional 49% of patients achieving disease control (defined as stable disease for at least 16 weeks plus objective responses) and was well tolerated with no patients developing any Grade 4 toxicity at any time during the treatment course. See Green M. R. et al. *Ann Oncol.* 2006; 17:1263-8. When Nab-paclitaxel was given at a dose of 125 mg/m$^2$ weekly for 3 weeks followed by one week off to 40 elderly patients with Stage IV NSCLC (median age 70), the objective response and disease control rates were 30% and 50% respectively. See Rizvi N. A. et al. *J Clin Oncol.,* 2006 ASCO Annual Meeting Proceedings (Post-Meeting Edition). Vol 24, No 18S (June 20 Supplement), 2006: 7105.

A high monotherapy response rate does not necessarily translate into a significantly higher combination therapy response rate in a Phase III trial, let alone result in additive efficacy. See Lynch et al. *J Clin Oncol.* 2010; 28(6):911-917 ("More than a dozen phase III trials have unsuccessfully investigated targeted approaches combined with platinum doublets.").

In view of the improved objective response rates compared to Taxol®, Nab-paclitaxel was combined with carboplatin to evaluate efficacy and toxicity in NSCLC. In 100 patients treated with carboplatin (AUC 6) plus Nab-paclitaxel every 3 weeks at doses between 225 and 340 mg/m$^2$, the overall response rate was 27% (see Hawkins M. J. et al. *J Clin Oncol.,* 2006 ASCO Annual Meeting Proceedings (Post-Meeting Edition). Vol 24, No 18S (June 20 Supplement), 2006: 7132) and a 50% response rate was reported using 100 mg/m$^2$ Nab-paclitaxel weekly in combination with carboplatin in NSCLC patients (see Allerton J. P. et al. *J Clin Oncol.,* 2006 ASCO Annual Meeting Proceedings (Post-Meeting Edition). Vol 24, No 18S (June 20 Supplement), 2006: 7127). Further, in another study, NSCLC patients with histologic confirmation of adenocarcinoma receiving Nab-paclitaxel weekly in combination with carboplatin achieved a 59% ORR while NSCLC patients with histologic confirmation of squamous cell carcinoma achieved a 39% ORR. See Socinski M. A. et al. *IASLC,* 13$^{th}$ *Word Conference on Lung Cancer.* San Francisco, Calif.; Jul. 31-Aug. 4, 2009.

Further data is emerging that NSCLC is a diverse cancer with treatment and survival outcomes often dependent upon the histology of the malignancy and the molecule profile of the NSCLC. For example, survival analysis has previously shown a significant association of stromal SPARC (also known as osteonectin and BM40) with markers of hypoxia/acidity and with poor prognosis in non-small cell lung cancer. See Koukourakis et al. *Cancer Research.* 2003. 63:53756-5380. In addition, previous studies also have indicated that histology can be an important predictor for clinical response. In a NSCLC Phase III trial comparing cisplatin plus gemcitabine with cisplatin plus pemetrexed, for example, the use of cisplatin and pemetrexed in patient with adenocarcinoma and large-cell carcinoma resulted in significantly better survival than cisplatin and gemcitabine therapy while no significant difference was observed in squamous cell carcinoma. See Scagliotti et al. *J Clin Oncol.* 2008; 26(21)3543-3551. Squamous cell carcinoma of the lung accounts for one-third of primary lung cancer and a common malignant tumor with poor prognosis. In squamous cell carcinoma, advanced pathologic stage and poor prognosis have been correlated with increased caveolin-1 expression. Yoo et al. *Lung Cancer.* 2003 42:195-202.

The continued evaluation of new approaches to treat NSCLC is imperative to increase survival and quality of life of for NSCLC patients.

The disclosures of all publications, patents, patent applications and published patent applications referred to herein are hereby incorporated herein by reference in their entirety. The present application also incorporates U.S. Provisional Patent Application No. 61/318,777 by reference in its entirety.

BRIEF SUMMARY OF THE INVENTION

Provided herein are methods of treating non-small-cell lung cancer (NSCLC) in an individual in need thereof, comprising administering to the individual (a) an effective amount of a composition comprising nanoparticles comprising paclitaxel and albumin (hereinafter also referred to as "the nanoparticle composition" or "paclitaxel nanoparticle composition"); and (b) an effective amount of a platinum-based agent.

In some embodiments, the NSCLC is squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments, the NSCLC is squamous cell carcinoma. In some embodiments, the NSCLC is an occult tumor, a stage 0 tumor, a stage I tumor, a stage II tumor, a stage IIIA tumor, a stage IIIB tumor, or a stage IV tumor. In some embodiments, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable. In some embodiments, the NSCLC is inoperable Stage IIIA and/or IIIB NSCLC, PS 0-1, and FEV 1>800 ml. In some embodiments, the method is for treating NSCLC as first-line therapy or second-line therapy. In some embodiments, the individual to be treated is ineligible for VEGF-directed therapy, for example, ineligible for treatment with bevacizumab. In some embodiments, the individual is at risk of bleeding from VEGF directed therapy.

In some embodiments, the effective amount of the composition comprising nanoparticles comprising paclitaxel and the albumin is between about 50 to about 125 mg/m² (e.g., 50 mg/m², 75 mg/m², or 100 mg/m²) and the effective amount of the platinum-based agent is between about AUC=2 to about AUC=6 (e.g., AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the effective amount of the composition comprising nanoparticles comprising paclitaxel and the albumin is between about 50 to about 125 mg/m² administered weekly and the effective amount of the platinum-based agent is between about AUC=2 to about AUC=6 administered once every three weeks. In some embodiments, the effective amount of the composition comprising nanoparticles comprising paclitaxel and the albumin is about 100 mg/m² administered weekly and the effective amount of the platinum-based agent is about AUC=6 administered once every three weeks. In some embodiments, the effective amount of the composition comprising nanoparticles comprising paclitaxel and the albumin is about 75 mg/m² administered weekly and the effective amount of the platinum-based agent is about AUC=4.5 administered once every three weeks. In some embodiments, the effective amount of the composition comprising nanoparticles comprising paclitaxel and the albumin is about 50 mg/m² administered weekly and the effective amount of the platinum-based agent is about AUC=3 administered once every three weeks. In some embodiments, the paclitaxel nanoparticle composition and/or the platinum-based agent is administered intravenously. In some embodiments, the paclitaxel nanoparticle composition and the platinum-based agent are administered intravenously.

In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (Abraxane®)). In some embodiments, the composition is Nab-paclitaxel (Abraxane®).

In some embodiments, the platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the composition comprising nanoparticles comprising paclitaxel and an albumin and the platinum-based agent are sequentially administered, concurrently administered or simultaneously administered.

The methods described herein can be used for any one or more of the following purposes: alleviating one or more symptoms of NSCLC, delaying progression of NSCLC, shrinking tumor size in NSCLC patient, inhibiting NSCLC tumor growth, prolonging overall survival, prolonging progression free survival, preventing or delaying NSCLC tumor metastasis, reducing (such as eradiating) preexisting NSCLC tumor metastasis, reducing incidence or burden of preexisting NSCLC tumor metastasis, or preventing recurrence of NSCLC.

Thus, for example, the invention provides methods of treating NSCLC in an individual in need thereof, comprising administering to the individual (a) an effective amount of a composition comprising nanoparticles comprising paclitaxel and albumin; and (b) an effective amount of carboplatin, wherein the effective amount of the composition comprising nanoparticles comprising paclitaxel and albumin is 100 mg/m² administered weekly and the effective amount of a carboplatin is AUC=6 administered once every three weeks.

The invention therefore also provides methods of treating advanced NSCLC in an individual in need thereof, comprising administering to the individual (a) an effective amount of a composition comprising nanoparticles comprising paclitaxel and albumin; and (b) an effective amount of carboplatin, wherein the effective amount of the composition comprising nanoparticles comprising paclitaxel and albumin is 100 mg/m² administered weekly and the effective amount of carboplatin is AUC=6 administered once every three weeks as first-line therapy.

Thus also provided are methods of treating NSCLC in an individual in need thereof, comprising administering to the individual a) an effective amount of a composition comprising nanoparticles comprising paclitaxel and an albumin and b) an effective amount of a platinum-based agent, wherein the NSCLC is squamous cellular carcinoma.

In some embodiments, there are provided methods of treating NSCLC in an individual in need thereof, comprising administering to the individual a) an effective amount of a composition comprising nanoparticles comprising paclitaxel and an albumin and b) an effective amount of a platinum-based agent, wherein the individual to be treated is ineligible for VEGF-directed therapy, for example, ineligible for treatment with bevacizumab. In some embodiments, the individual is at risk of bleeding from VEGF directed therapy.

Also provided herein are methods of treating NSCLC in an individual (e.g., human) comprising administering to the individual a) an effective amount of a composition comprising nanoparticles comprising paclitaxel and an albumin; b) an effective amount of a platinum-based agent, and c) radiation (e.g. thoracic radiation), wherein the effective amount of the composition comprising nanoparticles comprising paclitaxel and albumin is between 20 mg/m² to about 60 mg/m² (e.g., 40 mg/m²) administered weekly, the effective amount of a platinum-based agent is between about AUC=2 to about AUC=6 (e.g., AUC=2) administered weekly, and the thoracic radiation is between about 25 to about 40 (e.g., about 33) fractions by either 3D conformal or intensity-modulated techniques concurrently. In some embodiments, the method of treating NSCLC in an individual (e.g., human) comprising administering to the individual a) an effective amount of a composition comprising nanoparticles comprising paclitaxel and an albumin; b) an effective amount of a platinum-based agent, and c) radiation (e.g. thoracic radiation), wherein the effective amount of the composition comprising nanoparticles comprising paclitaxel and albumin is between 20 mg/m² to about 60 mg/m² (e.g., 40 mg/m²) administered weekly, the effective amount of a platinum-based agent is between about AUC=2 to about AUC=6 (e.g., AUC=2) administered weekly, and the thoracic radiation is between about 25 to about 40 (e.g., about 33) fractions by either 3D conformal or intensity-modulated techniques concurrently further comprises a consolidation therapy, wherein the consolidation therapy comprises administering to the individual a) an effective amount of a composition comprising nanoparticles comprising paclitaxel and an albumin and b) an effective amount of a platinum-based agent, wherein the effective amount of the composition comprising nanoparticles comprising paclitaxel and albumin is between about 50 to about 125 mg/m² (e.g., 50 mg/m², 75 mg/m², or 100 mg/m²) administered weekly and the effective amount of carboplatin is between about AUC=2 to about AUC=6 (e.g., AUC=3, AUC=4.5, or AUC=6) administered once every three weeks. In some embodiments NSCLC is inoperable Stage IIIA and/or IIIB NSCLC. In some embodiments, the NSCLC is inoperable Stage IIIA and/or IIIB NSCLC, PS 0-1, and FEV 1>800 ml. In some embodiments, the platinum based agent is carboplatin.

Also provided are methods of treating NSCLC in an individual comprising administering to the individual a) an effective amount of a composition comprising nanoparticles comprising paclitaxel and an albumin and b) an effective amount of a platinum-based agent, wherein treatment is based upon the NSCLC having one or more characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Further provided herein are methods of treating NSCLC in an individual provided that the NSCLC has been found to have one or more characteristics selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake, the treatment comprising administering to the individual i) an effective amount of a composition comprising nanoparticles comprising paclitaxel and an albumin and ii) an effective amount of a platinum-based agent.

Provided herein are also methods of treating NSCLC, comprising: (a) selecting an individual having NSCLC, wherein the NSCLC has one or more characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (b) administering to the individual thus selected i) an effective amount of a composition comprising nanoparticles comprising paclitaxel and an albumin and ii) an effective amount of a platinum-based agent.

Methods are also provided herein of assessing whether an individual with NSCLC will respond to treatment comprising assessing one or more characteristics of the NSCLC selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake, wherein one or more of the characteristics of the NSCLC indicates the individual will be responsive to the treatment and the treatment comprises i) an effective amount of a composition comprising nanoparticles comprising paclitaxel and an albumin and ii) an effective amount of a platinum-based agent.

In addition, methods are provided herein of identifying an individual with NSCLC likely to respond to treatment comprising a) a composition comprising nanoparticles comprising paclitaxel and an albumin and b) a platinum-based agent comprising: (A) assessing one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (B) identifying the individual having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Provided herein are also methods for marketing a combination therapy comprising a) a composition comprising nanoparticles comprising paclitaxel and an albumin and b) a platinum-based agent for use in a NSCLC individual subpopulation, the methods comprising informing a target audience about the use of the combination therapy for treating the individual subpopulation characterized by the individuals of such subpopulation having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

In some embodiments of any of the methods, differential levels of tumor acidity are evident by differential levels of carbonic anhydrase-9 (CA-9) and/or differential levels of LDH (e.g., LDH-5). In some embodiments of any of the methods, differential levels of hyopoxia markers are evident by differential levels of HIF-1α, differential levels of HIF-2α, and/or differential levels of differentiated embryo-chrondrocyte expressed gene 1 (DEC-1).

In some embodiments of any of the methods above, the methods result in a measurable reduction in tumor size or evidence of disease or disease progression, complete response, partial response, stable disease, increase or elongation of progression free survival, increase or elongation of overall survival, or reduction in toxicity.

In some embodiments of any of the methods above, differential levels are over expression (high expression) or under expression (low expression) as compared to the expression level of a normal or control cell, a given patient population, or with an internal control. In some embodiments, levels are compared between the individual and a normal patient population, between an individual and a NSCLC patient population with a different NSCLC histology, or between an individual and a NSCLC patient population with the same NSCLC histology.

In some embodiments, differential levels is determined in tumor tissue, normal tissue adjacent to said tumor, normal tissue distal to said tumor or peripheral blood lymphocytes.

In some embodiments of any of the methods described herein, the NSCLC is squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments, the NSCLC is squamous cell carcinoma. In some embodiments of any of the methods described herein, the NSCLC is an occult tumor, a stage 0 tumor, a stage I tumor, a stage II tumor, a stage IIIA tumor, a stage IIIB tumor, or a stage IV tumor. In some embodiments of any of the methods described herein, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable. In some embodiments, the NSCLC is inoperable Stage IIIA and/or IIIB NSCLC, PS 0-1, and FEV 1>800 ml. In some embodiments of any of the methods described herein, the method is for treating NSCLC as first-line therapy or second-line therapy.

In some embodiments, the effective amount of the composition comprising nanoparticles comprising paclitaxel and the albumin is between about 50 to about 125 mg/m$^2$ (e.g., 50 mg/m$^2$, 75 mg/m$^2$, or 100 mg/m$^2$) and the effective amount of the platinum-based agent is between about AUC=2 to about AUC=6 (e.g., AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the effective amount of the composition comprising nanoparticles comprising paclitaxel and the albumin is between about 50 to about 125 mg/m$^2$ administered weekly and the effective amount of the platinum-based agent is between about AUC=2 to about AUC=6 administered once every three weeks. In some embodiments, the effective amount of the composition comprising nanoparticles comprising paclitaxel and the albumin is about 100 mg/m$^2$ administered weekly and the effective amount of the platinum-based agent is about AUC=6 administered once every three weeks. In some embodiments, the effective amount of the composition comprising nanoparticles comprising paclitaxel and the albumin is about 75 mg/m$^2$ administered weekly and the effective amount of the platinum-based agent is about AUC=4.5 administered once every three weeks. In some embodiments, the effective amount of the composition comprising nanoparticles comprising paclitaxel and the albumin is about 50 mg/m$^2$ administered weekly and the effective amount of the platinum-based agent is about AUC=3 administered once every three weeks. In some embodiments, the paclitaxel nanoparticle composition and/or the platinum-based agent is administered intravenously. In some embodiments, the paclitaxel nanoparticle composition and the platinum-based agent are administered intravenously.

In some embodiments, the albumin is human serum albumin. In some embodiments, the nanoparticles comprise paclitaxel coated with albumin. In some embodiments, the average particle size of the nanoparticles in the nanoparticle composition is no more than about 200 nm (such as less than about 200 nm). In some embodiments, the composition comprises the albumin stabilized nanoparticle formulation of paclitaxel (Nab-paclitaxel (Abraxane®)). In some embodiments, the composition is Nab-paclitaxel (Abraxane®).

In some embodiments, the platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the composition comprising nanoparticles comprising paclitaxel and an albumin and the platinum-based agent are sequentially administered; concurrently administered or simultaneously administered.

Also provided are compositions (such as pharmaceutical compositions), medicine, kits, and unit dosages useful for methods described herein.

These and other aspects and advantages of the present invention will become apparent from the subsequent detailed description and the appended claims. It is to be understood that one, some, or all of the properties of the various embodiments described herein may be combined to form other embodiments of the present invention.

DETAILED DESCRIPTION OF THE INVENTION

The present invention provides methods of combination therapy for treating NSCLC by administering a) a composition comprising nanoparticles comprising paclitaxel and an albumin and b) a platinum-based agent (such as carboplatin). In another aspect, there is provided a method of treating NSCLC in an individual in need thereof, comprising administering to the individual (a) an effective amount of a composition comprising nanoparticles comprising paclitaxel and albumin; and (b) an effective amount of a platinum-based agent.

Also provided are compositions (such as pharmaceutical compositions), medicine, kits, and unit dosages useful for the methods described herein.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of NSCLC. The methods of the invention contemplate any one or more of these aspects of treatment.

The term "individual" refers to a mammal and includes, but is not limited to, human, bovine, horse, feline, canine, rodent, or primate. Preferably, the individual is a human.

As used herein, an "at risk" individual is an individual who is at risk of developing NSCLC. An individual "at risk" may or may not have detectable disease, and may or may not have displayed detectable disease prior to the treatment methods described herein. "At risk" denotes that an individual has one or more so-called risk factors, which are measurable parameters that correlate with development of NSCLC, which are described herein. An individual having one or more of these risk factors has a higher probability of developing cancer than an individual without these risk factor(s).

"Adjuvant setting" refers to a clinical setting in which an individual has had a history of NSCLC, and generally (but not necessarily) been responsive to therapy, which includes, but is not limited to, surgery (e.g., surgery resection), radiotherapy, and chemotherapy. However, because of their history of NSCLC, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of NSCLC means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of NSCLC is a method that reduces probability of disease development in a given time frame and/or reduces the extent of the disease in a given time frame, when compared to not using the method. Such comparisons are typically based on clinical studies, using a statistically significant number of subjects. NSCLC development can be detectable using standard methods, including, but not limited to, computerized axial tomography (CAT Scan), Magnetic Resonance Imaging (MRI), abdominal ultrasound, clotting tests, arteriography, or biopsy. Development may also refer to NSCLC progression that may be initially undetectable and includes occurrence, recurrence, and onset.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual. Such combinations are considered to be part of a single treatment regiment or regime.

The term "effective amount" used herein refers to an amount of a compound or composition sufficient to treat a specified disorder, condition or disease such as ameliorate, palliate, lessen, and/or delay one or more of its symptoms. In reference to NSCLC, an effective amount comprises an amount sufficient to cause a tumor to shrink and/or to decrease the growth rate of the tumor (such as to suppress tumor growth) or to prevent or delay other unwanted cell proliferation in NSCLC. In some embodiments, an effective amount is an amount sufficient to delay development of NSCLC. In some embodiments, an effective amount is an amount sufficient to prevent or delay recurrence. An effective amount can be administered in one or more administrations. In the case of NSCLC, the effective amount of the drug or composition may: (i) reduce the number of NSCLC cells; (ii) reduce tumor size; (iii) inhibit, retard, slow to some extent and preferably stop NSCLC cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with NSCLC.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An "adverse event" or "AE" as used herein refers to any untoward medical occurrence in a patient receiving a marketed pharmaceutical product or in a patient who is participating on a clinical trial who is receiving an investigational or non-investigational pharmaceutical agent. The AE does not necessarily have a causal relationship with the patient's treatment. Therefore, an AE can be any unfavorable and unintended sign, symptom, or disease temporally associated with the use of a medicinal product, whether or not considered to be related to the medicinal product. Many AEs may be related to progression of the patient's underlying malignancy. An AE includes, but is not limited to: an exacerbation of a pre-existing illness; an increase in frequency or intensity of a pre-existing episodic event or condition; a condition detected or diagnosed after study drug administration even though it may have been present prior to the start of the study; and continuously persistent disease or symptoms that were present at baseline and worsen following the start of the study. An AE generally does not include: medical or surgical procedures (e.g., surgery, endoscopy, tooth extraction, or transfusion); however, the condition that leads to the procedure is an adverse event; pre-existing diseases, conditions, or laboratory abnormalities present or detected at the start of the study that do not worsen; hospitalizations or procedures that are done for elective purposes not related to an untoward medical occurrence (e.g., hospitalizations for cosmetic or elective surgery or social/convenience admissions); the disease being studied or signs/symptoms associated with the disease unless more severe than expected for the patient's condition; and overdose of study drug without any clinical signs or symptoms.

A "serious adverse event" or (SAE) as used herein refers to any untoward medical occurrence at any dose including, but not limited to, that: a) is fatal; b) is life-threatening (defined as an immediate risk of death from the event as it occurred); c) results in persistent or significant disability or incapacity; d) requires in-patient hospitalization or prolongs an existing hospitalization (exception: Hospitalization for elective treatment of a pre-existing condition that did not worsen during the study is not considered an adverse event. Complications that occur during hospitalization are AEs and if a complication prolongs hospitalization, then the event is serious); e) is a congenital anomaly/birth defect in the offspring of a patient who received medication; or f) conditions not included in the above definitions that may jeopardize the patient or may require intervention to prevent one of the outcomes listed above unless clearly related to the patient's underlying disease. "Lack of efficacy" (progressive disease) is not considered an AE. The signs and symptoms or clinical sequelae resulting from lack of efficacy should be reported if they fulfill the AE or SAE definitions.

The following definitions may be used to evaluate response based on target lesions: "complete response" or "CR" refers to disappearance of all target lesions; "partial response" or "PR" refers to at least a 30% decrease in the sum of the longest diameters (SLD) of target lesions, taking as reference the baseline SLD; "stable disease" or "SD" refers to neither sufficient shrinkage of target lesions to qualify for PR, nor sufficient increase to qualify for PD, taking as reference the nadir SLD since the treatment started; "progressive disease" or "PD" refers to at least a 20% increase in the SLD of target lesions, taking as reference the nadir SLD recorded since the treatment started, or, the presence of one or more new lesions; "unable to evaluate" or "UE" refers to a target lesion present at baseline which was not measured or which was unable to be evaluated leading to an inability to determine the status of that particular tumor for the time point in question (if the SLD cannot be determined at a time point, and the rules for PD do not apply, a response of CR, PR or SD cannot be assigned for that time point and the time point response will be UE); "not applicable" or "NA" refers to no target lesions were identified at baseline (patients with no target lesions identified at baseline cannot be assessed for response. These patients will be assessed for progression only); and "not done" or "ND" refers to scans were not performed at this time point to evaluate the target lesions.

The following definitions of response assessments may be used to evaluate a non-target lesion: "complete response" or "CR" refers to disappearance of all non-target lesions; "stable disease" or "SD" refers to the persistence of one or more non-target lesions not qualifying for CR or PD; "progressive disease" or "PD" refers to the "unequivocal progression" of existing non-target lesion(s) or appearance of one or more new lesion(s) is considered progressive disease (if PD for the subject is to be assessed for a time point based solely on the progression of non-target lesion(s), then additional criteria are required to be fulfilled. In this instance, the lesion(s) upon which the assessment of PD is being made must be retrospectively assessed from baseline (or the nadir) and compared to the time point in question. PD of non-target lesion(s) in this instance may be assessed when the SLD of the lesion(s) has increased by 20% or greater and the lesion(s) measure greater than or equal to 10 mm in longest dimension (LD) at the time of progression. If the nontarget lesion(s) do not meet the quantitative criteria as described, they will not be assessed as having progressed. For pleural fluid, ascites, pericardial effusions and other fluid collections, progression will be assessed in an otherwise stable or responding subject when the increase in the fluid is estimated to be greater than 500 cc., and is not attributable to a benign cause identified radiographically); "unable to evaluate" or "UE" refers to any non-target lesion present at baseline which was not measured or was unable to be evaluated leading to an inability to determine the status of that particular tumor for the time point in question; "not applicable" or "NA" refers to no non-target lesions were identified at baseline; and "not done" or "ND" refers to scans were not performed at this time point to evaluate the non-target lesions.

As used herein, "at the time of starting treatment" or "baseline" refers to the time period at or prior to the first exposure to a treatment comprising a) a composition comprising nanoparticles comprising paclitaxel and an albumin; and b) a platinum-based agent. In some embodiments, "at the time of starting treatment" or "baseline" is about any of six months, three months, second months, one month, or days prior to a treatment comprising a) a composition comprising nanoparticles comprising paclitaxel and an albumin; and b) a platinum-based agent. In some embodiments, "at the time of starting treatment" is immediately prior to or coincidental with the first exposure to a treatment comprising a) a composition comprising nanoparticles comprising paclitaxel and an albumin; and b) a platinum-based agent.

As used herein, "based upon" includes assessing, determining, or measuring the patient characteristics as described herein (and preferably selecting a patient suitable for receiving treatment).

"Likely to respond" or "responsiveness" as used herein refers to any kind of improvement or positive response either clinical or non-clinical selected from, but not limited to, measurable reduction in tumor size or evidence of disease or disease progression, complete response, partial response, stable disease, increase or elongation of progression free survival, or increase or elongation of overall survival.

"Progression free survival" (PFS) indicates the length of time during and after treatment that the cancer does not grow. Progression-free survival includes the amount of time patients have experienced a complete response or a partial response, as well as the amount of time patients have experienced stable disease.

A "complete response" (CR) to a therapy defines patients with evaluable but non-measurable disease, whose tumor and all evidence of disease had disappeared.

A "partial response" (PR) to a therapy defines patients with anything less than complete response were simply categorized as demonstrating partial response.

"Stable disease" (SD) indicates that the patient is stable.

When a patient's health-related quality of life "is used as a basis" for administration of the treatment methods described herein, or selection for the treatment methods described herein, the patient's health-related quality of life or limitations is evaluated before and/or during treatment, and the conclusions obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment (s); (e) probable or likely unsuitability of an individual to continue to receive treatment(s); (f) adjusting dosage; or (g) predicting likelihood of clinical benefits. As would be well understood by one in the art, an evaluation of a patient's health-related quality of life in a clinical setting is a clear indication that this parameter was used as a basis for initiating, continuing, adjusting and/or ceasing administration of the treatments described herein.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

As is apparent to one skilled in the art, an individual assessed, selected for, and/or receiving treatment is an individual in need of such activities.

Methods of Treating NSCLC

The present invention provides methods of treating NSCLC in an individual (e.g., human) comprising administering to the individual a) an effective amount of a composition comprising nanoparticles comprising paclitaxel and an albumin; and b) an effective amount of a platinum-based agent.

The methods herein are applicable to multiple histological types of NSCLC. The NSCLC may be squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments the NSCLC is squamous cell carcinoma. In some embodiments, the squamous cell carcinoma is papillary, clear cell, small cell, or basaloid. In some embodiments, the NSCLC is adenocarcinoma. In some embodiments, the adenocarcinoma is acinar, papillary, bronchioloalveolar carcinoma (e.g., nonmucinous, mucinous, mixed mucinous and nonmucinous or indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, or clear cell adenocarcinoma. In some embodiments, the large cell carcinoma is large-cell neuroendocrine carcinoma, combined large-cell neuroendocrine carcinoma, basaloid carcinoma, lymphoepithelioma-like carcinoma, clear cell carcinoma, or large cell carcinoma with rhabdoid phenotype. In some embodiments, the carcinoma with pleomorphic, sarcomatoid, or sarcomatous elements is carcinomas with spindle and/or giant cells, spindle cell carcinoma, giant cell carcinoma, carcinosarcoma, or pulmonary blastoma. In some embodiments, the carcinoma of salivary-gland type is mucoepidermoid carcinoma or adenoid cystic carcinoma.

The NSCLC of any of the methods herein may be an occult tumor, a stage 0 tumor, a stage I tumor (stage IA (T1, N0, M0) or stage IB (T2, N0, M0)), a stage II tumor (stage IIA (T1, N1, M0) and stage IIB (T2, N1, M0)), a stage IIIA tumor (T1, N2, M0, T2, N2, M0, T3, N1, M0, or T3, N2, M0), a stage IIIB tumor (Any T, N3, M0 or T4, any N, M0), or a stage IV tumor (Any T, any N, M1). In some embodiments of any of the methods described herein, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable. In some embodiments, the NSCLC is unresectable stage IV NSCLC. In some embodiments, the NSCLC is inoperable Stage IIIA and/or IIIB NSCLC, PS 0-1, and FEV 1>800 ml.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

In some embodiments of any of the methods described herein, the composition comprises nanoparticles comprising paclitaxel and an albumin (such as human serum albumin), wherein paclitaxel in the nanoparticles is coated with the albumin. In some embodiments, the average particle size of the nanoparticles in the composition is no greater than about 200 nm (such as less than about 200 nm). In some embodiments, the composition comprises Nab-paclitaxel (Abraxane®). In some embodiments, the composition is the Nab-paclitaxel (Abraxane®). In some embodiments, the nanoparticle composition and the platinum-based agent have synergistic effect on treating NSCLC.

Platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the effective amount of the composition comprising nanoparticles comprising paclitaxel and the albumin is between about 50 to about 125 mg/m$^2$ (e.g., 50 mg/m$^2$, 75 mg/m$^2$, or 100 mg/m$^2$) and the effective amount of the platinum-based agent is between about AUC=2 to about AUC=6 (e.g., AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the effective amount of the composition comprising nanoparticles comprising paclitaxel and the albumin is between about 50 to about 125 mg/m$^2$ administered weekly and the effective amount of the platinum-based agent is between about AUC=2 to about AUC=6 administered once every three weeks. In some embodiments, the effective amount of the composition comprising nanoparticles comprising paclitaxel and the albumin is about 100 mg/m$^2$ administered weekly and the effective amount of the platinum-based agent is about AUC=6 administered once every three weeks. In some embodiments, the effective amount of the composition comprising nanoparticles comprising paclitaxel and the albumin is about 75 mg/m$^2$ administered weekly and the effective amount of the platinum-based agent is about AUC=4.5 administered once every three weeks. In some embodiments, the effective amount of the composition comprising nanoparticles comprising paclitaxel and the albumin is about 50 mg/m$^2$ administered weekly and the effective amount of the platinum-based agent is about AUC=3 administered once every three weeks. In some embodiments, the effective amount of the composition comprising nanoparticles comprising paclitaxel and the albumin is about 40 mg/m$^2$ administered weekly and the effective amount of the platinum-based agent is about AUC=2 administered weekly. In some embodiments, the paclitaxel nanoparticle composition and/or the platinum-based agent is administered intravenously. In some embodiments, the paclitaxel nanoparticle composition and the platinum-based agent are administered intravenously.

In some embodiments, the composition comprising nanoparticles comprising paclitaxel and the albumin and the platinum-based agent are sequentially administered; concurrently administered or simultaneously administered.

In some embodiments, the composition comprising nanoparticles comprising paclitaxel and albumin is administered without any steroid premedication and/or without G-CSF prophylaxis.

For example, methods are provided for treating NSCLC in an individual in need thereof, comprising administering to the individual (a) an effective amount of a composition comprising nanoparticles comprising paclitaxel and albumin; and (b) an effective amount of platinum-based agent, wherein the effective amount of the composition comprising nanoparticles comprising paclitaxel and albumin is 100 mg/m$^2$ administered weekly and the effective amount of a platinum-based agent is AUC=6. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual in need thereof, comprising administering to the individual (a) an effective amount of a composition comprising nanoparticles comprising paclitaxel coated with albumin; and (b) an effective amount of platinum-based agent, wherein the effective amount of the composition comprising nanoparticles comprising paclitaxel coated with albumin is 100 mg/m$^2$ administered weekly and the effective amount of a platinum-based agent is AUC=6. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods of treating NSCLC in an individual in need thereof, comprising administering to the individual (a) an effective amount of a composition comprising nanoparticles comprising paclitaxel and albumin, wherein the average size of the nanoparticles in the nanoparticle composition is no greater than about 200 nm; and (b) an effective amount of platinum-based agent, wherein the effective amount of the composition comprising nanoparticles comprising paclitaxel and albumin is 100 mg/m$^2$ administered weekly and the effective amount of a platinum-based agent is AUC=6. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual in need thereof, comprising administering to the individual (a) an effective amount of a composition comprising nanoparticles comprising paclitaxel coated with albumin, wherein the average size of the nanoparticles in the nanoparticle composition is no greater than about 200 nm; and (b) an effective amount of platinum-based agent, wherein the effective amount of the composition comprising nanoparticles comprising paclitaxel coated with albumin is 100 mg/m$^2$ administered weekly and the effective amount of a platinum-based agent is AUC=6. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual in need thereof, comprising administering to the individual (a) an effective amount of Nab-paclitaxel (Abraxane®); and (b) an effective amount of platinum-based agent, wherein the effective amount of the Nab-paclitaxel (Abraxane®) is 100 mg/m$^2$ administered weekly and the effective amount of a platinum-based agent is AUC=6. In some embodiments, the Nab-paclitaxel (Abraxane®) is administered weekly and the platinum-based agent is administered once every three weeks. In some embodiments, Nab-paclitaxel (Abraxane®) and the platinum-based agent are administered intravenously. In some embodiments NSCLC is advanced NSCLC. In some embodiments, the method is used as first-line therapy. In some embodiments, the platinum based agent is carboplatin. In some embodiments, the NSCLC is squamous cell carcinoma.

In some embodiments, there are provided methods for treating NSCLC in an individual in need thereof, comprising administering to the individual (a) an effective amount of Nab-paclitaxel (Abraxane®); and (b) an effective amount of carboplatin, wherein the effective amount of the Nab-paclitaxel (Abraxane®) is 100 mg/m$^2$ administered weekly and the effective amount of carboplatin is AUC=6. In some embodiments, the Nab-paclitaxel (Abraxane®) is administered weekly and the carboplatin is administered once every three weeks. In some embodiments, Nab-paclitaxel (Abraxane®) and the carboplatin are administered intravenously. In some embodiments NSCLC is advanced NSCLC. In some embodiments, the method is used as first-line therapy. In some embodiments, the NSCLC is squamous cell carcinoma.

Also provided are methods of treating NSCLC in an individual in need thereof, comprising administering to the individual a) an effective amount of a composition comprising nanoparticles comprising paclitaxel and an albumin and b) an effective amount of a platinum-based agent, wherein the NSCLC is squamous cellular carcinoma. In some embodiments, the effective amount of the composition comprising nanoparticles comprising paclitaxel and albumin is 100 mg/m$^2$ administered weekly and the effective amount of a platinum-based agent is AUC=6. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual in need thereof, comprising administering to the individual a) an effective amount of a composition comprising nanoparticles comprising paclitaxel coated with albumin and b) an effective amount of a platinum-based agent, wherein the NSCLC is squamous cellular carcinoma. In some embodiments, the effective amount of the composition comprising nanoparticles comprising paclitaxel coated with albumin is 100 mg/m$^2$ administered weekly and the effective amount of a platinum-based agent is AUC=6. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual in need thereof, comprising administering to the individual a) an effective amount of a composition comprising nanoparticles comprising paclitaxel and an albumin, wherein the average size of the nanoparticles in the nanoparticle composition is no greater than about 200 nm, and b) an effective amount of a platinum-based agent, wherein the NSCLC is squamous cellular carcinoma. In some embodiments, the effective amount of the composition comprising nanoparticles comprising paclitaxel and albumin is 100 mg/m$^2$ administered weekly and the effective amount of a platinum-based agent is AUC=6. In some embodiments, the composition comprising nanoparticles comprising paclitaxel and albumin is administered weekly and the platinum-based agent is administered once every three weeks. In some embodiments, the composition comprising nanoparticles comprising paclitaxel and albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual in need thereof, comprising administering to the individual a) an effective amount of a composition comprising nanoparticles comprising paclitaxel coated with albumin, wherein the average size of the nanoparticles in the nanoparticle composition is no greater than about 200 nm, and b) an effective amount of a platinum-based agent, wherein the NSCLC is squamous cellular carcinoma. In some embodiments, the effective amount of the composition comprising nanoparticles comprising paclitaxel coated with albumin is 100 mg/m$^2$ administered weekly and the effective amount of a platinum-based agent is AUC=6. In some embodiments, the composition comprising nanoparticles comprising paclitaxel coated with albumin is administered weekly and the platinum-based agent is administered once every three weeks. In some embodiments, the composition comprising nanoparticles comprising paclitaxel coated with albumin and the platinum-based agent are administered intravenously. In some embodiments NSCLC is advanced NSCLC. In some embodiments, the method is used as first-line therapy. In some embodiments, the platinum based agent is carboplatin.

In some embodiments, there are provided methods of treating NSCLC in an individual in need thereof, comprising administering to the individual a) an effective amount of Nab-paclitaxel (Abraxane®) and b) an effective amount of a platinum-based agent, wherein the NSCLC is squamous cellular carcinoma. In some embodiments, the effective amount of Nab-paclitaxel (Abraxane®) is 100 mg/m$^2$ administered weekly and the effective amount of a platinum-based agent is AUC=6. In some embodiments, the Nab-paclitaxel (Abraxane®) is administered weekly and the platinum-based agent is administered once every three weeks. In some embodiments, the Nab-paclitaxel (Abraxane®) and the platinum-based agent are administered intravenously. In some embodiments NSCLC is advanced NSCLC. In some embodiments, the method is used as first-line therapy.

In some embodiments, there are provided methods of treating NSCLC in an individual in need thereof, comprising administering to the individual a) an effective amount of Nab-paclitaxel (Abraxane®) and b) an effective amount of carboplatin, wherein the NSCLC is squamous cellular carcinoma. In some embodiments, the effective amount of Nab-paclitaxel (Abraxane®) is 100 mg/m$^2$ administered weekly and the effective amount of carboplain is AUC=6. In some embodiments, the Nab-paclitaxel (Abraxane®) is administered weekly and the carboplatin is administered once every three weeks. In some embodiments, the Nab-paclitaxel (Abraxane®) and the carboplain are administered intravenously. In some embodiments NSCLC is advanced NSCLC. In some embodiments, the method is used as first-line therapy.

In some embodiments of any of the methods, the methods for treating NSCLC further comprise radiation. In some embodiments, the methods further comprise thoracic radiation. For example, methods of treating NSCLC in an individual (e.g., human) may comprise administering to the individual a) an effective amount of a composition comprising nanoparticles comprising paclitaxel and an albumin (such as nanoparticles comprising paclitaxel coated with albumin, for example Nab-paclitaxel (Abraxane®)); b) an effective amount of a platinum-based agent (such as carboplain), and c) radiation (e.g. thoracic radiation). In some embodiments, the effective amount of the composition comprising nanoparticles comprising paclitaxel and albumin is between 20 mg/m$^2$ to about 60 mg/m$^2$ (e.g., 40 mg/m$^2$), administered weekly, the effective amount of a platinum-based agent is between about AUC=2 to AUC=6 (e.g., AUC=2), and the thoracic radiation is between about 25 to about 40 (e.g., about 33) fractions by either 3D conformal or intensity-modulated techniques. In some embodiments, the composition comprising nanoparticles comprising paclitaxel and albumin is administered weekly and the platinum-based agent is administered weekly. In some embodiments, the treatment time is seven weeks and the thoracic radiation is concurrent. In some embodiments, the composition comprising nanoparticles comprising paclitaxel and albumin and the platinum-based agent are administered intravenously. In some embodiments, the method of treating NSCLC in an individual (e.g., human) comprising administering to the individual a) an effective amount of a composition comprising nanoparticles comprising paclitaxel and an albumin (such as nanoparticles comprising paclitaxel coated with albumin, for example Nab-paclitaxel (Abraxane®); b) an effective amount of a platinum-based agent (such as carboplain), and c) radiation (e.g. thoracic radiation) further comprises a consolidation therapy. In some embodiments, the consolidation therapy comprises administering to the individual a) an effective amount of a composition comprising nanoparticles comprising paclitaxel and an albumin (such as nanoparticles comprising paclitaxel coated with albumin, for example Nab-paclitaxel (Abraxane®)) and b) an effective amount of a platinum-based agent (such as carboplain). In some embodiments of the consolidation therapy, the effective amount of the composition comprising nanoparticles comprising paclitaxel and albumin is between about 50 to about 125 mg/m$^2$ (e.g., 50 mg/m$^2$, 75 mg/m$^2$, or 100 mg/m$^2$) administered weekly and the effective amount of a platinum-based agent is between about AUC=2 and about AUC=6 (e.g., AUC=3, AUC=4.5, or AUC=6). In some embodiments, the composition comprising nanoparticles comprising paclitaxel and albumin is administered weekly and the platinum-based agent is administered once every three weeks. In some embodiments, the consolidation therapy comprises two cycles. In some embodiments, the composition comprising nanoparticles comprising paclitaxel and albumin and the platinum-based agent are administered intravenously. In some embodiments NSCLC is inoperable Stage IIIA and/or IIIB NSCLC. In some embodiments, the NSCLC is inoperable Stage IIIA and/or IIIB NSCLC, PS 0-1, and FEV 1>800 ml. In some embodiments, the platinum based agent is carboplatin.

Further provided herein are methods of treating NSCLC in an individual (e.g., human) comprising administering to the individual a) an effective amount of a composition comprising nanoparticles comprising paclitaxel and an albumin (such as nanoparticles comprising paclitaxel coated with albumin, for example Nab-paclitaxel (Abraxane®)), and b) an effective amount of radiation (e.g. thoracic radiation). In some embodiments, the effective amount of the composition comprising nanoparticles comprising paclitaxel and albumin is between 20 mg/m$^2$ to about 60 mg/m$^2$ (e.g., 40 mg/m$^2$), administered weekly and the thoracic radiation is between about 25 to about 40 (e.g., about 33) fractions by either 3D conformal or intensity-modulated techniques. In some embodiments, the treatment time is seven weeks and the thoracic radiation is concurrent. In some embodiments, the composition comprising nanoparticles comprising paclitaxel and albumin and the platinum-based agent are administered intravenously. In some embodiments, the composition comprising nanoparticles comprising paclitaxel and albumin are administered intravenously. In some embodiments NSCLC is inoperable Stage IIIA and/or IIIB NSCLC. In some embodiments, the NSCLC is inoperable Stage IIIA and/or IIIB NSCLC, PS 0-1, and FEV 1>800 ml.

Further provided herein are methods of treating NSCLC in an individual (e.g., human) comprising administering to the individual a) an effective amount of a composition comprising nanoparticles comprising paclitaxel and an albumin (such as nanoparticles comprising paclitaxel coated with albumin, for example Nab-paclitaxel (Abraxane®)), and b) an effective amount of radiation (e.g. thoracic radiation). In some embodiments, the effective amount of the composition comprising nanoparticles comprising paclitaxel and albumin is between 20 mg/m$^2$ to about 60 mg/m$^2$ (e.g., 40 mg/m$^2$), administered weekly and the thoracic radiation is between about 25 to about 40 (e.g., about 33) fractions by either 3D conformal or intensity-modulated techniques. In some embodiments, the treatment time is seven weeks and the thoracic radiation is concurrent. In some embodiments, the composition comprising nanoparticles comprising paclitaxel and albumin and the platinum-based agent are administered intravenously. In some embodiments, the composition comprising nanoparticles comprising paclitaxel and albumin are administered intravenously. In some embodiments NSCLC is inoperable Stage IIIA and/or IIIB NSCLC. In some embodiments, the NSCLC is inoperable Stage IIIA and/or IIIB NSCLC, PS 0-1, and FEV 1>800 ml.

The methods described herein are useful for various aspects of NSCLC treatment. In some embodiments of any of the methods, the method comprises a method of inhibiting NSCLC cell proliferation (such as NSCLC tumor growth) in an individual, comprising administering to the individual a) an effective amount of a composition comprising nanoparticles comprising paclitaxel and an albumin and b) an effective amount of a platinum-based agent. In some embodiments, at least about 10% (including for example at least about any of 20%, 30%, 40%, 60%, 70%, 80%, 90%, or 100%) cell proliferation is inhibited.

In some embodiments of any of the methods, the method comprises a method of inhibiting NSCLC tumor metastasis in an individual, comprising administering to the individual a) an effective amount of a composition comprising nanoparticles comprising paclitaxel and an albumin and b) an effective amount of a platinum-based agent. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided.

In some embodiments of any of the methods, the method comprises a method of reducing NSCLC tumor size in an individual, comprising administering to the individual an effective amount of a) an effective amount of a composition comprising nanoparticles comprising paclitaxel and an albumin and b) an effective amount of a platinum-based agent. In some embodiments, the tumor size is reduced at least about 10% (including for example at least about any of 20%, 30%, 40%, 60%, 70%, 80%, 90%, or 100%).

In some embodiments of any of the methods, the method comprises a method of prolonging progression-free survival of NSCLC in an individual, comprising administering to the individual a) an effective amount of a composition comprising nanoparticles comprising paclitaxel and an albumin and b) an effective amount of a platinum-based agent. In some embodiments, the method prolongs the time to disease progression by at least any of 1, 2, 3, 4, 5, 6, 7, 8, 9, 10, 11, or 12 weeks.

In some embodiments of any of the methods, the method comprises a method of prolonging survival of an individual having NSCLC, comprising administering to the individual a) an effective amount of a composition comprising nanoparticles comprising paclitaxel and an albumin and b) an effective amount of a platinum-based agent. In some embodiments, the method prolongs the survival of the individual by at least any of 1, 2, 3, 4, 5, 6, 7, 8, 9, 10, 11, 12, 18, or 24 month.

In some embodiments of any of the methods, the method comprises a method of alleviating one or more symptoms in an individual having NSCLC, comprising administering to the individual a) an effective amount of a composition comprising nanoparticles comprising paclitaxel and an albumin and b) an effective amount of a platinum-based agent.

In some embodiments of any of the methods, the method comprises a method of reducing AEs and SAEs in an individual having NSCLC, comprising administering to the individual a) a composition comprising nanoparticles comprising paclitaxel and an albumin and b) a platinum-based agent, wherein the reduction is based on a comparison with the AEs and SAEs resulting from administering to the individual a) Taxol® and b) a platinum-based agent.

In some embodiments of any of the methods described herein, the method of treatment results in an objective response (such as a partial response or complete response).

In some embodiments of any of the methods described herein, the method of treatment results in improved quality of life.

In some embodiments of any of the methods described herein, an individual (e.g., human) who has been diagnosed with or is suspected of having NSCLC can be treated. In some embodiments, the individual is human. In some embodiments, the individual is at least about any of 35, 40, 45, 50, 55, 60, 65, 70, 75, 80, or 85 years old. In some embodiments, the individual is male. In some embodiments, the individual is a female. In some embodiments, the individual has any of the types of NSCLC described herein. In some embodiments, the individual has a single lesion at presentation. In some embodiments, the individual has multiple lesions at presentation. In some embodiments, the individual is resistant to treatment of NSCLC with other agents (such as a non-nanoparticle formulation of taxane, e.g., Taxol® or Taxotere®). In some embodiments, the individual is initially responsive to treatment of NSCLC with other agents (such as a non-nanoparticle formulation of taxane, e.g., Taxol® or Taxotere®) but has progressed after treatment.

In some embodiments of any of the methods, the methods further include administration of an effective amount of an anti-angiogenic agent (e.g., angiogenesis inhibitor). In some embodiments, the anti-angiogenic agent is bevacizumab, sunitinib, or sorafenib tosylate. In some embodiments, the anti-angiogenic agent is bevacizumab. In some embodiments, the effective amount of bevacizumab is between about 5 mg/kg and about 15 mg/kg. In some embodiments, the effective amount of bevacizumab is about any of 5 mg/kg, 7.5 mg/kg, 10 mg/kg, or 15 mg/kg.

In some embodiments, a lower amount of each pharmaceutically active compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. For example, the use of a small amount of pharmaceutically active compound may result in a reduction in the number, severity, frequency, or duration of one or more side-effects associated with the compound.

The methods described herein can be used for any one or more of the following purposes: alleviating one or more symptoms of NSCLC, delaying progressing of NSCLC, shrinking tumor size in NSCLC patient, inhibiting NSCLC tumor growth, prolonging overall survival, prolonging progression free survival, preventing or delaying NSCLC tumor metastasis, reducing (such as eradiating) preexisting NSCLC tumor metastasis, reducing incidence or burden of preexisting NSCLC tumor metastasis, or preventing recurrence of NSCLC.

In some embodiments of any of the methods described herein, the individual is a human who exhibits one or more symptoms associated with NSCLC. In some of embodiments, the individual is genetically or otherwise predisposed (e.g., having a risk factor) to developing NSCLC. These risk factors include, but are not limited to, age, sex, race, diet, history of previous disease, presence of precursor disease, genetic (e.g., hereditary) considerations, and environmental exposure (e.g., cigarette, pipe, or cigar smoking, exposure to second-hand smoke, radon, arsenic, asbestos, chromates, chloromethyl ethers, nickel, polycyclic aromatic hydrocarbons, radon progeny, other agents, or air pollution). In some embodiments, the individuals at risk for NSCLC include, e.g., those having relatives who have experienced NSCLC, and those whose risk is determined by analysis of genetic or biochemical markers.

Also provided are methods of treating NSCLC in an individual comprising administering to the individual a) an effective amount of a composition comprising nanoparticles comprising paclitaxel and an albumin and b) an effective amount of a platinum-based agent, wherein treatment is based upon the NSCLC having one or more (such as any of 1, 2, 3, 4, 5, 6, 7, 8, 9, 10, 11, or 12) characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Further provided herein are methods of treating NSCLC in an individual provided that the NSCLC has been found to have one or more (such as any of 1, 2, 3, 4, 5, 6, 7, 8, 9, 10, 11, or 12) characteristics selected from the group consisting of (a) squamous cellular carcinoma, (b) differential levels of caveolin-1 (CAV1), (c) differential levels of SPARC, (d)

differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake, the treatment comprising administering to the individual i) an effective amount of a composition comprising nanoparticles comprising paclitaxel and an albumin and ii) an effective amount of a platinum-based agent.

Provided herein are also methods of treating NSCLC, comprising: (a) selecting an individual having NSCLC, wherein the NSCLC has one or more (such as any of 1, 2, 3, 4, 5, 6, 7, 8, 9, 10, 11, or 12) characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (b) administering to the individual thus selected i) an effective amount of a composition comprising nanoparticles comprising paclitaxel and an albumin and ii) an effective amount of a platinum-based agent.

Methods are also provided herein of assessing whether an individual with NSCLC will respond to treatment comprising assessing one or more (such as any of 1, 2, 3, 4, 5, 6, 7, 8, 9, 10, 11, or 12) characteristics of the NSCLC selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake, wherein one or more of the characteristics of the NSCLC indicates the individual will be responsive to the treatment and the treatment comprises i) an effective amount of a composition comprising nanoparticles comprising paclitaxel and an albumin and ii) an effective amount of a platinum-based agent.

In addition, methods are provided herein of identifying an individual with NSCLC likely to respond to treatment comprising a) a composition comprising nanoparticles comprising paclitaxel and an albumin and b) a platinum-based agent comprising: (A) assessing one or more (such as any of 1, 2, 3, 4, 5, 6, 7, 8, 9, 10, 11, or 12) characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (B) identifying the individual having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

Provided herein are also methods for marketing a combination therapy comprising a) a composition comprising nanoparticles comprising paclitaxel and an albumin and b) a platinum-based agent for use in a NSCLC individual subpopulation, the methods comprising informing a target audience about the use of the combination therapy for treating the individual subpopulation characterized by the individuals of such subpopulation having one or more (such as any of 1, 2, 3, 4, 5, 6, 7, 8, 9, 10, 11, or 12) characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

In some embodiments of any of the methods, the one or more characteristics of NSCLC include 1, 2, 3, 4, 5, 6, 7, 8, 9, 10, 11, or 12 characteristics of NSCLC. In some embodiments, the one or more characteristics include, for example, at least two or more characteristics, at least three or more characteristics, at least four or more characteristics, or at least five or more characteristics. For example, in some embodiments, the NSCLC is characterized by differentially levels of CAV-1 and squamous cellular carcinoma. In some embodiments, the NSCLC is characterized by differential levels of CAV-1, squamous cellular carcinoma, and differential levels of SPARC. In some embodiments, the NSCLC is characterized by differential levels of CAV-1, squamous cellular carcinoma, differential levels of SPARC, and differential levels of hypoxia markers. In some embodiments, the NSCLC is characterized by (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

The differential levels of tumor acidity may be evidenced by, for example, differential levels of carbonic anhydrase-9 (CA-9) and/or differential levels of LDH (e.g., LDH-5).

The differential levels of hypoxia markers may be evidenced by, for example, differential levels of HIF-1α, differential levels of HIF-2α, and/or differential levels of differentiated embryo-chrondrocyte expressed gene 1 (DEC-1).

In some embodiments, the one or more characteristics of NSCLC comprises differential levels of SPARC. SPARC (Secreted Protein, Acidic and Rich in Cysteine) is a matricellular protein upregulated in several aggressive cancers. See Porter et al., *J. Histochem. Cytochem.* 1995; 43:791. The human SPARC gene encodes a 303 amino acid SPARC proteins, while mature SPARC is a 285 amino acid glycoprotein. After cleavage of the signal sequence a 32-kD secreted form is produced which migrates at 43 kD on SDA-PAGE because of glycosylation. In some embodiments, differential levels is determined in tumor tissue, normal tissue adjacent to said tumor, normal tissue distal to said tumor or peripheral blood lymphocytes. In some embodiments, the drug uptake capability is based on the level of SPARC on the tumor stroma.

In some embodiments of any of the methods, differential levels are determined in tumor tissue, normal tissue adjacent to said tumor, normal tissue distal to said tumor or peripheral blood lymphocytes.

"Differential levels" or "differential" as applied to a gene, may refer to a variance in the nucleic acid sequence, methylation state or degree of methylation, or production of the nucleic acid transcribed from the gene or the protein product encoded by the gene. In some embodiments, a differentially expressed gene may be over expressed (high expression) or under expressed (low expression) as compared to the expression level of a normal or control cell, a given patient population, or with an internal control. In some embodiments, the differential is about any of 1.5 times, 2.0 times, 2.5 times, 3.0 times, 5.0 times, 10 times, 50 times, or 100 times higher than the expression level detected in a control sample. In some embodiments, the differential is about any of 1.5 times, 2.0 times, 2.5 times, 3.0 times, 5.0 times, 10 times, 50 times, or 100 times lower than the expression level detected in a control sample. In some embodiments, the nucleotide sequences in a cell or tissue which are expressed where silent in a control cell or not expressed where expressed in a control cell.

In some embodiments, expression level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression of the gene of interest. Alternatively, if the expression level of a gene of interest for the single patient is determined to be below the median expression level of the patient population, that patient is determined to have low expression of the gene of interest. In some embodiments, the single patient has NSCLC and the patient population does not have cancer (i.e., normal). In some embodiments, the single patient has one histological type of NSCLC (e.g., squamous cell carcinoma) and the patient population has a second histological type of NSCLC (e.g., adenocarcinoma). In some embodiments, the single patient and the patient population have the same histological type of NSCLC (e.g., squamous cell carcinoma).

To practice this method, the sample is a patient sample containing the tumor tissue, normal tissue adjacent to said tumor, normal tissue distal to said tumor or peripheral blood lymphocytes. Sample nucleic acid for use in the above-described methods can be obtained from any cell type or tissue of a subject. For example, a subject's bodily fluid (e.g. blood) can be obtained by known techniques (e.g., venipuncture). Alternatively, tests can be performed on dry samples (e.g., hair or skin).

In some embodiments, the method comprises isolating a sample containing the genetic material to be tested. In some embodiments, the method comprises determining differential levels in situ. Accordingly, the methods of this application are not to be limited to requiring isolation of the genetic material prior to analysis.

These methods to identify expression levels are not limited by the technique that is used to identify the expression level of the gene of interest. Nucleic acid (e.g., RNA or DNA) or protein levels of the gene of interest can be measured. Methods for measuring gene expression and/or determining sequence for detection of polymorphism are well known in the art and include, but are not limited to, immunological assays, nuclease protection assays, northern blots, in situ hybridization, ELISA, reverse transcriptase Polymerase Chain Reaction (RT-PCR), Real-Time Polymerase Chain Reaction, expressed sequence tag (EST) sequencing, cDNA microarray hybridization or gene chip analysis, subtractive cloning, Serial Analysis of Gene Expression (SAGE), Massively Parallel Signature Sequencing (MPSS), and Sequencing-By-Synthesis (SBS). Diagnostic procedures can also be performed in situ directly upon tissue sections (fixed and/or frozen) of patient tissue obtained from biopsies or resections.

Amplification of polynucleotides includes methods such as PCR, ligation amplification (or ligase chain reaction, LCR) and amplification methods. These methods are known and widely practiced in the art. In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

In some embodiments of any of the methods herein, the methods result in a measurable reduction in tumor size or evidence of disease or disease progression, complete response, partial response, stable disease, increase or elongation of progression free survival, or increase or elongation of overall survival. In some embodiments of any of the methods above, a patient is likely to respond as evident by a measurable reduction in tumor size or evidence of disease or disease progression, complete response, partial response, stable disease, increase or elongation of progression free survival, increase or elongation of overall survival. In some embodiments, at least about 10% (including for example at least about any of 20%, 30%, 40%, 60%, 70%, 80%, 90%, or 100%) cell proliferation is inhibited. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided. In some embodiments, the tumor size is reduced at least about 10% (including for example at least about any of 20%, 30%, 40%, 60%, 70%, 80%, 90%, or 100%). In some embodiments, the method prolongs the progression free survival by at least any of 1, 2, 3, 4, 5, 6, 7, 8, 9, 10, 11, or 12 weeks. In some embodiments, the method prolongs the progression free survival of the individual by at least any of 1, 2, 3, 4, 5, 6, 7, 8, 9, 10, 11, 12, 18, or 24 month. In some embodiments, the method prolongs the survival of the individual by at least any of 1, 2, 3, 4, 5, 6, 7, 8, 9, 10, 11, 12, 18, or 24 month.

In some embodiments of any of the methods herein, the methods result in improved quality of life.

The methods herein are applicable to multiple histological types of NSCLC. The NSCLC may squamous cell carcinoma (i.e., epidermoid carcinoma), large cell carcinoma, adenocarcinoma, adenosquamous carcinoma, carcinomas with pleomorphic, sarcomatoid, or sarcomatous elements, carcinoid tumor, or salivary gland carcinoma. In some embodiments the NSCLC is squamous cell carcinoma. In some embodiments, the squamous cell carcinoma is papillary, clear cell, small cell, or basaloid. In some embodiments, the NSCLC is adenocarcinoma. In some embodiments, the adenocarcinoma is acinar, papillary, bronchioloalveolar carcinoma (e.g., nonmucinous, mucinous, mixed mucinous and nonmucinous or indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, or clear cell adenocarcinoma. In some embodiments, the large cell carcinoma is large-cell neuroendocrine carcinoma, combined large-cell neuroendocrine carcinoma, basaloid carcinoma, lymphoepithelioma-like carcinoma, clear cell carcinoma, or large cell carcinoma with rhabdoid phenotype. In some embodiments, the carcinoma with pleomorphic, sarcomatoid, or sarcomatous elements is carcinomas with spindle and/or giant cells, spindle cell carcinoma, giant cell carcinoma, carcinosarcoma, or pulmonary blastoma. In some embodiments, the carcinoma of salivary-gland type is mucoepidermoid carcinoma or adenoid cystic carcinoma.

The NSCLC of any of the methods herein may be an occult tumor, a stage 0 tumor, a stage I tumor (stage IA (T1, N0, M0) or stage IB (T2, N0, M0)), a stage II tumor (stage IIA (T1, N1, M0) and stage IIB (T2, N1, M0)), a stage IIIA tumor (T1, N2, M0, T2, N2, M0, T3, N1, M0, or T3, N2, M0), a stage IIIB tumor (Any T, N3, M0 or T4, any N, M0), or a stage IV tumor (Any T, any N, M1). In some embodiments of any of the methods described herein, the NSCLC is early stage NSCLC, non-metastatic NSCLC, primary NSCLC, advanced NSCLC, locally advanced NSCLC, metastatic NSCLC, NSCLC in remission, or recurrent NSCLC. In some embodiments, the NSCLC is localized resectable, localized unresectable, or unresectable.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first-line therapy. In some embodiments, the method is used as a second-line therapy.

In some embodiments of any of the methods described herein, the composition comprising nanoparticles comprising paclitaxel and an albumin (such as human serum albumin), wherein paclitaxel in the nanoparticles is coated with the albumin. In some embodiments, the average particle size of the nanoparticles in the composition is no greater than about 200 nm (such as less than about 200 nm). In some embodiments, the composition comprises Nab-paclitaxel (Abraxane®). In some embodiments, the composition is the Nab-paclitaxel (Abraxane®). In some embodiments, the nanoparticle composition and the platinum-based agent have synergistic effect on treating NSCLC.

Platinum-based agent binds covalently to DNA and cross-links strands, inhibits DNA synthesis, and/or inhibits transcript. In some embodiments, the platinum-based agent is carboplatin, cisplatin, or oxaliplatin. In some embodiments, the platinum-based agent is carboplatin. In some embodiments, the platinum-based agent is cisplatin.

In some embodiments, the effective amount of the composition comprising nanoparticles comprising paclitaxel and the albumin is between about 40 to about 125 mg/m$^2$ or between about 50 to about 125 mg/m$^2$ (e.g., 40 mg/m$^2$, 50 mg/m$^2$, 60 mg/m$^2$, 75 mg/m$^2$, or 100 mg/m$^2$) and the effective amount of the platinum-based agent is between about AUC=2 to about AUC=6 (e.g., AUC=2, AUC=3, AUC=4.5, or AUC=6). In some embodiments, the effective amount of the composition comprising nanoparticles comprising paclitaxel and the albumin is administered weekly and the effective amount of the platinum-based agent is administered every three weeks. In some embodiments, the effective amount of the composition comprising nanoparticles comprising paclitaxel and the albumin is administered weekly and the effective amount of the platinum-based agent is administered weekly. In some embodiments, the effective amount of the composition comprising nanoparticles comprising paclitaxel and the albumin is between about 50 to about 125 mg/m$^2$ administered weekly and the effective amount of the platinum-based agent is between about AUC=2 to about AUC=6 administered once every three weeks. In some embodiments, the effective amount of the composition comprising nanoparticles comprising paclitaxel and the albumin is between about 40 to about 125 mg/m$^2$ administered weekly and the effective amount of the platinum-based agent is between about AUC=2 to about AUC=6 administered weekly. In some embodiments, the effective amount of the composition comprising nanoparticles comprising paclitaxel and the albumin is about 100 mg/m$^2$ administered weekly and the effective amount of the platinum-based agent is about AUC=6 administered once every three weeks. In some embodiments, the effective amount of the composition comprising nanoparticles comprising paclitaxel and the albumin is about 75 mg/m$^2$ administered weekly and the effective amount of the platinum-based agent is about AUC=4.5 administered once every three weeks. In some embodiments, the effective amount of the composition comprising nanoparticles comprising paclitaxel and the albumin is about 50 mg/m$^2$ administered weekly and the effective amount of the platinum-based agent is about AUC=3 administered once every three weeks. In some embodiments, the effective amount of the composition comprising nanoparticles comprising paclitaxel and the albumin is about 40 mg/m$^2$ administered weekly and the effective amount of the platinum-based agent is about AUC=2 administered weekly. In some embodiments, the paclitaxel nanoparticle composition and/or the platinum-based agent is administered intravenously. In some embodiments, the paclitaxel nanoparticle composition and the platinum-based agent are administered intravenously.

In some embodiments of any of the methods, the composition comprising nanoparticles comprising paclitaxel and albumin is administered without any steroid premedication and/or without G-CSF prophylaxis.

In some embodiments of any of the methods, the methods further include administration of an effective amount of an anti-angiogenic agent (e.g., angiogenesis inhibitor). In some embodiments, the anti-angiogenic agent is bevacizumab, sunitinib, or sorafenib tosylate. In some embodiments, the anti-angiogenic agent is bevacizumab. In some embodiments, the effective amount of bevacizumab is between about 5 mg/kg and about 15 mg/kg. In some embodiments, the effective amount of bevacizumab is about any of 5 mg/kg, 7.5 mg/kg, 10 mg/kg, or 15 mg/kg.

Prostate Cancer

The present invention provides methods of treating prostate cancer in an individual (e.g., human) comprising administering to the individual a) an effective amount of a composition comprising nanoparticles comprising docetaxel and an albumin; and b) an effective amount of a steroid (e.g., prednisone). The present invention provides methods of treating prostate cancer in an individual (e.g., human) comprising administering to the individual a) an effective amount of a composition comprising nanoparticles comprising docetaxel and an albumin; and b) an effective amount of a steroid (e.g., prednisone). In some embodiments, there is provided a method of treating prostate cancer in an individual (e.g., human) comprising administering to the individual a) an effective amount of a composition comprising nanoparticles comprising docetaxel coated with an albumin; and b) an effective amount of a steroid (e.g., prednisone). In some embodiments, there is provided a method of treating prostate cancer in an individual (e.g., human) comprising administering to the individual a) an effective amount of a composition comprising nanoparticles comprising docetaxel and an albumin, wherein the average size of the nanoparticles in the nanoparticle composition is no greater than about 200 nm; and b) an effective amount of a steroid (e.g., prednisone). In some embodiments, there is provided a method of treating prostate cancer in an individual (e.g., human) comprising administering to the individual a) an effective amount of a composition comprising nanoparticles comprising docetaxel coated with albumin, wherein the average size of the nanoparticles in the nanoparticle composition is no greater than about 200 nm; and b) an effective amount of a steroid (e.g., prednisone). In some embodiments, there is provided a method of treating prostate cancer in an individual (e.g., human) comprising administering to the individual a) an effective amount of Nab-docetaxel, wherein the average size of the nanoparticles in the nanoparticle composition is no greater than about 200 nm; and b) an effective amount of a steroid (e.g., prednisone).

Also provided are methods of treating prostate cancer in an individual comprising administering to the individual a) an effective amount of a composition comprising nanoparticles comprising docetaxel and an albumin and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of a composition comprising nanoparticles comprising docetaxel coated with albumin and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of a composition comprising nanoparticles comprising docetaxel and an albumin, wherein the average size of the nanoparticles in the nanoparticle composition is no greater than about 200 nm, and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of a composition comprising nanoparticles comprising docetaxel coated with albumin, wherein the average size of the nanoparticles in the nanoparticle composition is no greater than about 200 nm, and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake. In some embodiments, there is provided a method of treating prostate cancer in an individual comprising administering to the individual a) an effective amount of Nab-docetaxel, and b) an effective amount of a steroid (e.g., prednisone), wherein treatment is based upon the prostate cancer having one or more characteristics selected from the group consisting of (i) adenocarcinoma, (ii) differential levels of caveolin-1 (CAV1), (iii) differential levels of SPARC, (iv) differential levels of gp60, and (v) differential albumin uptake.

Provided herein are also methods of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel and an albumin and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel coated with an albumin and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel and an albumin, wherein the average size of the nanoparticles in the nanoparticle composition is no greater than about 200 nm, and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of a composition comprising nanoparticles comprising docetaxel coated with albumin, wherein the average size of the nanoparticles in the nanoparticle composition is no greater than about 200 nm, and ii) an effective amount of a steroid. In some embodiments, there is provided a method of treating prostate cancer, comprising: (a) selecting an individual having prostate cancer, wherein the prostate cancer has one or more characteristics selected from the group consisting of (i) adenocarcinoma, (ii) differential levels of caveolin-1 (CAV1), (iii) differential levels of SPARC, (iv) differential levels of gp60, and (v) differential albumin uptake; and (b) administering to the individual thus selected i) an effective amount of Nab-docetaxel, and ii) an effective amount of a steroid.

In some embodiments of any of the methods, the one or more characteristics of prostate cancer include 1, 2, 3, 4, or 5 characteristics of prostate cancer. In some embodiments, the one or more characteristics include, for example, at least two or more characteristics, at least three or more characteristics, or at least four or more characteristics. For example, in some embodiments, the prostate cancer is characterized by differential levels of CAV-1. In some embodiments, the prostate cancer is characterized by differential levels of CAV-1 and gp60. In some embodiments, the prostate cancer is characterized by differential levels of caveolin-1 (CAV1), differential levels of SPARC, differential levels of gp60, and differential albumin uptake.

In some embodiments of any of the methods, the prostate cancer is an adenocarcinoma. In some embodiments, the prostate cancer is a sarcoma, neuroendocrine tumor, small cell cancer, ductal cancer, or a lymphoma. There are provided methods of treating prostate cancer at any of the four stages, A, B, C, or D, according to the Jewett staging system. In some embodiments, the prostate cancer is stage A prostate cancer (The cancer cannot be felt during a rectal exam.). In some embodiments, the prostate cancer is stage B prostate cancer (The tumor involves more tissue within the prostate, it can be felt during a rectal exam, or it is found with a biopsy that is done because of a high PSA level.). In some embodiments, the prostate cancer is stage C prostate cancer (The cancer has spread outside the prostate to nearby tissues.). In some embodiments, the prostate cancer is stage D prostate cancer.

In some embodiments of any of the methods, the prostate cancer may be androgen independent prostate cancer (AIPC). In some embodiments, the prostate cancer may be androgen dependent prostate cancer. In some embodiments, the prostate cancer may be refractory to hormone therapy. In some embodiments, the prostate cancer may be substantially refractory to hormone therapy. In some embodiments, the individual may be a human who has a gene, genetic mutation, or polymorphism associated with prostate cancer (e.g., RNASEL/HPC1, ELAC2/HPC2, SR-A/MSR1, CHEK2, BRCA2, PON1, OGG1, MIC-1, TLR4, and/or PTEN) or has one or more extra copies of a gene associated with prostate cancer.

In some embodiments of any of the methods described herein, the prostate cancer is early stage prostate cancer, non-metastatic prostate cancer, primary prostate cancer, advanced prostate cancer, locally advanced prostate cancer, metastatic prostate cancer, prostate cancer in remission, or recurrent prostate cancer. In some embodiments, the prostate cancer is localized resectable, localized unresectable, or unresectable.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first-line therapy. In some embodiments, the method is used as a second-line therapy.

In some embodiments of any of the methods described herein, the composition comprises nanoparticles comprising docetaxel and an albumin (such as human serum albumin), wherein docetaxel in the nanoparticles is coated with the albumin. In some embodiments, the average particle size of the nanoparticles in the composition is no greater than about 200 nm (such as less than about 200 nm). In some embodiments, the composition comprises Nab-docetaxel. In some embodiments, the composition is the Nab-docetaxel. In some embodiments, the docetaxel nanoparticle composition and the steroid have synergistic effect on treating prostate cancer. In some embodiments, the steroid is prednisone.

In some embodiments of any of the methods described herein, the effective amount of a composition comprising nanoparticles comprising docetaxel and the albumin is between about 30 mg/m$^2$ to about 200 mg/m$^2$ (e.g., 60 mg/m$^2$, 75 mg/m$^2$, or 100 mg/m$^2$) and the effective amount of the steroid is between about 2.5 mg to about 20 mg (e.g., 2.5 mg, 5 mg, or 10 mg). In some embodiments of any of the methods described herein, the effective amount of the composition comprising nanoparticles comprising docetaxel and the albumin is administered once every three weeks and the effective amount of the steroid is administered twice daily. In some embodiments, the effective amount of the composition comprising nanoparticles comprising docetaxel and the albumin is between about 30 to about 200 mg/m$^2$ administered once every three weeks and the effective amount of the steroid is between about 2.5 mg to about 20 mg administered twice daily. In some embodiments, the effective amount of the composition comprising nanoparticles comprising docetaxel and the albumin is about 75 mg/m$^2$ administered once every three weeks and the effective amount of a steroid is about 5 mg administered twice daily. In some embodiments, the docetaxel nanoparticle composition is administered intravenously. In some embodiments, the steroid is administered orally. In some embodiments, the composition comprising nanoparticles comprising docetaxel and the albumin and the steroid are sequentially administered; concurrently administered or simultaneously administered.

Thus, for example, in some embodiments, there is provided a method of treating prostate cancer in an individual, comprising administering to the individual: a) between about 30 mg/m$^2$ to about 200 mg/m$^2$ (e.g., 60 mg/m$^2$, 75 mg/m$^2$, or 100 mg/m$^2$) nanoparticles comprising docetaxel and an albumin (such as nanoparticles comprising docetaxel coated with albumin, for example Nab-docetaxel) and b) between about 2.5 mg to about 20 mg (e.g., 2.5 mg, 5 mg, or 10 mg) of a steroid (such as prednisone). In some embodiments, there is provided a method of treating prostate cancer in an individual, comprising administering to the individual: a) between about 30 mg/m$^2$ to about 200 mg/m$^2$ (e.g., 60 mg/m$^2$, 75 mg/m$^2$, or 100 mg/m$^2$) nanoparticles comprising docetaxel and an albumin (such as nanoparticles comprising docetaxel coated with albumin, for example Nab-docetaxel) once every three weeks, and b) between about 2.5 mg to about 20 mg (e.g., 2.5 mg, 5 mg, or 10 mg) of a steroid (such as prednisone) twice daily. In some embodiments, there is provided a method of treating prostate cancer in an individual, comprising administering to the individual: a) between about 30 mg/m$^2$ to about 200 mg/m$^2$ (e.g., 60 mg/m$^2$, 75 mg/m$^2$, or 100 mg/m$^2$) nanoparticles comprising docetaxel and an albumin (such as nanoparticles comprising docetaxel coated with albumin, for example Nab-docetaxel) once every three weeks intravenously, and b) between about 2.5 mg to about 20 mg (e.g., 2.5 mg, 5 mg, or 10 mg) of a steroid (such as prednisone) twice daily orally.

In some embodiments of any of the methods described herein, an individual (e.g., human) who has been diagnosed with or is suspected of having prostate cancer can be treated. In some embodiments, the individual is human. In some embodiments, the individual is at least about any of 35, 40, 45, 50, 55, 60, 65, 70, 75, 80, or 85 years old. In some embodiments, the individual is male. In some embodiments, the individual has any of the types of prostate cancer described herein. In some embodiments, the individual has a single lesion at presentation. In some embodiments, the individual has multiple lesions at presentation. In some embodiments, the individual is resistant to treatment of prostate cancer with other agents (such as a non-nanoparticle formulation of taxane, e.g., Taxol® or Taxotere®). In some embodiments, the individual is initially responsive to treatment of prostate cancer with other agents (such as a non-nanoparticle formulation of taxane, e.g., Taxol® or Taxotere®) but has progressed after treatment.

In some embodiments, a lower amount of each pharmaceutically active compound is used as part of a combination therapy compared to the amount generally used for individual therapy. In some embodiments, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. For example, the use of a small amount of pharmaceutically active compound may result in a reduction in the number, severity, frequency, or duration of one or more side-effects associated with the compound.

The methods described herein can be used for any one or more of the following purposes: alleviating one or more symptoms of prostate cancer, delaying progressing of prostate cancer, shrinking tumor size in prostate cancer patient, inhibiting prostate cancer tumor growth, prolonging overall survival, prolonging progression free survival, preventing or delaying prostate cancer tumor metastasis, reducing (such as eradiating) preexisting prostate cancer tumor metastasis, reducing incidence or burden of preexisting prostate cancer tumor metastasis, or preventing recurrence of prostate cancer.

Dosing and Method of Administering the Nanoparticle Compositions

Although this section focuses on methods of treating NSCLC using nanoparticle compositions comprising paclitaxel, it is to be understood that the description also applies to treatment of other cancers described herein, for example treatment of prostate cancer using nanoparticles comprising docetaxel.

The dose of the paclitaxel nanoparticle compositions administered to an individual (such as a human) may vary with the particular composition, the mode of administration, and the type of NSCLC being treated. In some embodiments, the amount of the paclitaxel nanoparticle composition and/or the amount of the platinum-based agent (e.g. carboplatin) is effective to result in an objective response (such as a partial response or a complete response). In some embodiments, the amount of the paclitaxel nanoparticle composition and/or the amount of the platinum-based agent (e.g. carboplatin) is sufficient to result in a complete response in the individual. In some embodiments, the amount of the paclitaxel nanoparticle composition and/or the amount of the platinum-based agent (e.g. carboplatin) is sufficient to result in a partial response in the individual. In some embodiments, the amount of the paclitaxel nanoparticle composition and the amount of the platinum-based agent (e.g. carboplatin) is sufficient to result in a higher objective response (such as a complete response or a partial response) in the individual compared to a paclitaxel nanoparticle composition alone, Taxol® alone, a platinum-based agent (e.g. carboplatin) alone, and/or the combination of Taxol® and platinum-based agent (e.g. carboplatin). Responses of an individual to the treatment of the methods described herein can be determined, for example, based on RECIST levels.

In some embodiments, the amount of the paclitaxel nanoparticle composition and/or the amount of the platinum-based agent (e.g. carboplatin) is sufficient to increase progression-free survival of the individual. In some embodiments, the amount of the paclitaxel nanoparticle composition and/or the amount of the platinum-based agent (e.g., carboplatin) is sufficient to prolong overall survival of the individual. In some embodiments, the amount of the paclitaxel nanoparticle composition and the amount of the platinum-based agent (e.g. carboplatin) is sufficient to increase progression-free survival of the individual compared to a paclitaxel nanoparticle composition alone, Taxol® alone, a platinum-based agent (e.g. carboplatin) alone, and/or the combination of Taxol® and platinum-based agent (e.g. carboplatin).

In some embodiments, the amount of the paclitaxel nanoparticle composition and/or the amount of the platinum-based agent (e.g., carboplatin) is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of NSCLC cells, or tumor growth rate in the same subject at the time of starting treatment or compared to the corresponding activity in other subjects not receiving the treatment. In some embodiments, the amount of the paclitaxel nanoparticle composition and the amount of the platinum-based agent (e.g. carboplatin) is sufficient to decrease the size of a tumor, decrease the number of cancer cells, or decrease the growth rate of a tumor at the time of starting treatment by more than at least about any of 10%, 20%, 30%, 40%, 50%, 60%, 70%, 80%, 90%, 95% or 100% compared to a paclitaxel nanoparticle composition alone, Taxol® alone, a platinum-based agent (e.g. carboplatin) alone, and/or the combination of Taxol® and platinum-based agent (e.g. carboplatin). Standard methods can be used to measure the magnitude of this effect.

In some embodiments, the amount of the paclitaxel in the nanoparticle composition is below the level that induces a toxicological effect (i.e., an effect above a clinically acceptable level of toxicity) or is at a level where a potential side effect can be controlled or tolerated when the nanoparticle composition is administered to the individual.

In some embodiments, the amount of the paclitaxel nanoparticle composition and/or the amount of the platinum-based agent (e.g. carboplatin) is close to a maximum tolerated dose (MTD) of the composition following the same dosing regime. In some embodiments, the amount of the composition is more than about any of 80%, 90%, 95%, or 98% of the MTD.

In some embodiments, the amount of paclitaxel in the nanoparticle composition is included in any of the following ranges: about 0.1 mg to about 500 mg, about 0.1 mg to about 2.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of paclitaxel in the effective amount of the nanoparticle composition (e.g., a unit dosage form) is in the range of about 5 mg to about 500 mg, such as about 30 mg to about 300 mg or about 50 mg to about 200 mg. In some embodiments, the concentration of paclitaxel in the nanoparticle composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of paclitaxel is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of paclitaxel in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m2, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m2, 1000 mg/m$^2$, or 1080 mg/m$^2$ of paclitaxel. In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of paclitaxel. In some embodiments, the amount of paclitaxel per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of paclitaxel in the nanoparticle composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of paclitaxel in the nanoparticle composition is about 5 to about 300 mg/m$^2$, such as about 20 to about 60 mg/m$^2$, about 100 to about 150 mg/m$^2$, about 120 mg/m$^2$, about 130 mg/m$^2$, or about 140 mg/m$^2$.

In some embodiments of any of the above aspects, the effective amount of paclitaxel in the nanoparticle composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of paclitaxel in the nanoparticle composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of paclitaxel.

Exemplary dosing frequencies for the administration of the paclitaxel nanoparticle compositions include, but are not limited to, daily, every two days, every three days, every four days, every five days, every six days, weekly without break, three out of four weeks, once every three weeks, once every two weeks, or two out of three weeks. In some embodiments, the paclitaxel nanoparticle composition is administered about once every 2 weeks, once every 3 weeks, once every 4 weeks, once every 6 weeks, or once every 8 weeks. In some embodiments, the paclitaxel nanoparticle composition is administered at least about any of 1x, 2x, 3x, 4x, 5x, 6x, or 7x (i.e., daily) a week. In some embodiments, the paclitaxel nanoparticle composition is administered weekly. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, paclitaxel in the nanoparticle composition is administered over a period of at least ten days, wherein the interval between each administration is no more than about two days, and wherein the dose of paclitaxel at each administration is about 0.25 mg/m$^2$ to about 250 mg/m$^2$, about 0.25 mg/m$^2$ to about 150 mg/m$^2$, about 0.25 mg/m$^2$ to about 75 mg/m$^2$, such as about 0.25 mg/m$^2$ to about 25 mg/m$^2$, about 20 mg/m$^2$ to about 60 mg/m$^2$, or about 25 mg/m$^2$ to about 50 mg/m$^2$.

The administration of the paclitaxel nanoparticle composition can be extended over an extended period of time, such as from about a month up to about seven years. In some embodiments, the paclitaxel nanoparticle composition is administered over a period of at least about any of 2, 3, 4, 5, 6, 7, 8, 9, 10, 11, 12, 18, 24, 30, 36, 48, 60, 72, or 84 months.

In some embodiments, the dosage of paclitaxel in a nanoparticle composition can be in the range of 5-400 mg/m$^2$ when given on a 3 week schedule, or 5-250 mg/m$^2$ (such as 40-100 mg/m$^2$, 50-125 mg/m$^2$, for example 50-100 mg/m$^2$) when given on a weekly schedule. For example, the amount of paclitaxel is about 50 to about 125 mg/m$^2$ (e.g., about 100 mg/m$^2$) on a weekly schedule, e.g., weekly without a break.

Other exemplary dosing schedules for the administration of paclitaxel in the nanoparticle composition include, but are not limited to, 100 mg/m$^2$, weekly, without break; 75 mg/m$^2$, weekly, without break; 50 mg/m$^2$, weekly, without break; 100 mg/m$^2$ weekly, 3 out of 4 weeks; 75 mg/m$^2$ weekly, 3 out of four weeks; or 50 mg/m$^2$ weekly, 3 out of 4 weeks. The dosing frequency of the composition may be adjusted over the course of the treatment based on the judgment of the administering physician.

In some embodiments of any of the above aspects, the cumulative dose of paclitaxel in the nanoparticulate composition administered includes at least about any of 1000 mg/m$^2$, 1100 mg/m$^2$, 1200 mg/m$^2$, 1300 mg/m$^2$, 1400 mg/m$^2$, 1450 mg/m$^2$, 1500 mg/m$^2$, 1600 mg/m$^2$, or 1700 mg/m$^2$. In some embodiments, the cumulative dose of paclitaxel in the nanoparticulate composition is between about any of 1000 mg/m$^2$ to 1700 mg/m$^2$, 1100 mg/m$^2$ to 1600 mg/m$^2$, 1200 mg/m$^2$ to 1600 mg/m$^2$, 1300 mg/m$^2$ to 1600 mg/m$^2$, or 1400 mg/m$^2$ to 1500 mg/m$^2$.

In some embodiments, the individual is treated for at least about any of one, two, three, four, five, six, seven, eight, nine, or ten treatment cycles.

The paclitaxel nanoparticle compositions described herein allow infusion of the paclitaxel nanoparticle composition to an individual over an infusion time that is shorter than about 24 hours. For example, in some embodiments, the paclitaxel nanoparticle composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

In some embodiments, the amount of the platinum-based agent (e.g. carboplatin) is between about any of AUC=1 to AUC=10, AUC=2 to AUC=8, or AUC=3 to AUC=6. In some embodiments, the amount of the platinum-based agent (e.g. carboplatin) is about any of AUC=2, AUC=2.5, AUC=3, AUC=3.5, AUC=4, AUC=4.5, AUC=5, AUC=5.5, AUC=6, AUC=6.5, or AUC=7. Exemplary dosing frequencies for the administration of the platinum-based agent (e.g. carboplatin) include, but are not limited to, daily, every two days, every three days, every four days, every five days, every six days, weekly without break, three out of four weeks, once every three weeks, once every two weeks, or two out of three weeks. In some embodiments, the platinum-based agent (e.g. carboplatin) is administered about once every 2 weeks, once every 3 weeks, once every 4 weeks, once every 6 weeks, or once every 8 weeks. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosage of the platinum-based agent (e.g. carboplatin) can be between about AUC=2 to about AUC=6 (such as about any of AUC=2, AUC=3, AUC=4.5, or AUC=6) when given on a 3 week schedule, or AUC=2 to about AUC=6 (such as about any of AUC=2, AUC=3, AUC=4.5, or AUC=6) when given on a three out of four week schedule. For example, the amount of paclitaxel is about 50 to about 125 mg/m$^2$ (e.g., about 100 mg/m$^2$) on a weekly schedule, e.g., weekly without a break. In some embodiments, the dosage of the platinum-based agent (e.g. carboplatin) can be between about AUC=2 to about AUC=6 (such as about any of AUC=2, AUC=3, AUC=4.5, or AUC=6) on a weekly schedule.

The nanoparticle composition and the platinum-based agent (e.g. carboplatin) can be administered using the same route of administration or different routes of administration. The paclitaxel nanoparticle compositions and/or the platinum-based agent (e.g. carboplatin) can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the paclitaxel nanoparticle composition and/or the platinum-based agent may be used. In some embodiments, the paclitaxel nanoparticle composition and/or the platinum-based agent (e.g. carboplatin) is administered intravenously. In some embodiments, the paclitaxel nanoparticle composition and the platinum-based agent (e.g. carboplatin) are administered intravenously. In some embodiments, the paclitaxel nanoparticle composition and/or the platinum-based agent (e.g. carboplatin) is administered intraportally. In some embodiments, the paclitaxel nanoparticle composition and/or the platinum-based agent (e.g. carboplatin) is administered intraarterially. In some embodiments, the paclitaxel nanoparticle composition and/or the platinum-based agent (e.g. carboplatin) is administered intraperitoneally. In some embodiments, the paclitaxel nanoparticle composition and/or the platinum-based agent (e.g. carboplatin) is administered by inhalation.

In some embodiments, the paclitaxel nanoparticle composition and the platinum-based agent (e.g. carboplatin) are administered simultaneously. When the drugs are administered simultaneously, the paclitaxel in the nanoparticles and the platinum-based agent contained in the same composition (e.g., a composition comprising both the nanoparticles and the platinum-based agent) or in separate compositions (e.g., the nanoparticles are contained in one composition and the platinum-based agent (e.g. carboplatin) is contained in another composition).

In some embodiments, the paclitaxel nanoparticle composition and the platinum-based agent (e.g. carboplatin) are administered sequentially. Either the paclitaxel nanoparticle composition or the platinum-based agent (e.g. carboplatin) may be administered first. The paclitaxel nanoparticle composition and the platinum-based agent (e.g. carboplatin) are contained in separate compositions, which may be contained in the same or different packages.

In some embodiments, the administration of the paclitaxel nanoparticle composition and the platinum-based agent (e.g. carboplatin) are concurrent, i.e., the administration period of the nanoparticle composition and that of the platinum-based agent (e.g. carboplatin) overlap with each other. In some embodiments, the paclitaxel nanoparticle composition is administered for at least one cycle (for example, at least any of 2, 3, or 4 cycles) prior to the administration of the platinum-based agent. In some embodiments, the platinum-based agent (e.g. carboplatin) is administered for at least any of one, two, three, or four weeks. In some embodiments, the administrations of the paclitaxel nanoparticle composition and the platinum-based agent (e.g. carboplatin) are initiated at about the same time (for example, within any one of 1, 2, 3, 4, 5, 6, or 7 days). In some embodiments, the administrations of the paclitaxel nanoparticle composition and the platinum-based agent (e.g. carboplatin) are terminated at about the same time (for example, within any one of 1, 2, 3, 4, 5, 6, or 7 days). In some embodiments, the administration of the platinum-based agent (e.g. carboplatin) continues (for example for about any one of 1, 2, 3, 4, 5, 6, 7, 8, 9, 10, 11, or 12 months) after the termination of the administration of the paclitaxel nanoparticle composition. In some embodiments, the administration of the platinum-based agent (e.g. carboplatin) is initiated after (for example after about any one of 1, 2, 3, 4, 5, 6, 7, 8, 9, 10, 11, or 12 months) the initiation of the administration of the paclitaxel nanoparticle composition. In some embodiments, the administrations of the paclitaxel nanoparticle composition and the platinum-based agent (e.g. carboplatin) are initiated and terminated at about the same time. In some embodiments, the administrations of the paclitaxel nanoparticle composition and the platinum-based agent (e.g. carboplatin) are initiated at about the same time and the administration of the platinum-based agent (e.g. carboplatin) continues (for example for about any one of 1, 2, 3, 4, 5, 6, 7, 8, 9, 10, 11, or 12 months) after the termination of the administration of the paclitaxel nanoparticle composition. In some embodiments, the administration of the paclitaxel nanoparticle composition and the platinum-based agent (e.g. carboplatin) stop at about the same time and the administration of the platinum-based agent (e.g. carboplatin) is initiated after (for example after about any one of 1, 2, 3, 4, 5, 6, 7, 8, 9, 10, 11, or 12 months) the initiation of the administration of the paclitaxel nanoparticle composition.

In some embodiments, the administration of the paclitaxel nanoparticle composition and the platinum-based agent (e.g. carboplatin) are non-concurrent. For example, in some embodiments, the administration of the paclitaxel nanoparticle composition is terminated before the platinum-based agent (e.g. carboplatin) is administered. In some embodiments, the administration of the platinum-based agent (e.g. carboplatin) is terminated before the paclitaxel nanoparticle composition is administered. The time period between these two non-concurrent administrations can range from about two to eight weeks, such as about four weeks.

The dosing frequency of the platinum-based agent (e.g. carboplatin) can be the same or different from that of the paclitaxel nanoparticle composition. The dosing frequency of the paclitaxel-containing nanoparticle composition and the platinum-based agent (e.g. carboplatin) may be adjusted over the course of the treatment, based on the judgment of the administering physician. When administered separately, the paclitaxel nanoparticle composition and the platinum-based agent (e.g. carboplatin) can be administered at different dosing frequency or intervals. For example, the paclitaxel nanoparticle composition can be administered weekly, while the platinum-based agent (e.g. carboplatin) can be administered more or less frequently. In some embodiments, sustained continuous release formulation of the drug-containing nanoparticle and/or the platinum-based agent may be used. Various formulations and devices for achieving sustained release are known in the art. A combination of the administration configurations described herein can also be used.

In some embodiments, the dosage of paclitaxel in nanoparticle composition is between about 50 to about 125 mg/m$^2$ and the dosage of platinum-based agent (e.g. carboplatin) is between about AUC=2 to about AUC=6. In some embodiments, the dosage of paclitaxel in nanoparticle composition is between about 50 to about 125 mg/m$^2$ weekly and the dosage of platinum-based agent (e.g. carboplatin) is between about AUC=2 to about AUC=6 once every three weeks. In some embodiments, the dosage of paclitaxel in nanoparticle composition is about 100 mg/m$^2$ weekly and the dosage of platinum-based agent (e.g. carboplatin) is about AUC=6 once every three weeks. In some embodiments, the dosage of paclitaxel in nanoparticle composition is about 75 mg/m$^2$ weekly and the dosage of platinum-based agent (e.g. carboplatin) is about AUC=4.5 once every three weeks. In some embodiments, the dosage of paclitaxel in nanoparticle composition is about 50 mg/m$^2$ weekly and the dosage of platinum-based agent (e.g. carboplatin) is about AUC=3 once every three weeks. In some embodiments, the paclitaxel nanoparticle composition and/or the platinum-based agent (e.g. carboplatin) is administered intravenously. In some embodiments, the paclitaxel nanoparticle composition and the platinum-based agent (e.g. carboplatin) are administered intravenously. In some embodiments, the platinum-based agent is carboplatin.

The doses required for paclitaxel and/or the platinum-based agent (e.g. carboplatin) may (but not necessarily) be lower than what is normally required when each agent is administered alone. Thus, in some embodiments, a subtherapeutic amount of the drug in the nanoparticle composition and/or the platinum-based agent is administered. "Subtherapeutic amount" or "subtherapeutic level" refer to an amount that is less than the therapeutic amount, that is, less than the amount normally used when the drug in the nanoparticle composition and/or the platinum-based agent (e.g. carboplatin) are administered alone. The reduction may be reflected in terms of the amount administered at a given administration and/or the amount administered over a given period of time (reduced frequency).

In some embodiments, enough the platinum-based agent (e.g. carboplatin) is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough paclitaxel in the nanoparticle composition is administered so as to allow reduction of the normal dose of the platinum-based agent (e.g. carboplatin) required to affect the same degree of treatment by at least about any of 5%, 10%, 20%, 30%, 50%, 60%, 70%, 80%, 90%, or more.

In some embodiments, the dose of both paclitaxel in the nanoparticle composition and the platinum-based agent are reduced as compared to the corresponding normal dose of each when administered alone. In some embodiments, both paclitaxel in the nanoparticle composition and the platinum-based agent are administered at a subtherapeutic, i.e., reduced, level. In some embodiments, the dose of the nanoparticle composition and/or the platinum-based agent is substantially less than the established maximum toxic dose (MTD). For example, the dose of the nanoparticle composition and/or the platinum-based agent is less than about 50%, 40%, 30%, 20%, or 10% of the MTD.

In some embodiments of any of the methods, the methods further include administration of an effective amount of an anti-angiogenic agent. In some embodiments, the anti-angiogenic agent is bevacizumab, sunitinib, or sorafenib tosylate. In some embodiments, the anti-angiogenic agent is bevacizumab. In some embodiments, the effective amount of bevacizumab is between about 5 mg/kg and about 15 mg/kg. In some embodiments, the effective amount of bevacizumab is about any of 5 mg/kg, 7.5 mg/kg, 10 mg/kg, or 15 mg/kg.

A combination of the administration configurations described herein can be used. The combination therapy methods described herein may be performed alone or in conjunction with another therapy, such as chemotherapy, radiation therapy, surgery, hormone therapy, gene therapy, immunotherapy, chemoimmunotherapy, hepatic artery-based therapy, cryotherapy, ultrasound therapy, local ablative therapy, radiofrequency ablation therapy, photodynamic therapy, and the like. Additionally, a person having a greater risk of developing the NSCLC may receive treatments to inhibit or and/or delay the development of the disease.

In some embodiments, the administration of the paclitaxel nanoparticle composition and the platinum-based agent (e.g. carboplatin) are concurrent with radiation therapy (e.g. thoracic radiation). In some embodiments, the administration of the paclitaxel nanoparticle composition is administered concurrent with radiation therapy (e.g. thoracic radiation). Radiation contemplated herein includes, for example, γ-rays, X-rays (external beam), and the directed delivery of radioisotopes to tumor cells. Other forms of DNA damaging factors are also contemplated such as microwaves and UV irradiation are also contemplated. Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted. In some embodiments, the radiation may be performed in 25-40 (e.g., about 33) fractions by either 3D conformal or intensity-modulated techniques. In some embodiments, the dosage of paclitaxel nanoparticle composition is between about 20 mg/m² to about 60 mg/m² (e.g., 40 mg/m²) weekly, the dosage of platinum-based agent (e.g. carboplatin) is between about AUC=2 to AUC=6 (e.g., AUC=2) weekly, and the dosage of thoracic radiation is between about 25 to about 40 (e.g., about 33) fractions by either 3D conformal or intensity-modulated techniques concurrently.

When the radiation comprises use of radioactive isotopes, the isotope may be conjugated to a targeting agent, such as a therapeutic antibody, which carries the radionucleotide to the target tissue. Suitable radioactive isotopes include, but are not limited to, astatine$^{211}$, $^{14}$carbon, $^{51}$chromium, $^{36}$chlorine, $^{57}$iron, $^{58}$cobalt, copper$^{67}$, $^{152}$Eu, gallium$^{67}$, $^{3}$hydrogen, iodine$^{123}$, iodine$^{131}$, indium$^{111}$, $^{59}$ion, $^{32}$phosphorus, rhenium$^{186}$, $^{75}$selenium, $^{35}$sulphur, technicium$^{99m}$, and/or yttrium$^{90}$.

Nanoparticle Compositions

The nanoparticle compositions described herein comprise nanoparticles comprising (in various embodiments consisting essentially of) paclitaxel (or docetaxel) and an albumin (such as human serum albumin) Nanoparticles of poorly water soluble drugs (such as paclitaxel) have been disclosed in, for example, U.S. Pat. Nos. 5,916,596; 6,506,405; 6,749,868, 6,537,579; and U.S. Pat. No. 7,820,788 and also in U.S. Pat. Pub. Nos. 2006/0263434, and 2007/0082838; PCT Patent Application WO08/137,148, each of which is incorporated by reference in their entirety. Although the description below focuses on nanoparticle compositions comprising paclitaxel, the same also applies to nanoparticle compositions comprising docetaxel.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the albumin has sulfhydral groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprise paclitaxel coated with an albumin (e.g., human serum albumin). In some embodiments, the composition comprises paclitaxel in both nanoparticle and non-nanoparticle forms, wherein at least about any one of 50%, 60%, 70%, 80%, 90%, 95%, or 99% of paclitaxel in the composition are in nanoparticle form. In some embodiments, paclitaxel in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of paclitaxel that is substantially free of polymeric materials (such as polymeric matrix).

In some embodiments, the composition comprises albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of albumin (such as human serum albumin) and paclitaxel in the nanoparticle composition is about 18:1 or less, such as about 15:1 or less, for example about 10:1 or less. In some embodiments, the weight ratio of albumin (such as human serum albumin) and paclitaxel in the composition falls within the range of any one of about 1:1 to about 18:1, about 2:1 to about 15:1, about 3:1 to about 13:1, about 4:1 to about 12:1, or about 5:1 to about 10:1. In some embodiments, the weight ratio of albumin and paclitaxel in the nanoparticle portion of the composition is about any one of 1:2, 1:3, 1:4, 1:5, 1:6, 1:7, 1:8, 1:9, 1:10, 1:11, 1:12, 1:13, 1:14, 1:15, or less. In some embodiments, the weight ratio of the albumin (such as human serum albumin) and paclitaxel in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises human serum albumin. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics*, $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Paclitaxel has been shown to bind HSA (see, e.g., Paal et al., *Eur. J. Biochem.*, 268(7), 2187-91 (200a)).

The albumin (such as human serum albumin) in the composition generally serves as a carrier for paclitaxel, i.e., the albumin in the composition makes paclitaxel more readily suspendable in an aqueous medium or helps maintain the suspension as compared to compositions not comprising an albumin. This can avoid the use of toxic solvents (or surfactants) for solubilizing paclitaxel, and thereby can reduce one or more side effects of administration of paclitaxel into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant.

The amount of albumin in the composition described herein will vary depending on other components in the composition. In some embodiments, the composition comprises an albumin in an amount that is sufficient to stabilize paclitaxel in an aqueous suspension, for example, in the form of a stable colloidal suspension (such as a stable suspension of nanoparticles). In some embodiments, the albumin is in an amount that reduces the sedimentation rate of paclitaxel in an aqueous medium. For particle-containing compositions, the amount of the albumin also depends on the size and density of nanoparticles of paclitaxel.

Paclitaxel is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize paclitaxel in an aqueous suspension at a certain concentration. For example, the concentration of paclitaxel in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of paclitaxel is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of albumin. In some embodiments, the composition, in liquid form, comprises about 0.5% to about 5% (w/v) of albumin.

In some embodiments, the weight ratio of albumin, e.g., albumin, to paclitaxel in the nanoparticle composition is such that a sufficient amount of paclitaxel binds to, or is transported by, the cell. While the weight ratio of albumin to paclitaxel will have to be optimized for different albumin and paclitaxel combinations, generally the weight ratio of albumin, e.g., albumin, to paclitaxel (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to paclitaxel weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human serum albumin) and paclitaxel in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, or about 1:1 to about 1:1.

In some embodiments, the albumin allows the composition to be administered to an individual (such as human) without significant side effects. In some embodiments, the albumin (such as human serum albumin) is in an amount that is effective to reduce one or more side effects of administration of paclitaxel to a human. The term "reducing one or more side effects of administration of paclitaxel" refers to reduction, alleviation, elimination, or avoidance of one or more undesirable effects caused by paclitaxel, as well as side effects caused by delivery vehicles (such as solvents that render paclitaxel suitable for injection) used to deliver paclitaxel. In some embodiments, the one or more side effects are adverse side effects (AEs). In some embodiments, the one or more side effects are serious adverse side effects (SAEs). Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with paclitaxel can be reduced.

In some embodiments, the nanoparticle composition comprises Abraxane® (Nab-paclitaxel). In some embodiments, the nanoparticle composition is Abraxane® (Nab-paclitaxel). Abraxane® is a formulation of paclitaxel stabilized by human albumin USP, which can be dispersed in directly injectable physiological solution. When dispersed in a suitable aqueous medium such as 0.9% sodium chloride injection or 5% dextrose injection, Abraxane® forms a stable colloidal suspension of paclitaxel. The mean particle size of the nanoparticles in the colloidal suspension is about 130 nanometers. Since HSA is freely soluble in water, Abraxane® can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Methods of making nanoparticle compositions are known in the art. For example, nanoparticles containing paclitaxel and albumin (such as human serum albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579, and U.S. Pat. No. 7,820,788 and also in U.S. Pat. Pub. No. 2007/0082838, 2006/0263434 and PCT Application WO08/137,148.

Briefly, paclitaxel is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Other Components in the Nanoparticle Compositions

The nanoparticles described herein can be present in a composition that includes other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. No. 5,916,596 and U.S. Pat. No. 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits, Medicines, and Compositions

The invention also provides kits, medicines, compositions, and unit dosage forms for use in any of the methods described herein.

Kits of the invention include one or more containers comprising paclitaxel-containing nanoparticle compositions (or unit dosage forms and/or articles of manufacture) and/or the platinum-based agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising nanoparticles comprising paclitaxel and an albumin (such as human serum albumin), b) an effective amount of the platinum-based agent, and c) instructions for administering the nanoparticle composition and the platinum-based agents for treatment of NSCLC. The nanoparticles and the platinum-based agent can be present in separate containers or in a single container. For example, the kit may comprise one distinct composition or two or more compositions wherein one composition comprises nanoparticles and one composition comprises the platinum-based agent.

The kits of the invention are in suitable packaging. Suitable packaging include, but is not limited to, vials, bottles, jars, flexible packaging (e.g., Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the paclitaxel nanoparticle compositions and platinum-based agent (e.g. carboplatin) generally include information as to dosage, dosing schedule, and route of administration for the intended treatment. In some embodiments, the instructions indicate that a dosage between about 50 to about 125 mg/m$^2$ of paclitaxel nanoparticle composition and the dosage between about AUC=2 to about AUC=6 of platinum-based agent (e.g. carboplatin) should be administered. In some embodiments, the instructions indicate a dosage between about 50 to about 125 mg/m$^2$ of paclitaxel nanoparticle composition weekly administered and a dosage between about AUC=2 to about AUC=6 of platinum-based agent (e.g. carboplatin) administered once every three weeks should be used for the intended treatment. In some embodiments, the instructions indicate a dosage of about 100 mg/m$^2$ of paclitaxel nanoparticle composition weekly administered and a dosage of about AUC=6 of platinum-based agent (e.g. carboplatin) administered once every three weeks should be used for the intended treatment. In some embodiments, the instructions indicate a dosage of about 75 mg/m$^2$ of paclitaxel nanoparticle composition weekly administered and the dosage of AUC=4.5 of platinum-based agent (e.g. carboplatin) administered once every three weeks should be used for the intended treatment. In some embodiments, the instructions indicate a dosage of about 50 mg/m$^2$ of paclitaxel nanoparticle composition weekly and the dosage of about AUC=3 of platinum-based agent (e.g. carboplatin) administered once every three weeks should be used for the intended treatment. In some embodiments, the instructions indicate a dosage of between about 20 mg/m$^2$ to about 60 mg/m$^2$ (e.g., 40 mg/m$^2$) of paclitaxel nanoparticle composition administered weekly, a dosage between about AUC=2 to AUC=6 (e.g., AUC=2) of platinum-based agent (e.g. carboplatin) administered weekly, and a dosage of between about 25 to about 40 (e.g., about 33) fractions of thoracic radiation by either 3D conformal or intensity-modulated techniques concurrently. In some embodiments, the instructions indicate that paclitaxel nanoparticle composition and/or the platinum-based agent (e.g. carboplatin) is administered intravenously. In some embodiments, the instructions indicate that paclitaxel nanoparticle composition and the platinum-based agent (e.g. carboplatin) are administered intravenously. In some embodiments, the instructions indicate that the platinum-based agent is carboplatin.

In some embodiments, the kit provides a label denoting (i.e., indicating) that the paclitaxel nanoparticle composition and the platinum-based agent are indicated for treating individuals having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

The containers may be unit doses, bulk packages (e.g., multi-dose packages) or sub-unit doses. For example, kits may be provided that contain sufficient dosages of paclitaxel as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more.

Kits may also include multiple unit doses of paclitaxel and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition or a unit dosage form) for use in treating NSCLC in conjunction with the platinum-based agent, comprising nanoparticles comprising paclitaxel and an albumin (such as human serum albumin). In some embodiments, there is provided a medicine (or composition or a unit dosage form) for use in treating NSCLC, comprising nanoparticles comprising paclitaxel and an albumin (such as human serum albumin) and the platinum-based agent.

Exemplary Embodiments

1. A method of treating non-small-cell lung cancer (NSCLC) in an individual in need thereof, comprising administering to the individual a) an effective amount of a composition comprising nanoparticles comprising paclitaxel and an albumin and b) an effective amount of a platinum-based agent, wherein the NSCLC is squamous cellular carcinoma.

2. A method of treating NSCLC in an individual comprising administering to the individual a) an effective amount of a composition comprising nanoparticles comprising paclitaxel and an albumin and b) an effective amount of a platinum-based agent, wherein treatment is based upon the NSCLC having one or more characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

3. A method of treating NSCLC in an individual provided that the NSCLC has been found to have one or more characteristics selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake, the treatment comprising administering to the individual i) an effective amount of a composition comprising nanoparticles comprising paclitaxel and an albumin and ii) an effective amount of a platinum-based agent.

4. A method of treating NSCLC, comprising: (a) selecting an individual having NSCLC, wherein the NSCLC has one or more characteristics selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (b) administering to the individual thus selected i) an effective amount of a composition comprising nanoparticles comprising paclitaxel and an albumin and ii) an effective amount of a platinum-based agent.

5. A method of assessing whether an individual with NSCLC will respond to treatment comprising assessing one or more characteristics of the NSCLC selected from the group consisting of (a) squamous cellular carcinoma, (b) differential levels of caveolin-1 (CAV1), (c) differential levels of SPARC, (d) differential levels of hypoxia markers, (e) differential levels of tumor acidity, (f) differential levels of gp60, (g) differential levels of thymidylate synthase (TS), (h) differential levels of S phase kinase-associated protein (Skp2), (i) differential loss of heterozygosity (LOH) of single-nucleotide polymorphism (SNP), (j) differential Kras mutations, (k) differential methylation of promoter region of tumor-related genes, and (l) differential albumin uptake, wherein one or more of the characteristics of the NSCLC indicates the individual will be responsive to the treatment and the treatment comprises i) an effective amount of a composition comprising nanoparticles comprising paclitaxel and an albumin and ii) an effective amount of a platinum-based agent.

6. A method of identifying an individual with NSCLC likely to respond to treatment comprising a) a composition comprising nanoparticles comprising paclitaxel and an albumin and b) a platinum-based agent comprising: (A) assessing one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake; and (B) identifying the individual having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

7. A method for marketing a combination therapy comprising a) a composition comprising nanoparticles comprising paclitaxel and an albumin and b) a platinum-based agent for use in a NSCLC individual subpopulation, the methods comprising informing a target audience about the use of the combination therapy for treating the individual subpopulation characterized by the individuals of such subpopulation having one or more characteristics of NSCLC selected from the group consisting of (i) squamous cellular carcinoma, (ii) differential levels of caveolin-1 (CAV1), (iii) differential levels of SPARC, (iv) differential levels of hypoxia markers, (v) differential levels of tumor acidity, (vi) differential levels of gp60, (vii) differential levels of thymidylate synthase (TS), (viii) differential levels of S phase kinase-associated protein (Skp2), (ix) differential loss of heterozygosity (LOH) of single-nucleotide polymorphism (SNP), (x) differential Kras mutations, (xi) differential methylation of promoter region of tumor-related genes, and (xii) differential albumin uptake.

8. The method of any one of embodiments 2-7, wherein the differential levels of hypoxia are differential levels of carbonic anhydrase-9 (CA-9) or differential levels of LDH (e.g., LDH-5)

9. The method of any one of embodiments 2-7, where the differential levels of tumor acidity are differential levels of HIF-1α, differential levels of HIF-2α, or differential levels of differentiated embryo-chrondrocyte expressed gene 1 (DEC-1).

10. The method of any one of embodiments 1-9, wherein the effective amount of the composition comprising nanoparticles comprising paclitaxel and albumin is between about 50 mg/m² and about 125 mg/m².

11. The method of embodiment 10, the effective amount of the composition comprising nanoparticles comprising paclitaxel and albumin is about 50 mg/m², about 75 mg/m², or about 100 mg/m².

12. The method of any one of embodiments 1-11, wherein the composition comprising nanoparticles comprising paclitaxel and albumin is administered weekly.

13. The method of any one of embodiments 1-11, wherein the effective amount of the platinum-based agent is between about AUC=2 and about AUC=6.

14. The method of embodiment 13, wherein the effective amount of the platinum-based agent is AUC=3, AUC=4.5, or AUC=6.

15. The method of any one of embodiments 1-14, wherein the platinum-based agent is administered once every three weeks.

16. A method of treating NSCLC in an individual in need thereof, comprising administering to the individual (a) an effective amount of a composition comprising nanoparticles comprising paclitaxel and albumin; and (b) an effective amount of platinum-based agent, wherein the effective amount of the composition comprising nanoparticles comprising paclitaxel and albumin is 100 mg/m² administered weekly and the effective amount of the platinum-based agent is AUC=6 administered once every three weeks.

17. A method of treating NSCLC in an individual in need thereof, comprising administering to the individual a) an effective amount of a composition comprising nanoparticles comprising paclitaxel and an albumin; b) an effective amount of a platinum-based agent, and c) thoracic radiation, wherein the effective amount of the composition comprising nanoparticles comprising paclitaxel and albumin is 40 mg/m² or 60 mg/m² administered weekly, the effective amount of a platinum-based agent is AUC=2 administered weekly, and the thoracic radiation is 33 fractions by either 3D conformal or intensity-modulated techniques concurrently.

18. The method of any one embodiments 1-17, wherein paclitaxel in the nanoparticles are coated with albumin 19. The method of any one of embodiments 1-18, wherein the nanoparticles in the composition have an average diameter of no greater than about 200 nm 20. The method of embodiments 19, wherein the nanoparticles in the composition have an average diameter of less than about 200 nm 21. The method any one of embodiments 1-20, wherein the NSCLC is early stage NSCLC, non-metastatic NSCLC, primary NSCLC, advanced NSCLC, locally advanced NSCLC, metastatic NSCLC, NSCLC in remission, recurrent NSCLC, NSCLC in an adjuvant setting, or NSCLC in a neoadjuvant setting.

22. The method of any one of embodiments 1-21, wherein the NSCLC is Occult NSCLC, Stage 0 NSCLC, Stage I NSCLC, Stage II NSCLC, Stage IIIA NSCLC, Stage IIIB NSCLC, or Stage IV NSCLC.

23. The method of embodiment 22, wherein the NSCLC is Stage IIIB NSCLC or Stage IV NSCLC.

24. The method of any one of embodiments 1-23, wherein the method is first-line therapy.

25. The method of any one of embodiments 1-24, wherein the composition comprising nanoparticles comprising paclitaxel and albumin and platinum-based agent is administered parenterally.

26. The method of embodiment 25, wherein the composition comprising nanoparticles comprising paclitaxel and albumin and platinum-based agent is administered intravenously.

27. The method of any one of embodiments 1-26, wherein the composition comprising nanoparticles comprising paclitaxel and albumin is administered without any steroid premedication and/or without G-CSF prophylaxis.

28. The method of any one of embodiments 1-27, wherein the composition comprising nanoparticles comprising paclitaxel and albumin is administered over 30 minutes.

29. The method of any one of embodiments 1-28, wherein the platinum-based agent is carboplatin.

30. The method of any one of embodiments 1-29, wherein the individual is human.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

A Randomized, Phase III Trial of Nab-Paclitaxel and Carboplatin® Compared with Taxol® and Carboplatin® as First-Line Therapy in Patients with Advanced Non-Small Cell Lung Cancer (NSCLC)

The clinical study compared disease response (using RECIST guidelines) of Nab-paclitaxel plus carboplatin (AUC=6) vs. Taxol® and carboplatin (AUC=6) as first-line therapy in patients with advanced NSCLC. The clinical study also compared the frequency of toxicities grades using the CTCAE; progression-free survival (PFS); patient survival; duration of response in responding patients; evaluated pharmacokinetic parameters; and evaluated secreted protein acidic and rich in cysteine (SPARC) and other molecular biomarkers in tumor tissue and peripheral blood and determine their possible correlation with efficacy outcomes.

Treatment Design

This was a controlled, randomized, multicenter, Phase III study designed to evaluate the safety/tolerability and anti-tumor effect of intravenously administered Nab-paclitaxel/carboplatin combination therapy compared to that of Taxol/carboplatin combination therapy as first-line therapy in patients with NSCLC. Patients were randomized into one of two treatment arms.

Baseline evaluations were performed for all patients to determine study eligibility. These evaluations were completed within 28 days of randomization The following clinical evaluations were performed at baseline including: a) medical history (including specific information regarding any prior therapy and cardiac abnormality); b) serum β-hCG pregnancy test (for women of childbearing-potential only) was conducted to determine patient eligibility within 72 hours of the first administration of study drug; c) 12-lead ECG; d) collection of blood samples for evaluation of molecular biomarkers; e) CT scan of chest, liver, and abdomen and any other studies required for tumor imaging; f) a nuclear medicine bone scan were performed at baseline for any patient with clinical symptoms of possible bone metastases; g) CT scan of head or brain MRI (if symptomology of brain metastasis exist); h) height, weight, and calculation of BSA; i) physical examination and ECOG (Zubrod) performance status scale; j) concomitant medication evaluation (only medications taken within 30 days before the baseline visit were recorded); k) peripheral neuropathy assessment (physician and patient assessments); l) vital signs; m) CBC, differential, and platelet counts; and n) clinical chemistry panel (minimally including serum transaminases, bilirubin, alkaline phosphatases, glucose, BUN, and creatinine). The same mode of imaging was used at baseline and throughout the study. CT image preparation followed the specifications provided in the RECIST guidelines.

Treatment Phase Evaluations—

Patients returned within 7 days of randomization to begin Cycle 1 of study drug dosing. Visits where response assessments were not performed occurred within ±2 days of the planned visit date. Response assessments were performed every 6 weeks, at any time during the 6th week. If a dose was missed due to toxicity during a cycle, that dose was not to be made up and was to be recorded as a missed dose.

The following evaluations were performed prior to dosing or on Day 1 of each cycle including: a) physical examination (on Day 1 of each cycle or within 1 week prior to Day 1 of each cycle) and ECOG performance status scale; b) collection of blood samples for evaluation of molecular biomarkers (Day 1 of Cycles 3, 5, 7, etc); c) weight; d) concomitant medications evaluation; e) peripheral neuropathy assessment (on Day 1 of each cycle or within 1 week prior to Day 1 of each cycle); f) vital signs; g) adverse event evaluation (each dose); h) CBC, differential, and platelet counts; and i) clinical chemistry panel (minimally including serum transaminases, bilirubin, alkaline phosphatases, glucose, BUN, and creatinine).

The following evaluations were performed weekly (Days 8 and 15) during each cycle including: a) concomitant medications evaluation; b) adverse event evaluation; and c) CBC, differential, and platelet count. CT scans of the chest, liver, and abdomen and any other studies required for tumor imaging were done every 6 week while on treatment.

End-of-Study Evaluations—

An end of study evaluation was performed when treatment was completed for whatever cause. Laboratory and clinical evaluations were performed to assess adverse events at the time treatment was ended. Patients who had not developed progressive disease prior to going off treatment had tumor imaging studies performed every 6 weeks until tumor progression was documented.

End of treatment evaluations included the following: a) physical examination and ECOG performance status scale; b) CT scan of chest, liver, and abdomen and any other studies required for tumor imaging (only if required per the defined study imaging schedule); c) weight; d) concomitant medications evaluation; e) peripheral neuropathy assessment; f) vital signs; g) adverse event evaluation; h) CBC, differential, and platelet counts; and i) clinical chemistry panel (minimally including serum transaminases, bilirubin, alkaline phosphatases, glucose, BUN, creatinine).

Adverse Event (AE) Follow-Up Evaluations—

Any AE or serious adverse event (SAE) whose onset occurred between the first dose of study drug to 30 days after the last study drug or EOS (whichever is later) was collected. AE follow-up was conducted as follows: a) non-serious AEs, other than neuropathy, were followed for 30 days after the patient's last dose of study drug; b) neuropathy was followed until improvement to Grade 1 occurred, at least 3 months had elapsed without improvement or worsening, or the patient initiated any other anticancer therapy during follow-up; and c) all SAEs (regardless of relationship to study drug) were followed until resolution.

Follow-up evaluations included studies necessary to document the resolution or persistence of any unresolved AEs and included, for example: a) physical examination and ECOG performance status scale; b) CT scan of chest, liver, and abdomen and any other studies required for tumor imaging; c) weight; d) concomitant medications evaluation; e) peripheral neuropathy assessment; f) vital signs; g) AE event evaluation; and h) CBC, differential, platelet count, and clinical chemistry panel.

Post-Study Follow-Up for Patient Survival—

Patient status continued to be evaluated post-study by telephone monthly for 6 months, and then every 3 months thereafter for 12 months (total of 18 months follow-up), to obtain post-study survival data.

Withdrawal—

Patients withdrew from this study if any of the following occurred: a) progressive disease; b) development of toxicity that was unacceptable in the opinion of the investigator; c) patient declined to continue therapy; d) if, following the 2nd dose reduction, there was a recurrence of Grade 4 neutropenia, or any other hematologic toxicity that was Grade 3 or 4, or any Grade 3 or 4 nonmyelosuppressive AE, unless, at the discretion of the investigator, there was evidence of continuing benefit to the patient that outweighed the risk of recurrent toxicity; d) initiation of other anticancer therapy;

or e) in the investigator's judgment, it was in the patient's best interest to discontinue the study.

A summary of the study protocol is provided in Table 1.

therapy was completed 12 months prior to starting the study); 6) expected survival of >12 weeks; 7) ECOG performance status 0 or 1; 8) patient had the following blood

TABLE 1

Time and Events Schedule

| Assessment | Baseline | CYCLE 1, 3, 5, etc | | | CYCLE 2, 4, 6, etc | | | Every 6 Weeks | EOS[A] | AE Follow-up[B] | Post-study Progression/ Survival |
|---|---|---|---|---|---|---|---|---|---|---|---|
| | | Day 1 | Day 8 | Day 15 | Day 1 | Day 8 | Day 15 | | | | |
| Informed Consent | X | — | — | — | — | — | — | — | — | — | — |
| Medical History | X | — | — | — | — | — | — | — | — | — | — |
| Serum β-hCG[C] | X | — | — | — | — | — | — | — | — | — | — |
| Electrocardiogram (ECG)[D] | X | — | — | — | — | — | — | — | — | — | — |
| Consent to use diagnostic tumor biopsy for SPARC analysis | X | — | — | — | — | — | — | — | — | — | — |
| Collection of blood samples for evaluation of other molecular biomarkers[E] | X | X | — | — | — | — | — | — | — | — | — |
| PK Sampling (Arm A) | — | X | — | — | — | — | — | — | — | — | — |
| CT Scan of Chest/Liver/Abdomen[F] & any other studies required for tumor imaging | X | — | — | — | — | — | — | X[G] | X[H] | — | X |
| CT Scan of Head or Brain MRI[I] | X | — | — | — | — | — | — | — | — | — | — |
| Bone Scan[J] | X | — | — | — | — | — | — | — | — | — | — |
| BSA Calculation and Height[K] | X | — | — | — | — | — | — | — | — | — | — |
| Weight | X | X | — | — | X | — | — | — | X | X | — |
| Physical Examination[L]; ECOG status | X | X | — | — | X | — | — | — | X | X | — |
| Concomitant Medication Evaluation | X | X | X | X | X | X | X | — | X | X | — |
| Peripheral Neuropathy Assessment[M] | X | X | — | — | X | — | — | — | X | X | — |
| Vital Signs | X | X | — | — | X | — | — | — | X | X | — |
| Adverse Event Evaluation | — | X | X | X | X | X | X | — | X | X | — |
| CBC, Differential, Platelet Count | X | X | X | X | X | X | X | — | X | X | — |
| Clinical Chemistry Panel | X | X | — | — | X | — | — | — | X | X | — |
| Progression/Survival Follow-up[N] | — | — | — | — | — | — | — | — | — | — | X |

[A]EOS = End of Study. When patient came off study, the indicated tests were done. Repeat studies for tumor response only if required per the defined study imaging schedule.
[B]Reporting of AEs/SAEs continued through 30 days after the patient discontinued the study drug or EOS, whichever came later. Any AEs/SAEs that began during this time were followed. If there were no AEs or SAEs ongoing at the EOS visit, follow-up was done by telephone to the patient weekly until 30 days from last dose of treatment.
[C]Pregnancy test required for women of child-bearing potential only. Serum β-hCG pregnancy test was performed to assess patient eligibility within 72 hours of the first administration of study drug.
[D]ECG was performed at baseline and at any other stage in the cycle as determined to be clinically significant by investigator
[E]Sample for molecular biomarkers were obtained within 2 weeks prior to first administration of study drug (including Day 1 of Cycle 1, prior to administering study chemotherapy). All subsequent samples were collected on Day 1 of odd numbered cycles (Cycles 3, 5, 7, etc), prior to administration of study drug.
[F]All patients had radiographically documented measurable tumor(s) by RECIST criteria: CT scan of the thorax, abdomen, and liver were performed at baseline, every 6 weeks (at any time during the 6th week) while on-treatment, and EOS (only if required per the defined study imaging schedule). The method of assessment chosen at baseline to follow tumors should remain consistent throughout study duration.
[G]Obtained scans for response assessment every 6 weeks while on-treatment.
[H]Restaging studies were also to be done at the EOS visit only if required per the defined study imaging schedule, unless there was otherwise clear clinical evidence of progression.
[I]A CT scan of head or brain MRI was performed if symptoms of brain metastasis existed.
[J]A nuclear medicine bone scan was performed at Baseline for any patient with clinical symptoms of possible bone metastases. All areas identified on the bone scan as possible metastases, which were inconclusive, then had plain film X-rays done to verify they were indeed metastases. These confirming X-ray studies were only done at Baseline, and did not need to be repeated at subsequent bone scans. Bone scans were repeated every 12 weeks and at the time an objective response was initially documented or initially confirmed.
[K]BSA was calculated at baseline and recalculated if body weight changed by more than 10% from baseline.
[L]On Day 1 of each cycle or within 1 week prior to Day 1 of each cycle.
[M]On Day 1 of each cycle or within 1 week prior to Day 1 of each cycle. The occurrence of peripheral neuropathy was reported by the investigator per protocol as an AE or SAE.
[N]Post-study follow-ups provided patient survival. Phone follow-ups were performed monthly for 6 months and every 3 months thereafter for 12 months (total of 18 months follow-up). For patients who had not yet progressed since the start of the study, progression-free survival follow-up were performed every 6 weeks by repeating studies required for tumor imaging. Bone scans were conducted every 12 weeks if being used to document non-target lesions.

Inclusion/Exclusion Criteria

A patient was eligible for inclusion in this study only if all of the following criteria were met: 1) histologically or cytologically confirmed stage IIIB or IV NSCLC; 2) male or non-pregnant and non-lactating female, and ≥18 years of age (if a female patient is of child-bearing potential, as evidenced by regular menstrual periods, she must have a negative serum pregnancy test (β hCG) documented within 72 hours of the first administration of study drug, and if sexually active, the patient must agree to utilize contraception considered adequate and appropriate by the investigator); 3) no other current active malignancy; 4) radiographically-documented measurable disease (defined by the presence of at least one radiographically documented measurable lesion); 5) patients must have received no prior chemotherapy for the treatment of metastatic disease (adjuvant chemotherapy permitted providing cytotoxic chemo- counts at baseline: a) ANC≥1.5×10$^9$ cells/L; b) platelets ≥100×10$^9$ cells/L; and c) Hgb≥9 g/dL; and 9) patient had the following blood chemistry levels at baseline: a) AST (SGOT), ALT (SGPT)≤2.5× upper limit of normal range (ULN) or ≤5.0×ULN if liver metastases; b) total bilirubin≤ULN, and c) creatinine≤1.5 mg/dL.

A patient was ineligible for inclusion in this study if any of the following criteria applied: 1) evidence of active brain metastases, including leptomeningeal involvement (prior evidence of brain metastasis permitted only if treated and stable, off therapy, for at least 1 month); 2) the only evidence of disease was non-measurable; 3) patient had pre-existing peripheral neuropathy of Grade 2, 3, or 4 (per CTCAE); 4) patient received radiotherapy in last 4 weeks, except if to a non-target lesion only (prior radiation to a target lesion was permitted only if there had been clear progression of the lesion since radiation was completed); 5) patient had a clinically significant concurrent illness; 6) patient had received treatment with any investigational drug within the previous 4 weeks; 7) patient had a history of allergy or hypersensitivity to any of the study drugs; 8) patient had serious medical risk factors involving any of the major organ systems such that the investigator considers it unsafe for the patient to receive an experimental research drug; or 9) patient was enrolled in any other clinical protocol or investigational trial that involved administration of experimental therapy and/or therapeutic devices.

Dosages and Administration

Patients with NSCLC were randomized into one of 2 treatment arms. Treatment Arm A were assigned for administration of Nab-paclitaxel/carboplatin and Treatment Arm B were assigned for the administration of Taxol/carboplatin. There were approximately 525 intent-to-treat (ITT) patients per arm.

Nab-paclitaxel or Taxol® was administered in this study only in combination with carboplatin, i.e., no other additional chemotherapeutic agents were administered with the study drug. Patients could not participate in any other clinical protocol or investigational trial that involved administration of experimental therapy and/or the use of investigational devices with therapeutic intent while enrolled in this study.

Supportive care, such as anti-emetic and pain medications, and erythropoietin could be administered. Concurrent treatment with bisphosphonates was allowed. G-CSF was administered according to the guidelines described herein.

Patients could continue on treatment in the absence of progressive disease and unacceptable toxicity as long as their treating physician felt it was in their best interests to do so. In general, assuming adequate tolerability of the regimen, it was encouraged that patients received at least 6 cycles of treatment to permit adequate evaluation of the treatment regimen. Patients, who stopped treatment prior to developing progressive disease, were followed without further treatment until progressive disease was documented or until the treating physician felt additional treatment was required.

Treatment Arm A (Nab-Paclitaxel/Carboplatin)

During the Treatment Phase, patients randomized to this arm intravenously received Nab-paclitaxel 100 mg/m$^2$ administered weekly (Days 1, 8 and 15 of each cycle) over approximately 30 minutes without any steroid premedication and without G-CSF prophylaxis (unless modified as described herein) followed by carboplatin at AUC=6 on Day 1 of each cycle, repeated every 3 weeks. Carboplatin was intravenously infused over 30-60 minutes after the Nab-paclitaxel infusion.

A maximum of two dose reductions were allowed from the original dose: a) 1st dose reduction: Decreased Nab-paclitaxel to 75 mg/m$^2$ and carboplatin to an AUC of 4.5 (25% reduction) and b) 2nd dose reduction: Decreased to Nab-paclitaxel to 50 mg/m$^2$ and carboplatin to an AUC of 3.0 (50% reduction).

Nab-paclitaxel dosing was not administered at the start of the study or on Day 1 of a cycle until the absolute neutrophil count returned to $\geq 1.5 \times 10^9$ cells/L and the platelet count returned to $\geq 100 \times 10^9$ cells/L. For each subsequent weekly dose of Nab-paclitaxel, patients had an ANC$\geq 0.5 \times 10^9$ cells/L and platelets $>50 \times 10^9$ cells/L. If the ANC and platelets were not adequate for that week's treatment, the dose was to be held and resumed the following week, provided the ANC was $\geq 0.5 \times 10^9$ cells/L and platelets were $>50 \times 10^9$ cells/L. Reduce subsequent dose only if criteria below were met. Nab-paclitaxel was not administered if hepatic function parameters were out of the range that was established for entry into the study.

Treatment Arm B (Taxol/Carboplatin)

During the Treatment Phase, patients randomized to this arm intravenously received Taxol® 200 mg/m$^2$ administered over 3 hours with standard premedication followed by carboplatin at AUC=6, repeated every 3 weeks (both drugs given on Day 1 of each cycle). Carboplatin was infused by IV over 30-60 minutes.

A maximum of 2 dose reductions were allowed from the original dose: a) 1st dose reduction: Decreased Taxol® to 150 mg/m$^2$ and carboplatin to an AUC of 4.5 (25% reduction) and b) 2nd dose reduction: Decreased to Taxol® 100 mg/m$^2$ and carboplatin to an AUC of 3.0 (50% reduction).

Taxol® and carboplatin were not administered at the start of each cycle until the absolute neutrophil count returned to $\geq 1.5 \times 10^9$ cells/L and the platelet count returned to $>100 \times 10^9$ cells/L. Neither drug was administered at the beginning of a cycle if hepatic function parameters were out of the range that was established for entry into the study.

Nab-Paclitaxel

Each single-use 50 mL vial contained 100 mg paclitaxel and human albumin (HA) as a stabilizer. Each Nab-paclitaxel vial was reconstituted by using a 50 or 60 cc sterile syringe to inject 20 mL of 0.9% Sodium Chloride Injection or equivalent into each vial over a period of not less than 1 minute (5 mg/mL suspension). The use of in-line filters was generally not necessary; if used, in-line filters with pore sizes of <15 microns (15 μm) were not used.

Taxol

See Taxol® package insert (current version of Prescribing Information is provided in the Study Manual) for description and formulation. Taxol® (paclitaxel) was diluted in 0.9% Sodium Chloride Injection, USP; 5% Dextrose Injection, USP; 5% Dextrose and 0.9% Sodium Chloride Injection, USP; or 5% Dextrose in Ringer's Injection to a final concentration of 0.3 to 1.2 mg/mL. Taxol® was administered through an in-line filter with a microporous membrane not greater than 0.22 microns.

Carboplatin

The chemical name for carboplatin is cis-diammine(cyclobutane-1,1-dicarboxylate-O,O')platinum(II). Carboplatin lyophilized powder was reconstituted for IV infusion using the appropriate diluent and volume as directed in the package insert. Dosing of carboplatin was based on the Calvert formula: carboplatin dose (mg)=(Target AUC)×(GFR+25). For the purposes of this protocol, the GFR is considered to be equivalent to the creatinine clearance (calculated by the method of Cockcroft and Gault, 1976). To calculate dose of carboplatin (total mg, not mg/m$^2$): mg carboplatin=(6)×(CrCl+25). For obese patients, defined as having a Body Mass Index (BMI)>30 kg/m2, use lean body weight in kilograms in the above formula to calculate creatinine clearance, instead of actual body weight.

Dose Modifications (All Arms)

Rules for Dose Omission-Day 1 dose missed: If the dose held or missed was to be given on Day 1 of the next cycle, the next cycle was not considered to start until the day the first dose was actually administered to the patient (i.e., D1-D8-D15, X-D1-D8-D15, etc.). Day 8 dose was missed: Cycle continued per protocol, with one dose not given (i.e., D1-D8-D15, D1-X-D15, D1-D8-D15, etc.). Day 15 was administered as per cycle calendar if counts and chemistries permitted. Day 15 dose missed: Cycle continued per protocol, with one dose not given (i.e., D1-D8-D15, D1-D8-X, D1-D8-D15, etc.). Day 1 was administered as per cycle calendar if counts and chemistries permitted.

Hematologic Toxicity—

Study drugs were only administered if hepatic function was within the parameters established in the eligibility criteria. Hepatic toxicity from taxanes could occur but it was uncommon. Therefore, hepatic dysfunction that occurs while the patient was on study prompted an evaluation to determine the cause, including the possibility of progressive metastatic disease and hepatotoxicity from concurrent medications. The table below provided a guideline for implementing dose reductions and growth factor treatment for hematologic toxicity for both study arms:

TABLE 2

Use of G-CSF and Dose reductions for Hematologic Toxicity

| Adverse Event | Occurrence | Action to be Taken |
|---|---|---|
| ANC < 500 cells/mm$^3$ (nadir count) with neutropenic fever > 38° C. OR Delay of next cycle due to persistent neutropenia** (ANC < 1500 cells/mm$^3$) OR Neutropenia < 500 cells/mm3 for > 1 week | $1^{st}$ Occurrence | Dose reduction to the next lower level were required for subsequent cycles once ANC is ≥1500 cells/mm$^3$. |
| | $2^{nd}$ Occurrence | Dose reduction to the next lower level were required for subsequent cycles once ANC is ≥1500 cells/mm$^3$. |
| Thrombocytopenia Grade 3 or Grade 4* | $1^{st}$ Occurrence | Dose reduction to next lower level; initiation of next cycle is delayed until platelet count was 100,000 cells/mm$^3$. |
| | $2^{nd}$ Occurrence | Discontinued treatment |

*See NCI CTCAE Scale for definition of Grade 3 and Grade 4 events.
**Maximum of 7 days post scheduled Day 1 dose of next cycle.

Colony Stimulating Factor Administration—

Colony stimulating factors could be given according to institutional guidelines for the treatment of neutropenic fever or infections associated with neutropenia.

Hypersensitivity Reactions—

Minor symptoms such as flushing, skin reactions, dyspnea, hypotension, or tachycardia could require temporary interruption of the infusion. However, severe reactions, such as hypotension requiring treatment, dyspnea requiring bronchodilators, angioedema or generalized urticaria required immediate discontinuation of study drug administration and aggressive symptomatic therapy. Patients who develop severe hypersensitivity reactions to any of the study drugs were not re-challenged with the drug. Treatment with the remaining drug alone continued.

Dose Reductions for Non-hematologic Toxicity—

Table 3 provided a guideline for dose reductions for non-hematologic toxicity.

TABLE 3

Dose Reductions for Non-hematologic Toxicity

| Adverse Event | Occurrence | Action to be Taken |
|---|---|---|
| Grade 2 or 3 cutaneous toxicity | $1^{st}$ Occurrence | Interrupted treatment until toxicity improved to Grade 0 or 1. When treatment was resumed, reduced by 1 dose level. |
| | $2^{nd}$ Occurrence | |
| | $3^{rd}$ Occurrence | Discontinued treatment |
| Grade 4 cutaneous toxicity | $1^{st}$ Occurrence | Discontinued treatment |
| Grade 3 mucositis or diarrhea | $1^{st}$ Occurrence | Interrupted treatment until toxicity improved to Grade 0 or 1. When treatment was resumed, reduced by 1 dose level. |
| | $2^{nd}$ Occurrence | |
| | $3^{rd}$ Occurrence | Discontinued treatment |
| Grade 4 mucositis or diarrhea | $1^{st}$ Occurrence | Discontinued treatment |
| Any other Grade 3 or 4 non-hematologic toxicity excluding alopecia | $1^{st}$ Occurrence | Interrupted treatment until toxicity improved to Grade 0, 1 or 2.* When treatment was resumed, reduced by 1 dose level. |
| | $2^{nd}$ Occurrence | |
| | $3^{rd}$ Occurrence | Discontinue treatment |

*This decision depended upon the type of non-hematologic toxicity seen and which course was medically most sound in the judgment of the physician investigator.

Peripheral Neuropathy—

Treatment was withheld in patients who experienced ≥Grade 3 peripheral neuropathy. Treatment could resume at the next lower dose level (see Dose Reductions above) in subsequent cycles after the peripheral neuropathy improves to ≤Grade 1. The time to resolution to Grade≤1 was the adverse event duration used for adverse event reporting.

Cutaneous Toxicity—

Patients who developed Grade 2 or 3 cutaneous toxicity had their dose reduced by 1 dose level. If the patient continued to experience these reactions, despite dose reduction, treatment was discontinued. Patients who develop Grade 4 cutaneous toxicity had treatment discontinued.

Gastrointestinal Toxicity—

If Grade 3 mucositis or diarrhea occurred, study drug was withheld until resolution to ≤Grade 1, then reinstituted at the next lower dose level (see Dose Reductions). Patients who develop Grade 4 mucositis or diarrhea had treatment discontinued.

Other Toxicities—

If toxicities were ≤Grade 2, the toxicity was managed symptomatically if possible, and the patient re-treated without dose reduction. If toxicities were ≥Grade 3, treatment was withheld until resolution to Grade 0, 1 or 2, or baseline if baseline was greater than Grade 1, then reinstituted, if medically appropriate, at the next lower dose level (see Dose Reductions). Recurrence of a Grade 3 or 4 toxicity following 2 dose reductions necessitated discontinuation of treatment.

Dose Delays—

Patients whose next treatment was delayed for ≥3 weeks due to persistent toxicity had subsequent doses reduced by 1 dose level.

Discontinuation from Study—

If an adverse event that required dose reduction recurred after the dose had been reduced twice, the patient generally had treatment discontinued unless, at the discretion of the investigator, there was evidence of continuing benefit to the patient that outweighed the risk of recurrent toxicity.

Efficacy Endpoints

The primary efficacy endpoint was the percentage of patients who achieve an objective confirmed complete or partial response based on the blinded radiological review using RECIST response guidelines. Key secondary efficacy endpoints included a) progression tree survival (PFS); b) patient survival; c) percentage of patients with stable disease for ≥16 weeks or confirmed complete or partial response (i.e., disease control rate); d) duration of response in responding patients; and e) correlation of SPARC and other molecular biomarkers with efficacy outcomes.

Tumors were assessed in the study by imaging studies every 6 weeks during therapy (at any time during the 6th week). For patients who have not progressed by end-of-treatment, repeat imaging was performed every 6 weeks until tumor progression is documented. Secondary analyses included progression-free survival, duration of response in responding patients, disease control rate and patient survival. Safety and tolerability were monitored through reporting of adverse events and serious adverse events, laboratory abnormalities, and incidence of patients experiencing dose modifications, dose interruptions, and/or premature discontinuation of study drug. Patients were considered responders if they achieved an objective complete or partial response according to RECIST guidelines. Patients who discontinue early from the study or who are randomized but do not receive treatment were not replaced.

Measurable and Non-Measurable Lesion

The definition of a measurable lesion at baseline was dependent on the technical factors of the imaging studies that were used to evaluate the patient. The recommendations for the imaging parameters were based on the American College of Radiology (ACR) Practice Guidelines and Technical Standards. The proposal for modifying the size of measurable lesions at baseline to two (2) times the reconstruction interval of the baseline/screening studies was consistent with the RECIST definition for a measurable lesion. Lesions that could be accurately measured in at least one (1) dimension with the longest diameter (LD)≥twenty (20) mm with conventional techniques when the conventional scans were performed with a reconstruction interval of ten (10) mm or less were measurable lesions. Lesions that could be accurately measured in at least one (1) dimension with the longest diameter (LD) being two (2) times the reconstruction interval (RI) of the spiral CT scan. The minimum size of a measurable lesion is ten (10) mm. The definition for target disease did not change and was determined on the basis of the baseline scan.

All other lesions that did not meet the criteria for measurable disease as described above as well as other truly non-measurable lesions, were considered non-measurable.

Target and Non-Target Lesion Response

Response at each time point was assessed as a combination of the target and non-target responses as well as the presence of new lesions.

Up to ten (10) target lesions, a maximum of five (5) per organ, were chosen for measurement over the course of the study. The distribution of these target lesions was representative of the subject's overall disease. Target lesions were not chosen from a previously irradiated area unless lesions in those areas had documented progression. Target lesions were measurable at baseline. For any target lesion at any time point, measurements were taken and recorded unidimensionally. The longest dimension of each target lesion was measured and recorded. The longest dimension of the target lesions was summed to obtain the Sum of the Longest Diameters (SLD). The baseline SLD was used as reference to further characterize the objective tumor response of the target lesions. For the consideration of progressive disease, the nadir of the SLD for the target lesions was used as reference.

For cases where there was no target lesion identified, tumor assessment for progression was done based on non-target lesion assessments or the development of new lesions. Response (PR or CR) and SD was not assessed in subjects where target lesions were not identified at baseline.

The following conventions were applied in selecting target lesions in patients who have received prior radiation therapy: a) prior axillary radiation (i.e., prior radiation history including the term "axilla", "axillary" or other related term(s)) did not preclude the selection of measurable lesions in the chest wall or thorax as target lesions); b) prior breast (i.e., prior radiation history including the term "breast") or chest wall radiation (i.e., prior radiation history including the term "chest wall" or other related term(s)) precluded the selection of chest wall lesions as target disease for chest wall lesions ipsilateral to the site of the chest wall radiation; c) prior bone radiation (e.g., vertebral, rib, pelvis, femur, etc.) did not preclude the selection of measurable lesions in adjacent structures unless signs of radiation injury were evident (e.g., scarring); and d) prior soft tissue radiation (e.g., supraclavicular radiation, radiation of internal mammary lymph nodes, etc.) precluded the selection of measurable disease in the site of radiation unless the lesions were new since radiation was completed.

All of the sites of disease present at baseline not classified as target lesions were classified as non-target lesions. Non-target lesions were qualitatively assessed at each subsequent time point. Examples of non-target lesions included: a) all bone lesions, irrespective of the modality used to assess them; b) leptomeningeal disease; c) lymphangitis of the skin or lung; d) cystic lesions; e) irradiated lesions that have not shown progression; f) measurable lesions beyond the maximum number of 10; g) groups of lesions that are small and numerous; and h) pleural effusion/pericardial effusion/ascites.

Unequivocal new lesions were those that were not present at baseline. At each time point, the presence of new lesions was determined. New multi-focal or miliary disease of any size were considered a new lesion. Lesions that were encountered (subsequent to the baseline) in anatomic locations that were not scanned at baseline were considered new lesions and represented progressive disease. Lesions that were present, which subsequently resolved and then recurred, were considered new lesions and represented progressive disease.

Response

Response was determined according to Response Evaluation Criteria in Solid Tumors (RECIST) guidelines. Therasse P. et al. *J Natl Cancer Inst.* 2000, 92:205-216. The study employed RECIST guidelines with adjustments based on current practices of the medical community. The charter of the blinded radiological review which was conducted by Icon Medical Imaging outlines the modifications to the original RECIST guidelines.

Antitumor response was defined as the percent of patients who achieved an objective confirmed response (complete or partial response). Disease control rate (SD for at least 16 weeks or confirmed CR or PR) also was reported. The primary efficacy endpoint was the percentage of patients who achieve an objective confirmed complete or partial response based on a blinded radiological assessment of response. Superiority of Nab-paclitaxel/carboplatin to Taxol/carboplatin was established when the lower bound of the 95.1% CI of pA/pT>1.0. In addition to the ratio of response rates (pA/pT) and it's 95.1% CI, the following were presented for each treatment regimen: sample size, overall rate response, and 95% CI of the response rate. Treatment regimen comparison of response rates were tested using the chi-square test.

Percentage change in SLD was evaluated by the following formulae: 1) when determining complete response or partial response: ((Post value−Baseline value)/Baseline value)×100 and 2) when determining progressive disease: (Post value−Nadir value since treatment started)/(Nadir value since treatment started)×100.

The following definitions were used to evaluate response based on target lesions at each time point after baseline: Complete Response (CR): Disappearance of all target lesions. Partial Response (PR): At least a 30% decrease in the SLD of target lesions, taking as reference the baseline SLD. Stable Disease (SD): Neither sufficient shrinkage of target lesions to qualify for PR, nor sufficient increase to qualify for PD, taking as reference the nadir SLD since the treatment started. Progressive Disease (PD): At least a 20% increase in the SLD of target lesions, taking as reference the nadir SLD recorded since the treatment started, or, the presence of one or more new lesions. Unable to Evaluate (UE): A target lesion present at baseline which was not measured or which was unable to be evaluated leading to an inability to determine the status of that particular tumor for the time point in question. If the SLD cannot be determined at a time point, and the rules for PD do not apply, a response of CR, PR or SD could not be assigned for that time point and the time point response was UE. Not Applicable (NA): No target lesions were identified at baseline. Patients with no target lesions identified at baseline could not be assessed for response. These patients were assessed for progression only. Not Done (ND): Scans were not performed at this time point to evaluate the target lesions.

Each non-target lesion was qualitatively evaluated at each time point. Response of each lesion at each time point was assessed with respect to the baseline status. Progression was assessed with respect to nadir size of the non-target lesions. The overall non-target lesion response for each time point was assessed as the worst case for the non-target lesions for that particular time point. If a non-target lesion was classified as UE/ND, the non-target response was UE/ND unless progression was identified in the available non-target lesions. Response assessments were defined as follows: Complete Response (CR): Disappearance of all non-target lesions. Stable Disease (SD): The persistence of one or more non-target lesions not qualifying for CR or PD. Progressive Disease (PD): The "unequivocal progression" of existing non-target lesion(s) or appearance of one or more new lesion(s) was considered progressive disease. If PD for the subject was to be assessed for a time point based solely on the progression of non-target lesion(s), then additional criteria are required to be fulfilled. In this instance, the lesion(s) upon which the assessment of PD was being made must be retrospectively assessed from baseline (or the nadir) and compared to the time point in question. PD of non-target lesion(s) in this instance was assessed when the SLD of the lesion(s) had increased by 20% or greater and the lesion(s) measured greater than or equal to 10 mm in longest dimension (LD) at the time of progression. If the nontarget lesion(s) did not meet the quantitative criteria as described, they were not assessed as having progressed. For pleural fluid, ascites, pericardial effusions and other fluid collections, progression was assessed in an otherwise stable or responding subject when the increase in the fluid was estimated to be greater than 500 cc, and was not attributable to a benign cause identified radiographically. Unable to Evaluate (UE): Any non-target lesion present at baseline which was not measured or was unable to be evaluated leading to an inability to determine the status of that particular tumor for the time point in question. Not Applicable (NA): No non-target lesions were identified at baseline. Not Done (ND): Scans were not performed at this time point to evaluate the non-target lesions.

Disease control rate (SD for ≥16 weeks or confirmed CR or PR) was analyzed in the same manner as objective response.

Progression Free Survival

The final analysis for PFS was conducted once 70% of patients had an event of disease progression or death (for any cause). This was equivalent to 735 events which provides 85% power with a two-sided Type 1 error of 0.049 to detect a Nab-paclitaxel/carboplatin to Taxol/carboplatin hazard ratio (HRA/T) of 0.80.

PFS was analyzed using Kaplan-Meier methods. PFS was defined as the time from the day of randomization to the start of disease progression or death (for any cause), whichever occurs first, based on the blinded radiological review assessment of response. PFS for patients who achieved an objective confirmed complete or partial response was presented as a measure of duration of response.

Patients who did not have disease progression or have not died were censored at the last known time that the patient was progression free. In the event that palliative radiotherapy or surgery at lesion sites occurs, the patient was censored at the last assessment without documented progression prior to the date of radiotherapy or surgery. In follow-up, patients who began new anti-cancer therapy (other than radiotherapy) prior to documented progression were censored at the last assessment where the patient was documented as progression free.

To assess the impact on PFS of response assessments not occurring at the regularly scheduled assessment times, the frequency of these unscheduled/off-scheduled assessments was presented for each treatment regimen. In addition, a confirmatory sensitivity analysis was performed where patients with events and censorings that occur at a time other than the regularly scheduled assessment, had PFS time based on the date of the next regularly scheduled assessment rather than the actual off-schedule date. To assess the impact of a single missed response assessment prior to a visit with documented disease progression, the frequency of missed response assessments was presented by treatment regimen. In addition, two confirmatory sensitivity analyses were conducted. In the first sensitivity analysis, these patients were censored at the last visit where the patient was documented to be progression free. In the second sensitivity analysis, these patients were considered to have progressed at the time of the missed response assessment.

The Nab-paclitaxel/carboplatin to Taxol/carboplatin hazard ratio (HRA/T) and it's 95.1% CI for PFS were evaluated. The following also were evaluated for each treatment regimen: sample size, number and percentage of patients with disease progression or death, median PFS, and a 95% CI for the median PFS. The Kaplan-Meier curve for PFS was evaluated for each treatment regimen and differences in the curves were tested using the log-rank test.

Patient Survival

The final analysis for patient survival was conducted once 70% of patients had died. This was equivalent to 735 deaths which provides 85% power with a two-sided Type 1 error of 0.049 to detect a Nab-paclitaxel/carboplatin to Taxol/carboplatin hazard ratio (HRA/T) of 0.80. Patient survival was defined as the time from the day of randomization to patient death (for any cause). Patient survival was analyzed in a similar manner to PFS.

Safety/Tolerability Endpoints

The safety/tolerability endpoints were the incidence of treatment-emergent AEs and SAEs, laboratory abnormalities, and incidence of patients experiencing dose modifications, dose interruptions, and/or premature discontinuation of study drug.

AEs occurring during the study were graded according to the NCI Common Terminology Criteria for Adverse Events v3.0 (CTCAE) (see http://ctep.cancer.gov/reporting/ctc.html), where applicable. AEs that were not included on the toxicity scale were designated as Grade 1=mild, Grade 2=moderate, Grade 3=severe, Grade 4=life-threatening, and Grade 5=death. AEs that were determined not to be possibly, probably, or definitely related to study drug did not require further evaluation but were recorded. Study medications could be interrupted for an AE at the discretion of the investigator. Patients requiring toxicity management were assessed and evaluated at least weekly as indicated by the severity of the event.

According to the NCI CTCAE system of adverse event grading, laboratory values of Grade 3 or 4 were described as "severe" or "life-threatening." For example, a neutrophils count<500/mm$^3$ would meet laboratory criteria as Grade 4 ("life-threatening"). This description was not always synonymous with the assessment of the "serious" criteria of an AE as "life threatening". Definition of AE and SAE are provided herein.

In order for AEs to be considered serious by "life-threatening" criteria, it was medically judged as possessing "an immediate risk of death from the event as it occurred," not because of the theoretical potential for life-threatening consequences. In the case of a neutrophil count<500/mm$^3$, the AE would be captured as an AE of Grade 4 neutropenia, but it was not automatically considered a SAE unless the investigational physician determined this represented an immediately life-threatening event for the patient. Specifically, uncomplicated Grade 4 neutropenia was not reported as a SAE. Neutropenia associated with fever, infection, or hospitalization was reported as a SAE.

Difference between Nab-paclitaxel/carboplatin and Taxol/carboplatin were compared using the Cochran-Mantel-Haenszel test.

Patients in the treated population were followed for the development of AEs from study drug initiation through the end of study or 30 days after the end of treatment, whichever was longer. Only patients with clear documentation that no study drug was administered could be excluded from the treated population.

Peripheral neuropathy (PN) (sensory or motor) was reported by grade according to the NCI CTCAE. When the grade of the PN changes (i.e., increases or decreases), the stop date on the existing AE should be entered and a new AE started, reflecting the new grade.

Pharmacokinetic Endpoints

PK measurements of Nab-paclitaxel were taken around the 0.25, 3.5, and 24 hr post-infusion-end time points for patients randomized to receive Nab-paclitaxel/carboplatin in Russia, Ukraine, the United States, and Canada (approximately 100 patients). The pharmacokinetic parameters were the maximum plasma drug concentration ($C_{max}$), the area under the plasma concentration versus time curve (AUC and $AUC_{inf}$), the half-life of the apparent terminal portion of the concentration versus time curve ($T_{1/2}$), the total body clearance (CL), and the volume of distribution ($V_z$).

A sparse pharmacokinetic (PK) sampling method coupled with three-compartment model analysis was used to determine the PK parameters. The AUC is an important indicator of drug availability or the total amount of metabolite present.

To assess the relationship between drug exposure and safety, the correlation of nadir ANC with PK parameter estimates (e.g. absolute AUCinf) was evaluated using a linear regression analysis with an effect for PK parameter in the model. Transformation of nadir ANC data was considered if these data were non-normally distributed. To assess the relationship between drug exposure and efficacy, the correlation of objective confirmed response (based on blinded radiological review) with PK parameter estimates was evaluated using a logistic regression analysis with an effect for the PK parameter in the model. To assess the relationship between drug exposure and biomarkers, the correlation of each biomarker with PK parameter estimates was evaluated using a logistic regression analysis with an effect for the PK parameter in the model for biomarkers with binary outcomes and was evaluated using a linear regression analysis with an effect for PK parameter in the model for biomarkers with a continuous outcomes.

Laboratory Assessments

Hematology Parameters—

To investigate the maximal degree of myelosuppression, the CTCAE grade for WBC, ANC, platelet count, and hemoglobin concentration were summarized by the most severe grade for the first cycle of therapy and by the most severe grade anytime during therapy for each treatment regimen; testing of treatment regimen differences were performed using the CMH test. The incidence of patients with CTCAE hematology values of Grade 3 or 4 that occurred after the first dose of study drug was presented for each group. Data for patients with Grade 3 or 4 hematology values were listed.

Clinical Chemistry—

Liver and renal functions were summarized using the CTCAE for ALT, AST, total bilirubin, and creatinine. The number and percentage of patients who have each CTCAE grade were summarized by the most severe grade for the first cycle of therapy and by the most severe grade anytime during therapy for each treatment regimen; testing of treatment regimen differences was performed using the CMH test. The incidence of patients with CTCAE chemistry values of Grade 3 or 4 that occurred after the first dose of study drug was presented for each group. Data for patients with Grade 3 or 4 chemistry values were listed.

Evaluation of Molecular Biomarkers

Tumor biomarkers (mRNA and DNA) were studied to assess prognostic utility in identifying responders and non-responders in both treatment arms. Molecular biomarkers were assessed on archival paraffin-embedded (PE) tumor tissue of patients entered into the trial. Blood samples for the evaluation of molecular biomarkers were collected within two weeks prior to starting treatment, and then every other cycle (Day 1 of Cycles 3, 5, 7, etc.). If patients participated in both the pharmacokinetic sampling and the optional biomarker blood collection, the baseline blood draw for the biomarkers was performed at least 2 days prior to Day 1 in order to reduce the amount of blood drawn with each venipuncture. Approximately 25 mL of blood was collected at each sampling point for molecular biomarker evaluations.

These biomarkers will include both RNA and DNA analysis performed using PCR based quantitative assays. For DNA biomarkers, loss of heterozygosity (LOH) of single-nucleotide polymorphism (SNP), Kras mutation, and methylation of promoter region of tumor-related genes were examined for both tumor tissue and blood. The expression of molecular biomarkers such as SPARC in PE tumor tissues were assessed for mRNA expression and specific epigenetic (promoter gene methylation) status to determine its potential clinicopathological utility related to treatment with Nab-paclitaxel. The objective was to assess specific tumor-related genes for up and down regulation and to identify specific gene expression patterns or specific biomarkers that relate to treatment response and disease outcome. In addition, PE tissue sections were obtained from tumor biopsy for immunohistochemistry (IHC) to assess SPARC and for molecular tumor biomarker validation. Tissues were collected from both randomized arms of the trial. Tumor tissue that was available from biopsy was used. Additional procedures will not be performed for the purpose of obtaining tumor tissue for molecular biomarker analyses.

In addition, blood biomarkers that have shown prognostic utility in monitoring patients during treatment [circulating tumor cells (CTC) and circulating DNA (cDNA)] were assayed. These assays may provide an alternative approach to better predict metastatic disease recurrence, disease response, and aid in the disease management of lung cancer patients. For the testing of these biomarkers, patients were requested to provide an additional volume of blood (approx. 25 mL) at baseline and on Day 1 of every other cycle thereafter, at the time of routine sampling for blood counts and chemistries (see schedule of events).

Tumor samples were collected from patients treated on this study to obtain preliminary data on a potential correlation between SPARC expression and response to combined therapy with Nab-paclitaxel/Carboplatin or Taxol/Carboplatin. In those cases where tumor samples from patients treated on this study were available, tumor samples were submitted to a central laboratory for SPARC analysis. Samples were run blinded to the treatment assignment and to the response the patient had to treatment.

The correlation of SPARC and other molecular biomarkers with efficacy outcomes was analyzed. The following analyses were performed for each treatment regimen. Descriptive statistics were used to summarize biomarkers for responders versus non-responders. Continuous measures were summarized by sample size, mean, median, S D, minimum, and maximum values. Categorical measures were summarized by number and percentage of patients in each category. To assess relationship between objective tumor response and biomarkers, a logistic regression analysis was performed with an effect for biomarker in the model. Relationship with disease control was analyzed in a similar manner. To assess the relationship of PFS with biomarkers, a Cox regression analysis was used with an effect for biomarker in the model. In addition, for SPARC and other biomarkers with binary measures, PFS was summarized by median PFS time (including 95% CI) for each biomarker category along with the hazard ratio (including 95% CI). The Kaplan-Meier curve for PFS was presented graphically for each biomarker category and differences in the curves were tested using the log-rank test.

Results

Baseline and histologic characteristics were well balanced in the two arms. Dose intensity of paclitaxel was higher in the Nab-paclitaxel/Carboplatin v. Taxol/Carboplatin arm (82 vs. 65 mg/m$^2$/wk). Nab-paclitaxel/Carboplatin overall response rate (ORR) was superior to Taxol/Carboplatin both by independent radiologic review (IRR) (33% vs. 25%, P=0.005), a 31% improvement, and by investigator review (37% vs. 30%, P=0.008), a 26% improvement. Analysis by histology revealed significantly improved ORR for Nab-paclitaxel/Carboplatin vs. Taxol/Carboplatin in squamous cell carcinoma patients (41% vs. 24%, P<0.001, IRR), a 67% improvement, and Nab-paclitaxel/Carboplatin was as effective as Taxol/Carboplatin in nonsquamous cell carcinoma patients (ORR 26% vs. 25%). Nab-paclitaxel/Carboplatin was well tolerated, with significantly improved safety profile vs. Taxol/Carboplatin despite the higher cumulative paclitaxel dose delivered (1442 mg/m$^2$ vs. 1131 mg/m$^2$) without premedication:

| Statistically significant events | Nab-paclitaxel/ Carboplatin n = 514 | Taxol/ Carboplatin n = 524 | P-value |
|---|---|---|---|
| G ≥3 Nonhematologic, n (%) | | | |
| Neuropathy | 15 (3) | 56 (11) | <0.001 |
| Myalgia | 1 (<1) | 10 (2) | 0.011 |
| Arthralgia | 0 | 8 (2) | 0.008 |
| G 4 Hematologic, n (%) | | | |
| Neutropenia | 49 (11) | 98 (22) | <0.001 |
| Thrombocytopenia | 23 (5) | 5 (1) | 0.001 |
| Anemia | 21 (5) | 4 (1) | 0.001 |

Nab-paclitaxel/Carboplatin significantly improved ORR and safety profile vs. Taxol/Carboplatin as first-line therapy for advanced NSCLC. Nab-paclitaxel/Carboplatin was especially active in the difficult to treat squamous cell carcinoma subset, which may in part be attributed to increased intratumoral Nab-paclitaxel/Carboplatin delivered via the gp60-CAV1 pathway in squamous carcinoma cells (Yoo et al. Lung Cancer. 2003 42:195-202) with aberrant CAV1 overexpression.

Example 2

Treatment of Lung Cancer

This example provides results from a phase 3 trial which studied the efficacy of Abraxane® (Nab-paclitaxel or nab-P) vs Taxol® (P) in combination with carboplatin (nab-PC v. PC) in advanced non-small cell lung cancer (NSCLC) of all histologic types.

Methods: First-line Stage IIIB or IV NSCLC pts (ECOG 0/1) were randomized to C AUC6 q3w and either nab-P 100 mg/m2 weekly without premedication (n=521) or P 200 mg/m2 once every three weeks with premedication (n=531). Primary endpoint: ORR by independent radiologic review (IRR).

Results: Baseline and histologic characteristics were well balanced. Dose intensity of paclitaxel was higher in nab-PC vs PC (82 vs 65 mg/m2/wk). nab-PC was superior to PC both by IRR (33% vs 25%, P=0.005), a 31% improvement (1.313 response ratio (RR), 95% CI: 1.082, 1.593), and by investigator review (37% vs 30%, P=0.008), a 26% improvement (1.259 RR, CI: 1.060, 1.496). Histologic analysis showed significantly improved ORR for nab-PC vs PC in squamous cell carcinoma (SQC) pts (41% vs 24%, P<0.001, IRR), a 67% improvement (1.669 RR, CI: 1.262, 2.208). nab-PC was as effective as PC in non-SQC pts (ORR 26% vs 25%). nab-PC was well tolerated, with significantly improved safety profile vs PC despite higher paclitaxel dose delivered (1338 vs 1100 mg/m2).

| Statistically significant events | nab-PC n = 514 | PC n = 524 | P-value |
|---|---|---|---|
| G ≥3 Nonhematologic, n (%) | | | |
| Neuropathy | 15 (3) | 56 (11) | <0.001 |
| Myalgia | 1 (<1) | 10 (2) | 0.011 |
| Arthralgia | 0 | 8 (2) | 0.008 |
| G 4 Hematologic, n (%) | | | |
| Neutropenia | 49 (11) | 98 (22) | <0.001 |
| Thrombocytopenia | 23 (5) | 5 (1) | 0.001 |
| Anemia | 21 (5) | 4 (1) | 0.001 |

Conclusions: nab-PC significantly improved ORR and safety profile vs PC as first-line therapy for advanced NSCLC. nab-PC was especially active in the SQC subset, which may in part be attributed to the aberrant CAV1 overexpression in squamous carcinoma cells (Yoo 2003) and the high intratumoral accumulation of nab-P via the gp60-CAV1 pathway.

Example 3

A Phase I/II Trial of Nab-Docetaxel in Patients with Hormone-Refractory Prostate Cancer The clinical study determined the maximum tolerated dose (MTD) and dose-limiting toxicities (DLTs) of Nab-docetaxel given every 3 weeks; characterized the toxicities of Nab-docetaxel; and determined the pharmacokinetic parameters for Nab-docetaxel when given on an every-3-week schedule. The study also evaluated the efficacy of Nab-docetaxel in this patient population.

Treatment Design

This Phase I study determined the MTD and DLT of Nab-docetaxel administered every 3 weeks. The starting dose of Nab-docetaxel was chosen based upon nonclinical data and the experience with solvent-based docetaxel.

Dosing escalation schedule (Nab-docetaxel administered on Day 1 of an every-3-week cycle): the dosages included were 30, 45, 60, 75, 100, 125, 150, 175, and 200 mg/m$^2$.

Three patients were enrolled at each dose level, starting at dose level 1. If no DLT was observed, 3 patients were enrolled at the next dose level. If 1 DLT was observed, the dose level was expanded to up to 6 patients. If 2 DLTs were observed at a given dose level, the MTD had been exceeded. The dose level below was expanded to a total of 6 patients, and if <1 out of 6 patients experience a DLT at this dose level, this was defined as the MTD. All patients at a given dose level completed one cycle of therapy before patients were enrolled at the next dose level. In the Phase II portion of the study, up to an additional 35 patients were enrolled at the MTD, for a maximum of 41 patients at that dose level (including 6 patients from the Phase I portion of the study). The maximum total number of patients treated in this study was 77 patients.

The Phase II MTD had established at 75 mg/m$^2$.

Patients continued on treatment until they experience progressive disease or unacceptable toxicity, withdraw consent, or their physician feels it was no longer in their best interest to continue on treatment. Each cohort received 1 cycle of treatment prior to dose escalation.

A DLT was defined in this study as any Grade 3 or 4 treatment-related non-hematological toxicity using the National Cancer Institute Common Terminology Criteria for Adverse Events (NCI CTCAE) (excluding nausea and vomiting); Grade 3 or 4 nausea or vomiting that occurs despite treatment; Grade 4 thrombocytopenia or anemia of any duration and Grade 4 uncomplicated neutropenia (i.e. without fever or infection) lasting>7 days. Neutropenia associated with fever or infection was considered to be a DLT, regardless of duration, or any Grade 3 hematologic toxicity requiring treatment delay beyond 3 weeks. DLTs were determined in Cycle 1 for the purposes of dose escalation and determining MTD.

The study consisted of the following phases (See Time and Events Schedule):

Baseline evaluations (imaging scans were performed within 28 days of the initiation of study drug dosing).

Treatment: Therapy continued in the absence of disease progression (based on PSA evaluation, tumor response, and radionuclide bone scans) and unacceptable toxicity.

PSA Evaluations: Patients had PSA evaluations done on Day 1 of each cycle. Caveolin-1 levels was measured on Day 1 of each cycle.

Tumor Response Assessments: Patients were evaluated for complete response (CR), partial response (PR), stable disease (SD), or progressive disease (PD) every 12 weeks or at the time of PSA progression or the development of new symptoms, until disease progression. Tumor response was evaluated using RECIST Criteria.

Pharmacokinetic Sampling—Cycle 1 of Phase I only. Parameters determined included volume of distribution, terminal half-life, $C_{max}$, $t_{max}$, $AUC_{inf}$, and plasma clearance.

End-of-Study (EOS) Evaluation: At the time patients were removed from study, laboratory and clinical evaluations to assess AEs were performed. Radiologic studies for antitumor response were repeated if they have not been done within the previous 28 days.

Adverse Event Collection and Follow-up—Any AE whose onset occurred between the first administration of study drug to 30 days after the last dose of study drug, whichever was later, were collected.

Disease Progression Follow-up: Patients who have not had progressive disease by the EOS evaluation continued to have PSA evaluations taken every 3 weeks and tumor response assessments conducted every 12 weeks until progressive disease (based on PSA evaluation or tumor response) was documented.

Table 4 provides a summary.

enrollment (6 weeks withdrawal for Casodex; 4 weeks for flutamide)), 7) Megestrol acetate (Megace®) treatment could continue if patient had been on stable doses of the drug. If patients discontinued Megace, they showed pro-

TABLE 4

Time and Events Schedule

| Assessment | Baseline | Each Cycle | | | Every 12 weeks | EOS$^A$ | AE Resolution$^B$ | PFS Follow-Up |
|---|---|---|---|---|---|---|---|---|
| | | Day 1 | Day 8 | Day 15 | | | | |
| Informed Consent | X | — | — | — | — | — | — | — |
| Medical History | X$^N$ | — | — | — | — | — | — | — |
| CT or MRI Scan of Chest/Pelvis/Abdomen$^C$ & any other studies required for tumor imaging | X | — | — | — | X$^C$ | X$^D$ | — | X |
| Chest X-Ray | X | — | — | — | X | — | — | — |
| Bone Scan | X | — | — | — | X | X$^D$ | — | — |
| CT Scan or MRI of Head (if clinically indicated)$^E$ | X | — | — | — | — | — | — | — |
| PSA and Caveolin-1 | X$^N$ | X$^F$ | — | — | — | X | — | X$^G$ |
| BSA Calculation and Height$^H$ | X$^N$ | — | — | — | — | — | — | — |
| Weight/Zubrod Performance Status | X$^N$ | X$^F$ | — | — | — | X | X | — |
| Physical Examination | X$^N$ | X$^F$ | — | — | — | X | X | — |
| Concomitant Medication Evaluation | X$^N$ | X | — | — | — | X | X | — |
| Concomitant Procedures Evaluation | — | X | — | — | — | X | X | — |
| Peripheral Neuropathy Assessment (physician and patient) | X$^N$ | X$^F$ | — | — | — | X | X | — |
| Vital Signs (Temperature, Pulse Rate, Respiratory Rate and Blood Pressure) | X$^N$ | X$^I$ | | | — | X | X | — |
| Adverse Event Evaluation$^J$ | — | X | — | — | — | X | X | — |
| CBC, Differential, Platelet Count$^K$ | X$^N$ | X$^F$ | X | X | — | X | X | — |
| Clinical Chemistry Panel | X$^N$ | X$^F$ | — | — | — | X | X | — |
| Study Drug Administration$^L$ | — | X | — | — | — | — | — | — |

$^A$EOS = End-of-Study. When patient comes off study the indicated tests were done. Repeat studies for tumor response only if not done within the previous 28 days.
$^B$Follow-up for AEs and SAEs continued through 30 days after the patient discontinued the study drug. Any AEs/SAEs that begin during this time were followed until stable and no longer improving or until they have resolved. If there are no AEs or SAEs ongoing at the EOS visit, follow up may be by telephone to the patient weekly until 30 days from last dose of treatment.
$^C$CT or MRI scan of the abdomen, and pelvis were performed at Baseline and every 12 weeks or at the time of PSA progression or the development of new symptoms, until disease progression. Whichever method was chosen at baseline to follow tumors remained consistent throughout study duration.
$^D$Restaging studies were also to be done at the EOS visit if not done in the preceding 28 days, unless there was otherwise clear clinical evidence of progression.
$^E$A CT scan of head could be performed if symptomology of brain metastasis existed (only if clinically indicated).
$^F$If Baseline labs, physical exam, weight, Zubrod, and peripheral neuropathy assessment (physician and patient), PSA and Caveolin-1 had been completed within 72 hours prior to treatment, these assessments did not need to be repeated on Cycle 1, Day 1.
$^G$PSA evaluations were collected every 3 week until disease progression.
$^H$BSA calculated at Baseline and recalculated only if body weight changes by more than 10%.
$^I$Pre and post Nab-docetaxel infusion.
$^J$Completed prior to the first dose of each cycle.
$^K$Study drug must not be administered at the start of a cycle until the ANC has returned to ≥1.5 × 10$^9$/l, and platelets have returned to ≥100 × 10$^9$/l, or any other toxicity resolves to Grade 1.
$^L$Nab-docetaxel on Day 1 of each cycle, plus prednisone 5 mg orally twice daily (morning and evening).
$^M$Prior to Cycle 2 only.
$^N$Required within 10 days prior to the first dose of study drug.

Inclusion/Exclusion Criteria

A patient was eligible for inclusion in this study only if all of the following criteria were met: 1) patients must have had histologically or cytologically confirmed adenocarcinoma of the prostate that is clinically refractory to hormone therapy, 2) Zubrod Performance Status 0-1, 3) at the time of enrollment, patients must have had evidence of progressive metastatic disease, either: a) measurable disease with any level of serum PSA or b) non-measurable disease with PSA≥5 ng/ml. (Patients with PSA≥5 ng/ml only and no other radiographic evidence of metastatic prostate cancer were not eligible), 4) patients must have demonstrated evidence of progressive disease since the most recent change in therapy, 5) serum testosterone≤50 ng/ml, determined within two weeks prior to starting treatment, 6) maintained castrate status (Patients who have not undergone surgical orchiectomy continued on medical therapies [e.g. gonadotropin releasing hormone analogs (GnRH analogs)] to maintain castrate levels of serum testosterone. Patients who were receiving an anti-androgen as part of their first-line hormonal therapy showed progression of disease off of the anti-androgen prior to gression of disease off of this medication, 8) age≥18 years of age, 9) four weeks since major surgery, 10) the following restrictions on prior therapy for metastatic disease apply: a) no prior chemotherapy regimen for metastatic disease, b) no more than one prior course of palliative radiotherapy, c) up to one prior treatment with a non-chemotherapeutic agent (e.g., kinase inhibitors, immunotherapeutic agents, etc) was permitted as treatment for metastatic disease, d) no prior radioisotope therapy with Strontium-89, Samarium or similar agents, and e) one prior neo-adjuvant or adjuvant chemotherapy regimen was permitted if given over 3 years ago, 11) no limitation on prior hormonal therapy, 12) patients were off all therapy for at least 4 weeks prior to study drug administration, 13) life expectancy was ≥3 months, 14) patients signed an informed consent document stating that they understood the investigational nature of the proposed treatment, 15) required Initial Laboratory Data: a) WBC≥3,000 µl, b) ANC≥1,500 µl, c) platelet count≥100,000 µl, d) creatinine≤1.5× upper limits of normal, e) total Bilirubin≤upper limit of normal (exceptions will be made for patients with Gilbert's Disease), f) SGOT (AST)≤1.5× upper limits of normal, and f) SGPT (ALT)≤1.5× upper limits of normal, 16) taxanes are considered to be teratogenic (For this reason men whose sexual partners were of child-bearing age agreed to use adequate contraception (hormonal or barrier method of birth control) for the duration of study participation.), and 17) if obese (weight>20% of ideal body weight) patient must be treated with doses calculated using adjusted body surface area (BSA) (based on calculated adjusted weight) or actual BSA.

Progressive disease in the inclusion criteria was defined as any one of the following (measurable disease, bone scan, or PSA progression): 1) measurable Disease Progression (Objective evidence of increase>20% in the sum of the longest diameters (LD) of target lesions from the time of maximal regression or the appearance of one or more new lesions.), 2) bone scan progression (Appearance of either of the following constituted progression: (a) two or more new lesions on bone scan attributable to prostate cancer; or (b) one new lesion on bone scan attributable to prostate cancer in conjunction with a rising PSA.), or 3) PSA Progression (In the presence of radiographic evidence of disease, an elevated PSA (≥5 ng/mL) which has risen serially from baseline on two occasions each at least one week apart. If the confirmatory PSA value was less than screening PSA value, then an additional test for rising PSA was required to document progression.).

A patient was ineligible for inclusion in this study if any of the following criteria applied: 1) patients could not be receiving any other investigational agents, 2) patients could continue on a daily Multi-Vitamin, low dose (≤400 IU qd) Vitamin D, Calcitrol (≤0.5 mcg qd), and calcium supplements, but all other herbal, alternative and food supplements (i.e. PC-Spes, Saw Palmetto, St John Wort, etc.) must be discontinued before start of treatment, 3) patients on stable doses of bisphosphonates, who develop subsequent tumor progression, could continue on this medication. (However, patients were not allowed to initiate bisphosphonate therapy immediately prior to or during the study because starting bisphosphonates could potentially confound the interpretation of adverse events.), 4) patients with known brain metastases were excluded from this clinical trial because they often developed progressive neurologic dysfunction that could confound the evaluation of neurologic and other adverse events, 5) patients with history of allergic reactions attributed to solvent-based docetaxel (Taxotere) were not eligible for the study, 6) patients with significant cardiovascular disease including congestive heart failure (New York Heart Association Class III or IV), active angina pectoris or recent myocardial infarction (within the last 6 months) were excluded, 7) patients with a "currently active" second malignancy other than non-melanoma skin cancers were not to be registered. (Patients were not considered to have a "currently active" malignancy if they completed therapy and were now considered (by their physician) to be at low risk for relapse.), 8) uncontrolled intercurrent illness including, but not limited to, ongoing or active infection, symptomatic congestive heart failure, unstable angina pectoris, cardiac arrhythmia, or psychiatric illness/social situations that limited compliance with study requirements, or 9) because patients with immune deficiency were at increased risk of lethal infections when treated with marrow-suppressive therapy, HIV-positive patients receiving combination anti-retroviral therapy were excluded from the study because of possible pharmacokinetic interactions with docetaxel.

Dosages and Administration

All patients were treated with Nab-docetaxel IV (60 minutes infusion±5 minutes) administered every 3 weeks plus prednisone 5 mg orally administered twice daily (morning and evening). Cohorts of 3 patients each received 60, 75, 100, 125, 150, 175 or 200 mg/m$^2$ Nab-docetaxel as a 1-hour infusion on Day 1 of each cycle of Phase I. The dose of Nab-docetaxel was escalated depending on the toxicity profile observed in the previous 3-patient cohort.

Efficacy Endpoints

The primary efficacy endpoint was percentage of patients who achieved a confirmed prostate-specific antigen (PSA) response where PSA response was defined as either PSA normalization or a PSA decline. PSA normalization was defined as PSA<1.0 ng/ml for patients whose primary disease was treated with radiotherapy only and PSA undetectable for patients who have had a prostatectomy, for 2 successive evaluations at least 4 weeks apart. PSA decline was defined as a decrease in PSA value by ≥50% from pre-treatment for 2 successive evaluations at least 4 weeks apart. The pre-treatment PSA value was measured within 2 weeks before starting therapy.

Secondary efficacy endpoints included: a) percentage of patients with measurable disease who achieve an objective confirmed complete or partial overall tumor response using Response Evaluation Criteria in Solid Tumors (RECIST) Criteria, b) time to PSA Progression, c) progression-free survival based on tumor response using RECIST Criteria.

PSA Evaluation

In previous work others have shown the prognostic significance of post-therapy decline in PSA. Tahir S A et al. *Clin Cancer Res.* 2003; 9:3653-9. Based on this work a NCI consensus group proposed the following guidelines for the use of post-therapy PSA changes in androgen-independent disease. Kelly W K et al. *J Clin Oncol.* 1993; 11:607-615.

PSA normalization defined as PSA<1.0 ng/ml for patients whose primary disease was treated with radiotherapy only and PSA undetectable for patients who have had a prostatectomy, for 2 successive evaluations at least 4 weeks apart.

PSA decline defined as a decrease in PSA value by ≥50% from pre-treatment for 2 successive evaluations at least 4 weeks apart. The pre-treatment PSA value was measured within 2 weeks before starting therapy.

PSA progression defined as the date of PSA increase meeting the criteria of progression (i.e., not the date of confirmation).

In patients who have achieved a ≥50% decline in PSA, progression was defined by: 1) an increase in PSA by 50% above the nadir and 2) an increase in PSA by a minimum of 5 ng/mL, or an increase in PSA to the pretreatment PSA value, and 3) confirmation by a second consecutive rising PSA at least 2 weeks apart.

In patients whose PSA has not decreased by ≥50%, progression was defined by: 1) an increase in PSA by 25% above either the pre-treatment level, or the nadir PSA level (whichever is lowest) and 2) an increase in PSA by a minimum of 5 ng/mL and 3) confirmation by a second consecutive rising PSA at least 2 weeks apart.

Note: If confirmation was not observed because the patient began a new anti-cancer therapy following the initial observed PSA progression, then the patient was considered to have confirmed PSA progression.

Response

At baseline, tumor lesions were categorized as follows: measurable (lesions that could be accurately measured in at least 1 dimension [longest diameter to be recorded] as ≥20 mm with conventional techniques or as ≥10 mm with spiral CT scan) or nonmeasurable (all other lesions, including small lesions [longest diameter<20 mm with conventional techniques or <10 mm with spiral CT scan] and truly nonmeasurable lesions).

All measurable lesions up to a maximum of 5 lesions per organ and 10 lesions in total, representative of all involved organs, were identified as target lesions and recorded and measured at baseline. Target lesions were selected on the basis of their size (those with the longest diameter) and their suitability for accurate repeated measurements (either by imaging techniques or clinically). A sum of the longest diameter for all target lesions were calculated and reported as the baseline sum longest diameter. The baseline sum longest diameter was used as the reference by which to characterize the objective tumor response.

All other lesions (or sites of disease) were identified as nontarget lesions.

Antitumor activity will be evaluated in patients with measurable and/or nonmeasurable lesions according to RECIST guidelines.

The following definitions were used to evaluate response based on target lesions at each time point after baseline: Complete Response (CR): The disappearance of all known disease and no new sites or disease related symptoms confirmed at least 4 weeks after initial documentation. All sites were assessed, including non-measurable sites, such as effusions, or markers. Partial Response (PR): At least a 30% decrease in the sum of the longest diameters of target lesions, taking as a reference the baseline sum of the longest diameters confirmed at least 4 weeks after initial documentation. PR was also recorded when all measurable disease has completely disappeared, but a non-measurable component (i.e., ascites) was still present but not progressing. Stable Disease (SD): Neither sufficient shrinkage to qualify for partial response nor sufficient increase to qualify for progressive disease. Progressive Disease (PD): At least a 20% increase in the sum of the longest diameters of target lesions, taking as reference the smallest sum of the longest diameters recorded since the treatment started; or the appearance of one or more new lesions; or the unequivocal progression of a non-target lesion.

Response assessments of Non Target lesions were defined as follows: Complete Response (CR): Disappearance of all non-target lesions and the normalization of tumor marker level confirmed at least 4 weeks after initial documentation. Stable Disease (SD): Persistence of one or more non-target lesion(s) and/or the maintenance of tumor marker level above the normal limits Progressive Disease (PD): The appearance of one or more non-target lesions and/or unequivocal progression of existing non-target lesions. Unable to Evaluate (UE): No non-target lesion(s) documented at Baseline, or since treatment started.

Time to PSA Progression

Time to PSA progression was summarized using Kaplan-Meier methods. Time PSA progression was defined as the time from first dose of study drug to the start of PSA progression. Patients who did not have PSA progression at the end of follow-up were censored at the time of their last PSA evaluation.

Progression-Free Survival Based on Tumor Response

Progression-free survival was summarized using Kaplan-Meier methods. Progression-free survival was defined as the time from first dose of study drug to the start of disease progression or patient death (any cause) whichever occurs first. Patients who did not have disease progression or have not died were censored at the last known time that the patient was progression free.

Safety/Tolerability Endpoints

The primary safety endpoint was determining the MTD and DLTs of Nab-docetaxel in patients with HRPC. Other secondary safety/tolerability endpoints include the incidence of treatment emergent adverse events (AEs) and serious adverse events (SAEs), laboratory abnormalities and nadir of myelosuppression during study drug dosing, and percentage of patients experiencing dose modifications, dose interruptions, and/or premature discontinuation for each study drug.

AEs occurring during the study were graded according to the NCI Common Terminology Criteria for Adverse Events v3.0 (CTCAE) (see http://ctep.cancer.gov/reporting/ctc.html), where applicable. AEs that were not included on the toxicity scale were designated as Grade 1=mild, Grade 2=moderate, Grade 3=severe, Grade 4=life-threatening, and Grade 5=death. Non-serious AEs that were determined not to be possibly, probably, or definitely related to study drug did not require further evaluation but were recorded. Study medications could be interrupted for an AE at the discretion of the investigator. Patients requiring toxicity management were assessed and evaluated at least weekly as indicated by the severity of the event.

According to the NCI CTCAE system of adverse event grading, laboratory values of Grade 3 or 4 were described as "severe" or "life-threatening." For example, a neutrophils count<500/mm3 would meet laboratory criteria as Grade 4 ("life-threatening"). This description was not always synonymous with the assessment of the "serious" criteria of an AE as "life threatening". Definition of AE and SAE are provided herein.

In order for AEs to be considered serious by "life-threatening" criteria, it was medically judged as possessing "an immediate risk of death from the event as it occurred," not because of the theoretical potential for life-threatening consequences. In the case of a neutrophil count<500/mm$^3$, the AE would be captured as an AE of Grade 4 neutropenia, but it was not automatically considered a SAE unless the investigational physician determined this represented an immediately life-threatening event for the patient. Specifically, uncomplicated Grade 4 neutropenia was not reported as a SAE. Neutropenia associated with fever, infection, or hospitalization was reported as a SAE.

Patients in the treated population were followed for the development of AEs from study drug initiation through the end of study or 30 days after the end of treatment, whichever was longer. Only patients with clear documentation that no study drug was administered could be excluded from the treated population.

Pharmacokinetic Endpoints

The pharmacokinetic endpoints include the elimination rate constant, elimination half-life, the volume of distribution ($V_z$), the maximum plasma drug concentration ($C_{max}$), $T_{max}$, the area under the plasma concentration versus time curve ($AUC_{inf}$) and plasma clearance.

Laboratory Assessments

Hematology Parameters—

To investigate the maximal degree of myelosuppression, the CTCAE grade for WBC, ANC, platelet count, and hemoglobin concentration were summarized by the most severe grade for the first treatment cycle and by the most severe grade anytime during therapy. The incidence of patients with CTCAE hematology values of Grade 3 or 4 that occurred after the first dose of study drug was presented for each group. Data for patients with Grade 3 or 4 hematology values were listed.

Clinical Chemistry—

Liver and renal functions were summarized using the CTCAE for ALT, AST, total bilirubin, and creatinine. The number and percentage of patients who have each CTCAE grade were summarized by the most severe grade for the first cycle of therapy and by the most severe grade anytime during therapy for each treatment regimen; testing of treatment regimen differences was performed using the CMH test. The incidence of patients with CTCAE chemistry values of Grade 3 or 4 that occurred after the first dose of study drug was presented for each group. Data for patients with Grade 3 or 4 chemistry values were listed.

Evaluation of Molecular Biomarkers

Expression levels of Caveolin-1 (Cav1) were evaluated.

Results

PSA (prostate specific antigen) response rate was measured in patients in 42 patients treated with a nanoparticle composition comprising albumin and docetaxel, namely, Nab-docetaxel (at a dose of 75 mg/m2 q3wk) or a combination of Nab-docetaxel and prednisone. In 13 patients treated with nab-docetaxel alone, a confirmed PSA response occurred in 3/13 (23%). In 29 patients treated with nab-docetaxel plus prednisone, a confirmed PSA response occurred in 13/29 (45%), almost double that seen with nab-docetaxel alone. Thus Nab based delivery of docetaxel allows for enhanced effect of prednisone on prostate cancer tumors.

Example 4

A Phase I Study of Nab-Paclitaxel with Carboplatin and Thoracic Radiation in Patients with Locally Advanced NSCLC One third of patients with NSCLC present with localized, unresectable disease. Concurrent chemoradiotherapy with weekly paclitaxel (Taxol) and carboplatin has with median survival of ~14 months. A phase I trial was initiated using weekly Nab-paclitaxel with carboplatin and thoracic radiation therapy in patients with unresectable stage III NSCLC to determine safety and tolerability.

Patients with inoperable Stage IIIA or IIIB NSCLC, PS 0-1, and FEV 1>800 ml entered escalating dose cohorts in a modified 3+3 design of Nab-paclitaxel weekly, beginning at 40 mg/m$^2$ and increasing by 20 mg/m$^2$ increments, in combination with carboplatin (AUC 2) weekly for 7 weeks and concurrent thoracic radiation in 33 fractions by either 3D conformal or intensity-modulated techniques. Patients received 2 cycles of consolidation therapy with full dose Nab-paclitaxel (100 mg/m$^2$ weekly for 3 weeks) and carboplatin (AUC 6 on day one of each cycle) every 21 d. The DLT (dose limiting toxicity) period is defined as the concurrent chemoradiation period.

Results

Eleven patients were enrolled. Ten patients were treated at 2 dose levels of Nab-paclitaxel, 40 mg/m$^2$ (6 patients) and 60 mg/m$^2$ (4 patients). One patient signed consent and then withdrew. 6 pts were treated at 40 mg/m$^2$ with no DLT. 4 pts were treated at 60 mg/m$^2$ with 2 DLT of radiation dermatitis and esophagitis. Grade 2-3 toxicities during concurrent treatment included: neutropenia, neutropenic fever, anemia, thrombocytopenia, fatigue, esophagitis, mucositis, nausea, dermatitis, hypoxia, and dehydration. No grade 4 toxicities were seen during concurrent treatment. Ten patients were evaluable for response with 9 partial response and 1 stable disease. Seven patients progressed 3, 5, 6, 7, and 8, 16 and 20 months after enrollment, and 3 patients remained stable at 2, 4, and 28 months. The recommended Phase II dose of weekly Nab-paclitaxel is 40 mg/m$^2$.

Weekly Nab-paclitaxel was safe and well tolerated at 40 mg/m$^2$ when used in combination with weekly carboplatin and thoracic radiation.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of treating NSCLC in an individual comprising administering to the individual a) an effective amount of a composition comprising nanoparticles comprising paclitaxel and an albumin and b) an effective amount of a platinum-based agent, wherein treatment is based upon the individual having squamous cellular carcinoma.

2. The method of claim 1, wherein the method comprises selecting the individual for treatment based on the individual having squamous cellular carcinoma.

3. The method of claim 1, wherein the effective amount of the composition comprising nanoparticles comprising paclitaxel and albumin is between about 50 mg/m$^2$ and about 125 mg/m$^2$.

4. The method of claim 1, wherein the composition comprising nanoparticles comprising paclitaxel and albumin is administered weekly.

5. The method of claim 1, wherein the effective amount of the platinum-based agent is between about AUC=2 and about AUC=6.

6. The method of claim 1, wherein the platinum-based agent is administered once every three weeks.

7. The method of claim 1, wherein the effective amount of the composition comprising nanoparticles comprising paclitaxel and albumin is 100 mg/m$^2$ administered weekly and the effective amount of the platinum-based agent is AUC=6 administered once every three weeks.

8. The method of claim 1, wherein paclitaxel in the nanoparticles is coated with albumin.

9. The method of claim 1, wherein the nanoparticles in the composition have an average diameter of no greater than about 200 nm.

10. The method of claim 1, wherein the NSCLC is Stage IIIB NSCLC or Stage IV NSCLC.

11. The method of claim 1, wherein the composition comprising nanoparticles comprising paclitaxel and albumin and the platinum-based agent are administered parenterally.

12. The method of claim 11, wherein the composition comprising nanoparticles comprising paclitaxel and albumin and the platinum-based agent are administered intravenously.

13. The method of claim 1, wherein the platinum-based agent is carboplatin.

14. The method of claim 1, wherein the individual is human.

15. The method of claim 1, wherein the method further comprises the administration of thoracic radiation.

16. The method of claim 15, wherein the effective amount of the composition comprising nanoparticles comprising paclitaxel and albumin is between about 20 mg/m$^2$ to about 60 mg/m$^2$ administered weekly, the effective amount of a platinum-based agent is between about AUC=2 to about AUC=6 administered weekly, and the thoracic radiation is between about 25 to about 40 fractions by either 3D conformal or intensity-modulated techniques concurrently.

17. The method of claim 1, wherein the weight ratio of albumin and paclitaxel in the nanoparticle composition is about 1:1 to about 9:1.

18. The method of claim 17, wherein the weight ratio of albumin and paclitaxel in the nanoparticle composition is about 9:1.

19. The method of claim 8, wherein the weight ratio of albumin and paclitaxel in the nanoparticle composition is about 1:1 to about 9:1.

20. The method of claim 9, wherein the weight ratio of albumin and paclitaxel in the nanoparticle composition is about 1:1 to about 9:1.

21. The method of claim 19, wherein the nanoparticles in the composition have an average diameter of no greater than about 200 nm.

22. The method of claim 13, wherein the weight ratio of albumin and paclitaxel in the nanoparticle composition is about 1:1 to about 9:1.

23. The method of claim 22, wherein the weight ratio of albumin and paclitaxel in the nanoparticle composition is about 9:1.

24. The method of claim 22, wherein paclitaxel in the nanoparticles is coated with the albumin.

25. The method of claim 24, wherein the nanoparticles in the composition have an average diameter of no greater than about 200 nm.

26. The method of claim 23, wherein paclitaxel in the nanoparticles is coated with the albumin.

27. The method of claim 26, wherein the nanoparticles in the composition have an average diameter of no greater than about 200 nm.

* * * * *